(12) United States Patent
     Chana

(10) Patent No.: US 11,617,661 B2
(45) Date of Patent: Apr. 4, 2023

(54) APPARATUS FOR USE IN SURGERY

(71) Applicant: Gursharan Singh Chana, Sutton Coldfield (GB)

(72) Inventor: Gursharan Singh Chana, Sutton Coldfield (GB)

(73) Assignee: Gursharan Singh Chana, Sutton Coldfield (GB)

( * ) Notice: Subject to any disclaimer, the term of this patent is extended or adjusted under 35 U.S.C. 154(b) by 77 days.

(21) Appl. No.: 17/057,165

(22) PCT Filed: May 28, 2019

(86) PCT No.: PCT/GB2019/051450
     § 371 (c)(1),
     (2) Date: Nov. 20, 2020

(87) PCT Pub. No.: WO2019/224561
     PCT Pub. Date: Nov. 28, 2019

(65) Prior Publication Data
     US 2021/0196478 A1    Jul. 1, 2021

Related U.S. Application Data

(60) Provisional application No. 62/676,469, filed on May 25, 2018.

(51) Int. Cl.
     *A61F 2/46*    (2006.01)
(52) U.S. Cl.
     CPC .... *A61F 2/4607* (2013.01); *A61F 2002/4619* (2013.01); *A61F 2002/4677* (2013.01); *A61F 2002/4687* (2013.01)

(58) Field of Classification Search
     CPC ............ A61F 2/4607; A61F 2002/4619; A61F 2002/4677; A61F 2002/4687; A61B 17/1668
     See application file for complete search history.

(56) References Cited

U.S. PATENT DOCUMENTS 5,476,466 A * 12/1995 Barrette ................ A61F 2/4607
                                                  606/86 R
5,951,564 A    9/1999 Schroder et al.
(Continued)

FOREIGN PATENT DOCUMENTS

WO    2011045568        4/2011
WO    2017032993 A1     3/2017

OTHER PUBLICATIONS

International Search Report and Written Opinion corresponding to International Patent Application No. PCT/GB2019/051450, dated Aug. 22, 2019.

*Primary Examiner* — Anu Ramana
(74) *Attorney, Agent, or Firm* — Myers Bigel, P.A.

(57) ABSTRACT

The invention provides a targeting device suitable for use in removing a femoral implant from the surrounding tissue, wherein the device comprises: (A) an anterior guide member (1), (B) a posterior guide member (4), (C) an engagement member (7), (D) a first pair of parallel connector rails (509, 510), and (E) an adjustment system (13). When the anterior guide member and the posterior guide member are connected by the first pair of connector rails, via the engagement member, the angled channels of the anterior guide member and the posterior guide member converge in the direction of a distal end, with the convergence angle of the angled channels being in the range of from 2 to 6 degrees, such as from 2 to 5 degrees.

18 Claims, 16 Drawing Sheets

(56) References Cited

U.S. PATENT DOCUMENTS

| | | |
|---|---|---|
| 2002/0099447 A1 | 7/2002 | Mears et al. |
| 2010/0298834 A1* | 11/2010 | Hildebrandt ....... A61B 17/1746 |
| | | 606/86 R |
| 2011/0046745 A1 | 2/2011 | Daniels et al. |
| 2012/0116406 A1 | 5/2012 | Talamini |

* cited by examiner

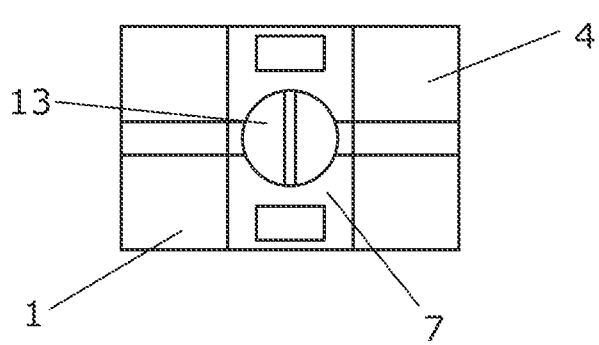
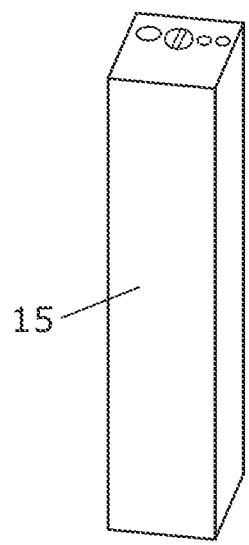
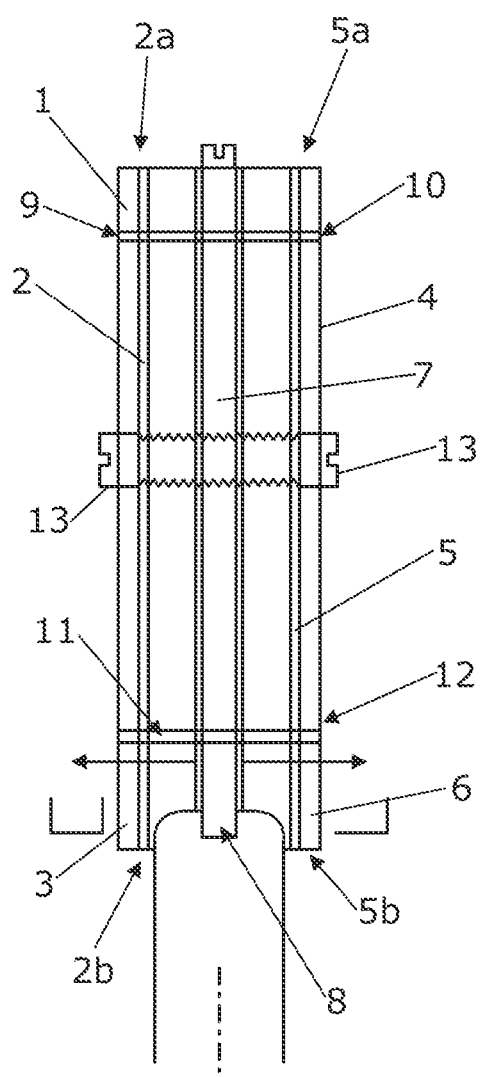
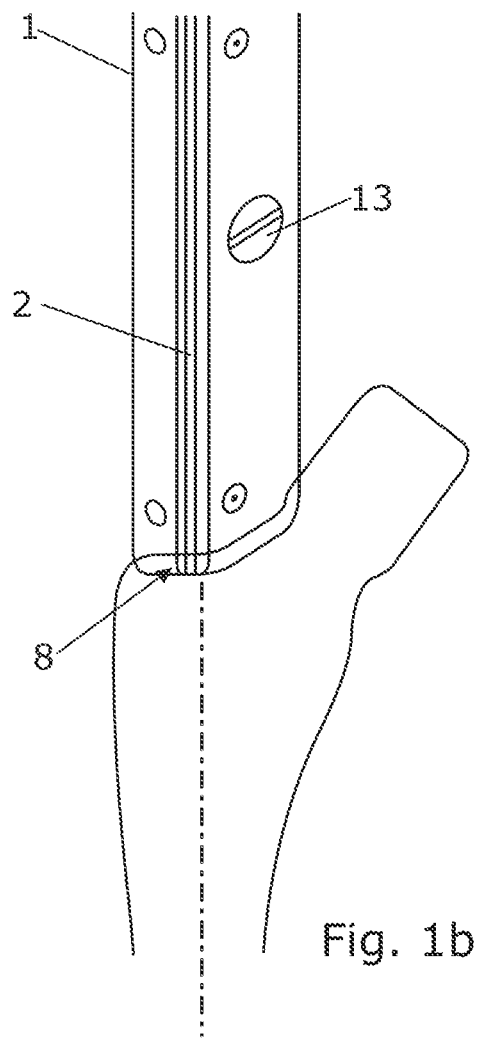
Fig. 1c
Fig. 1d
Fig. 1a
Fig. 1b

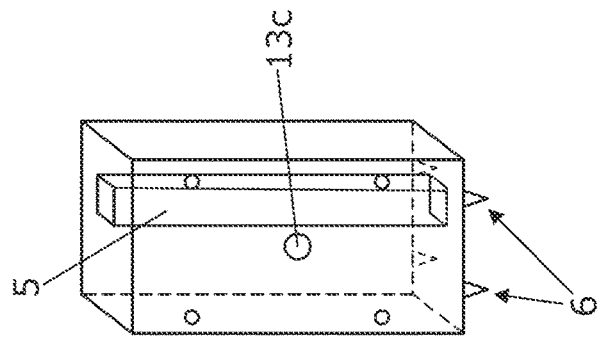
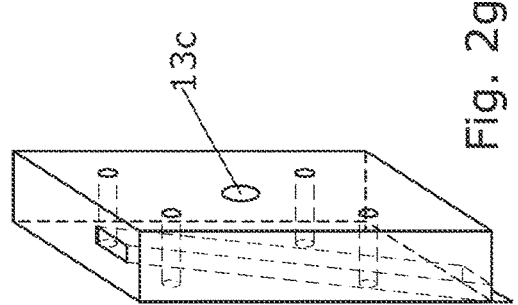
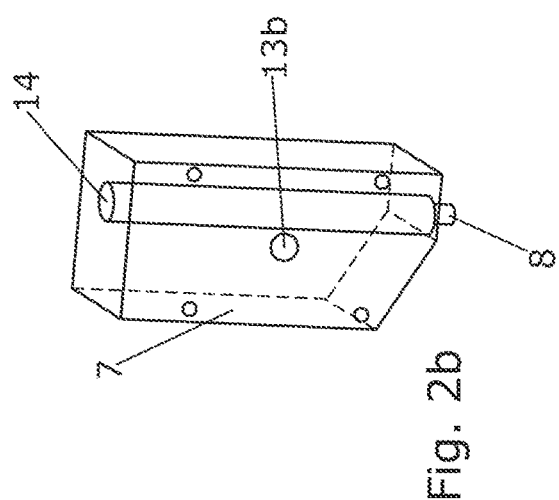
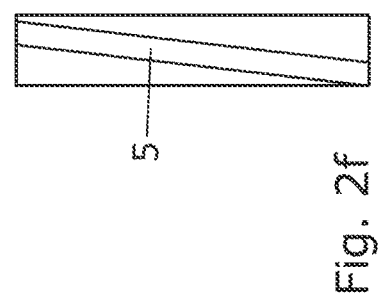
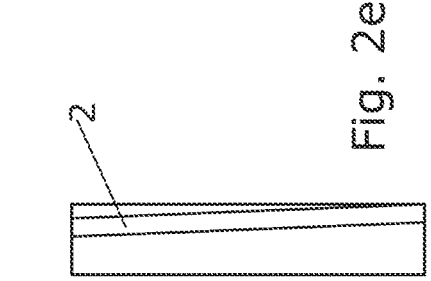
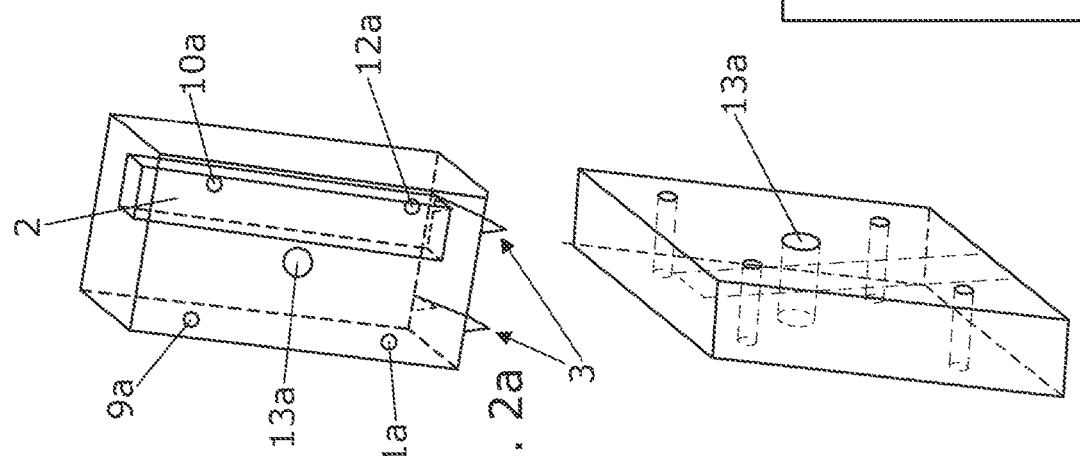

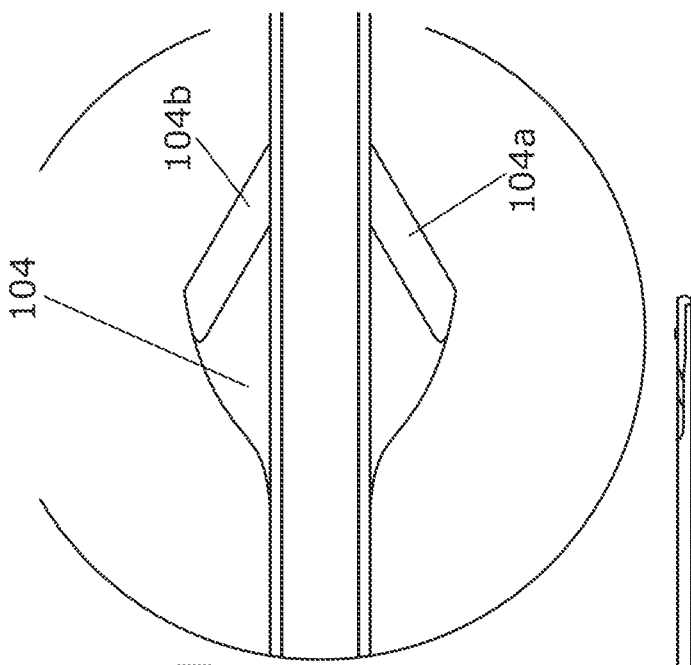
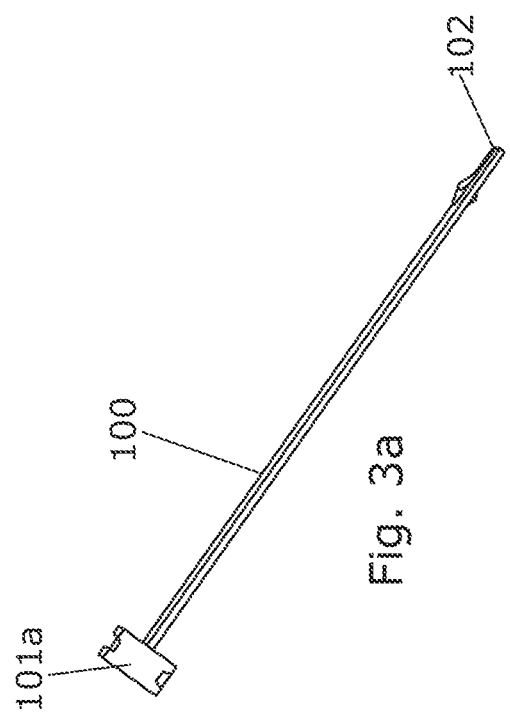
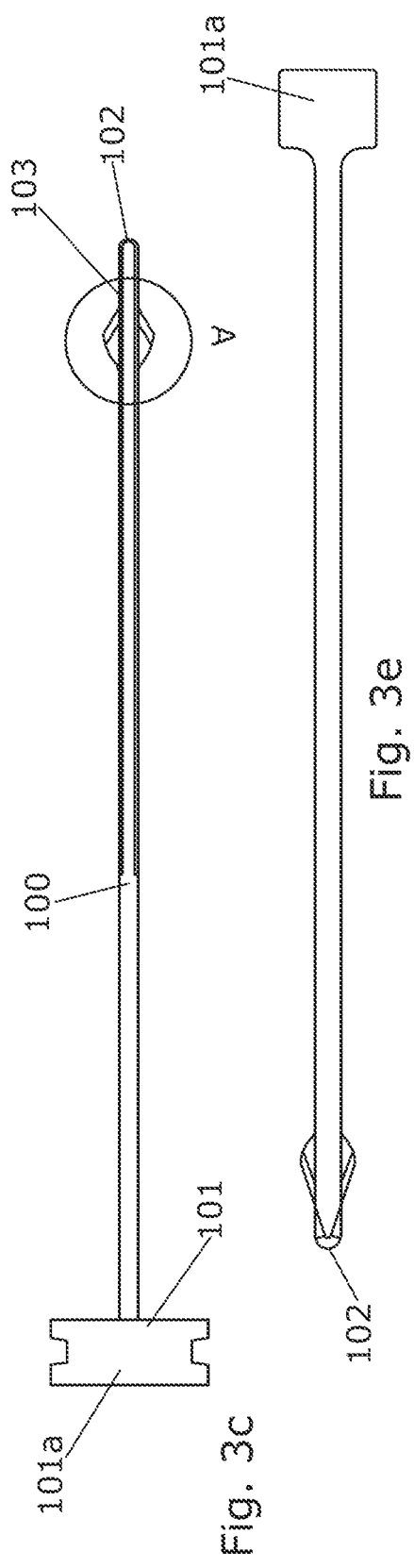

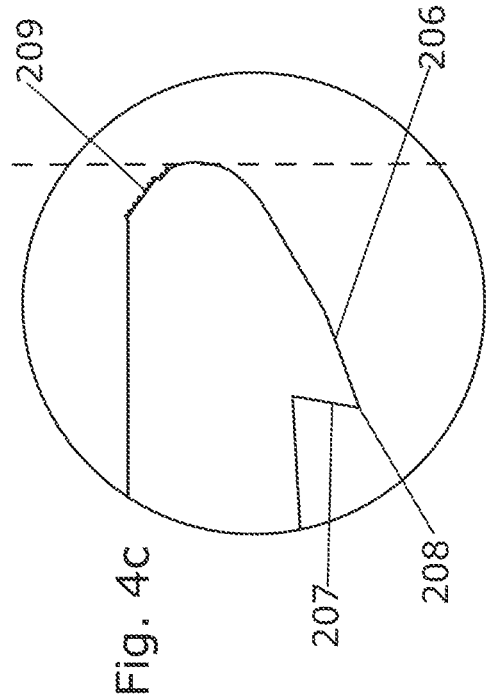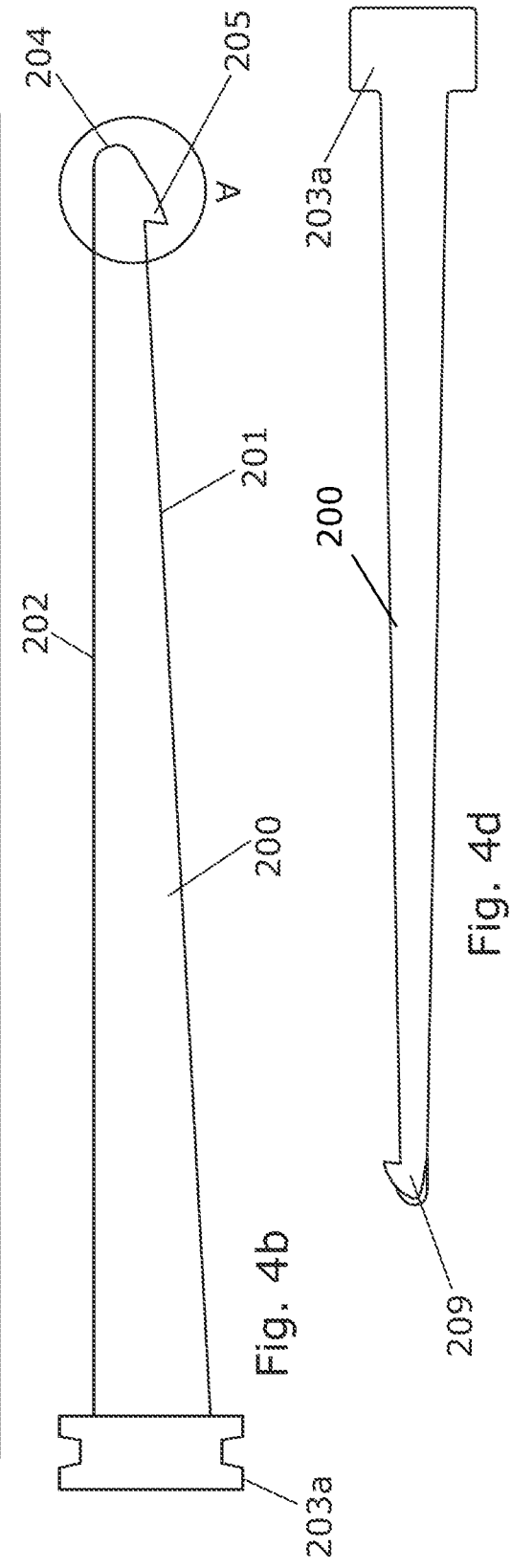

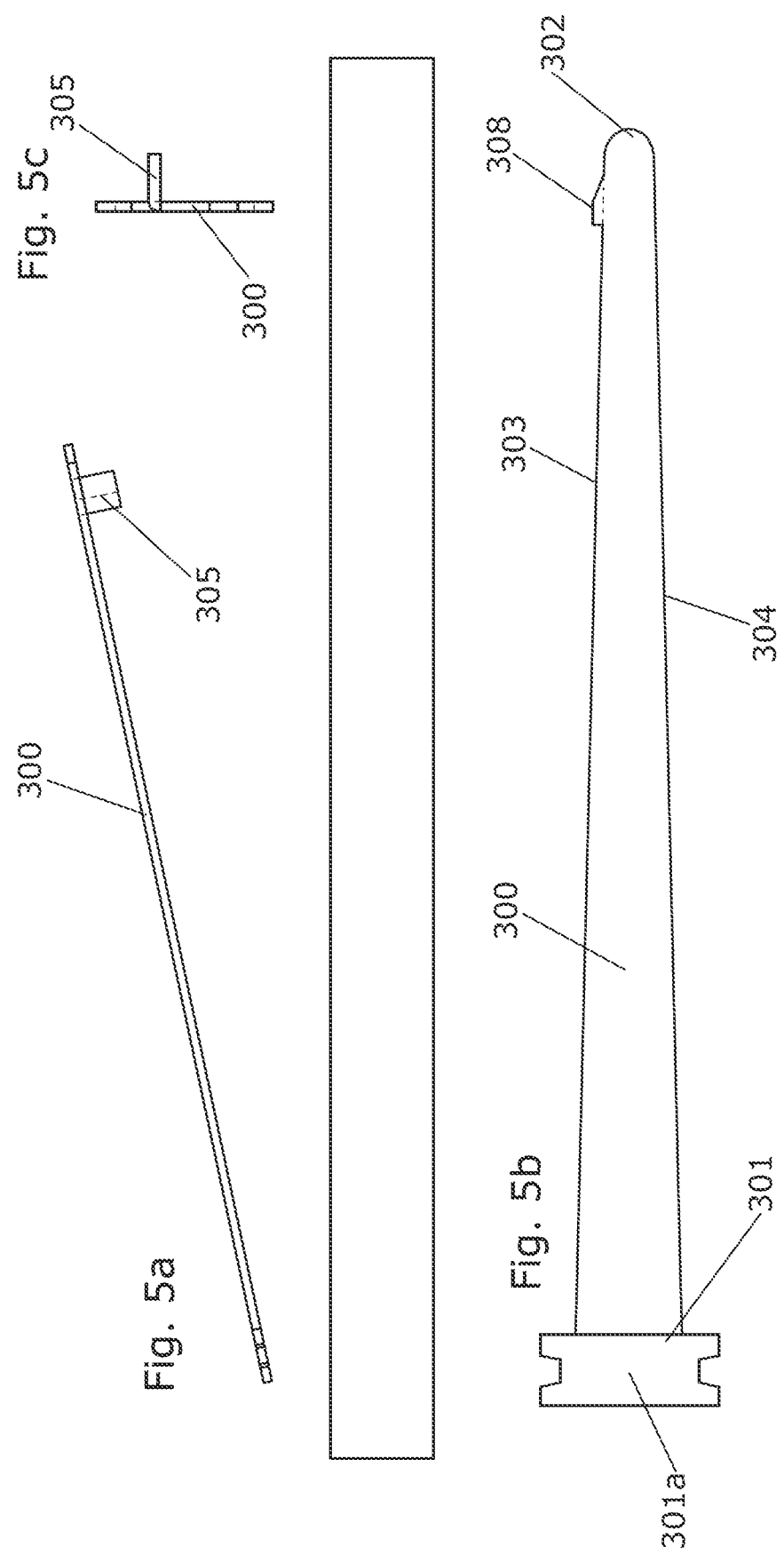

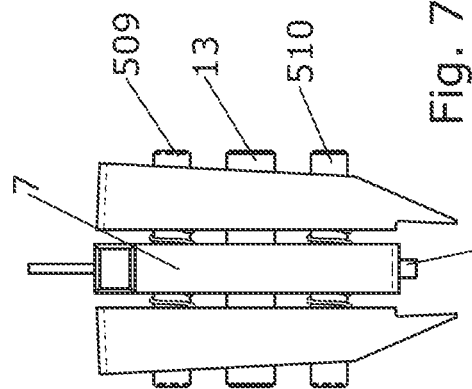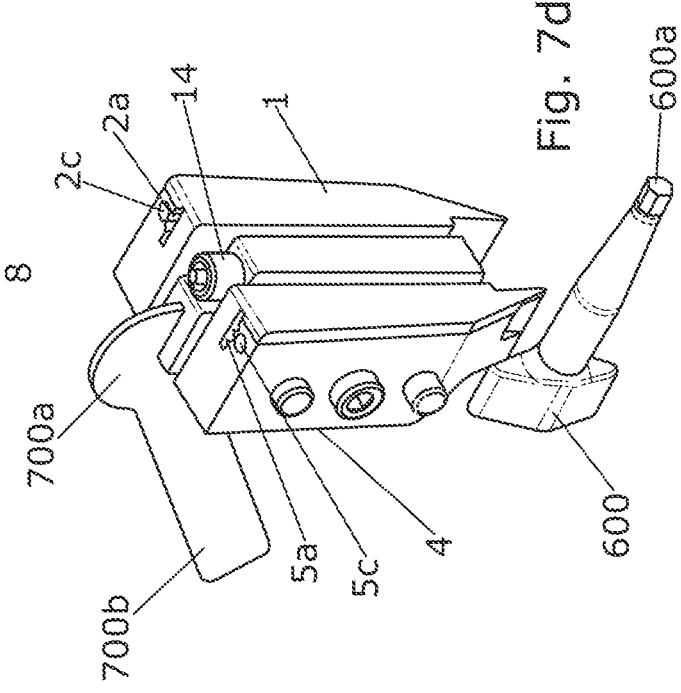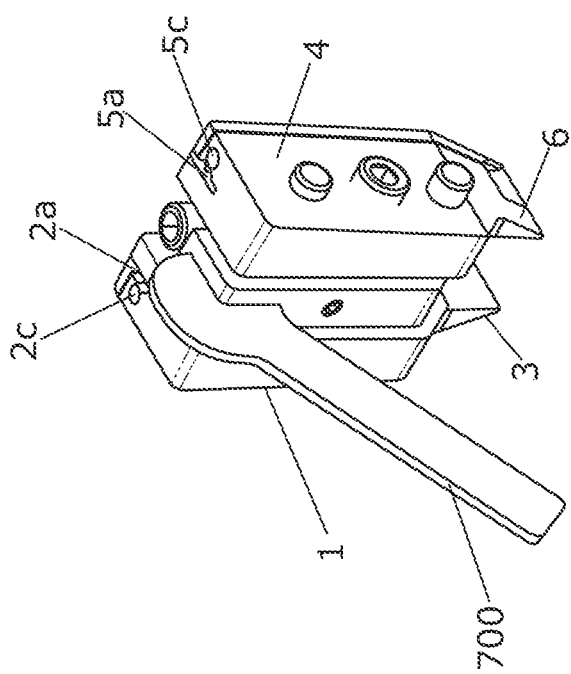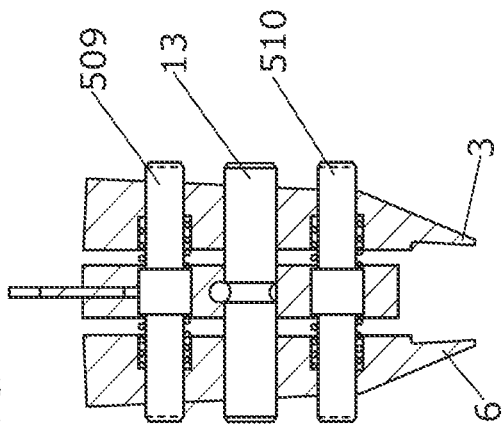

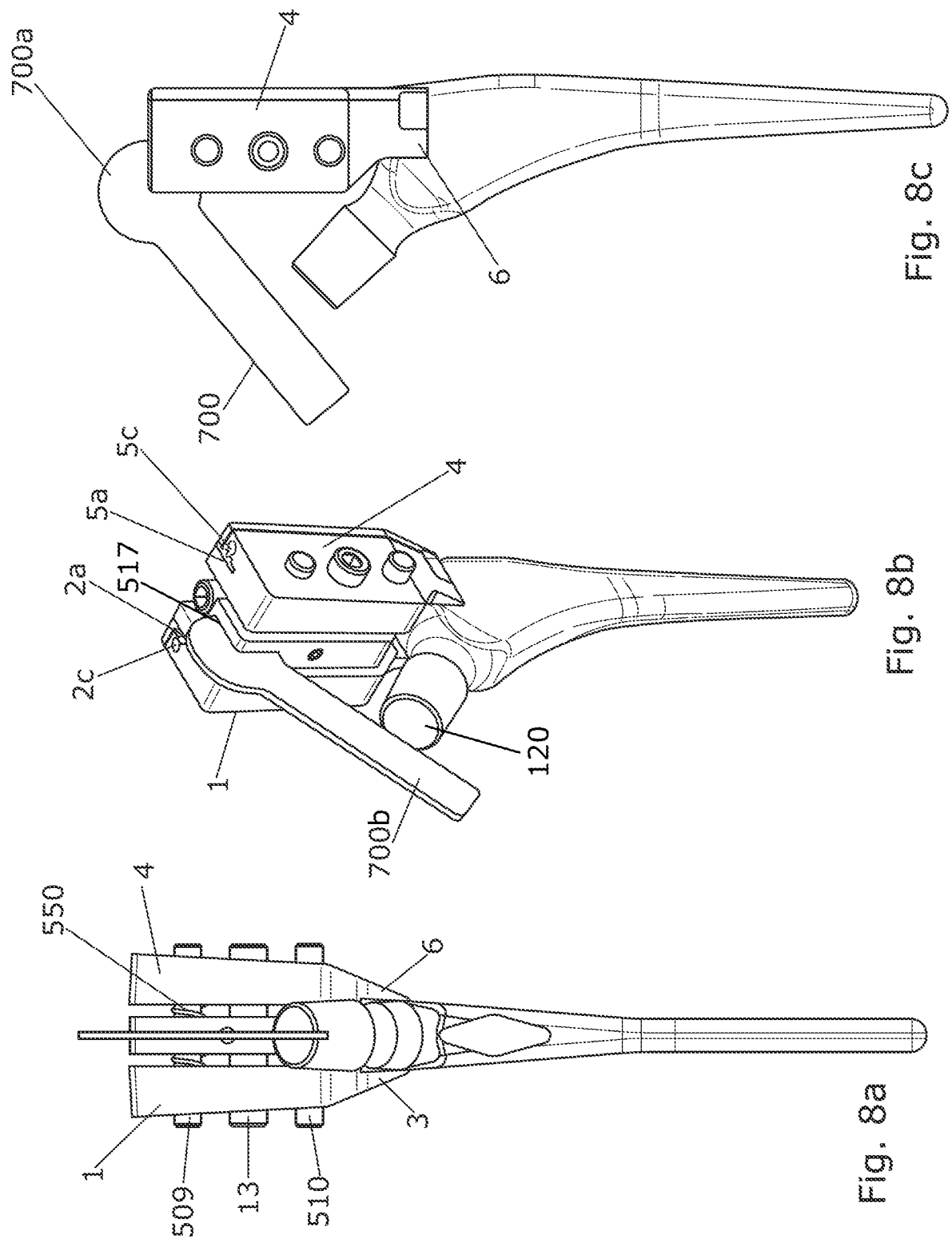

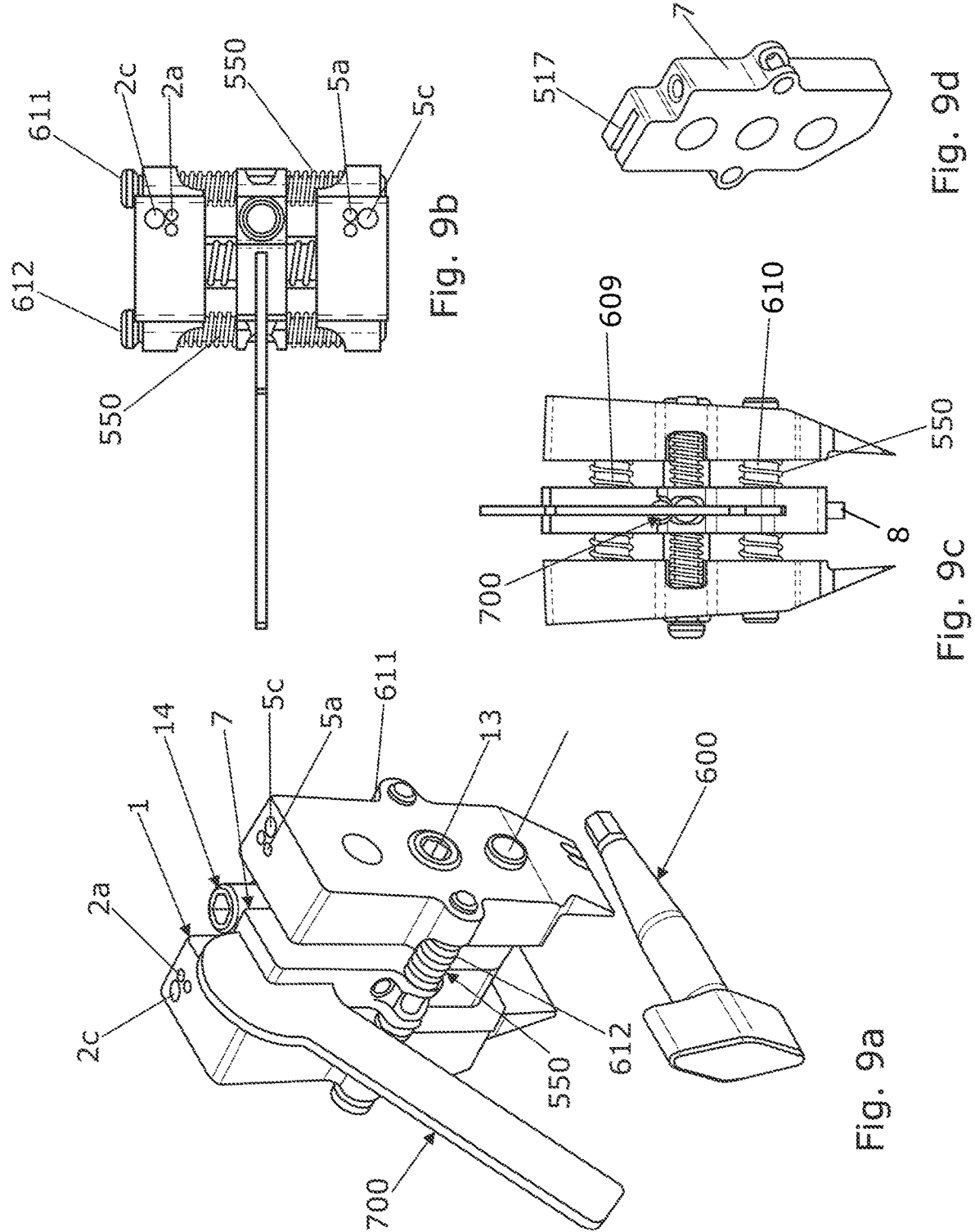

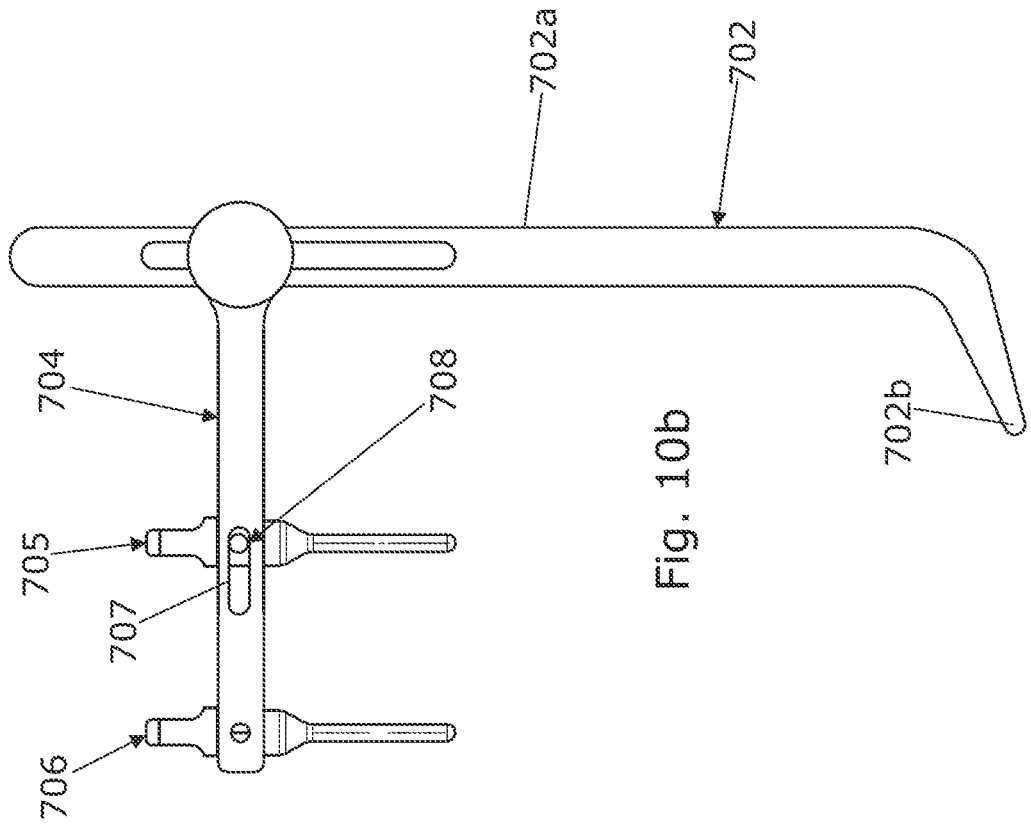
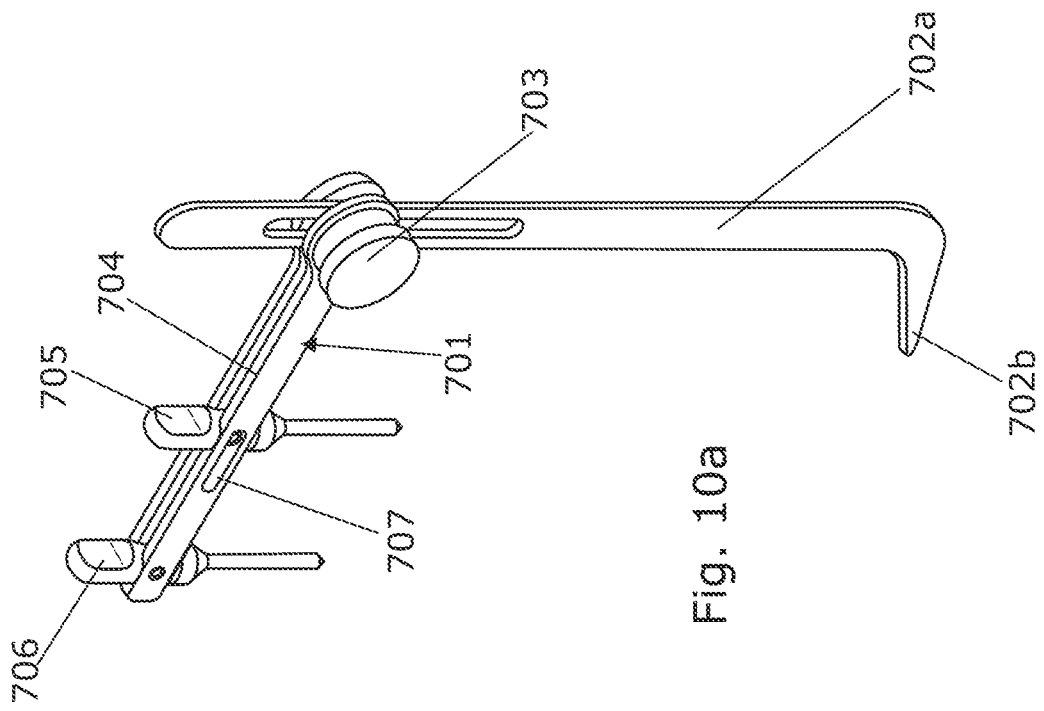

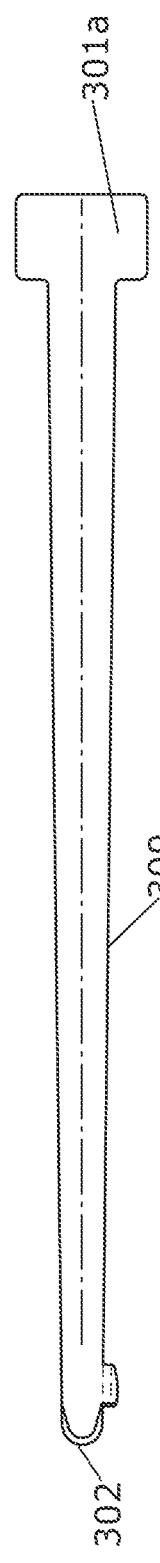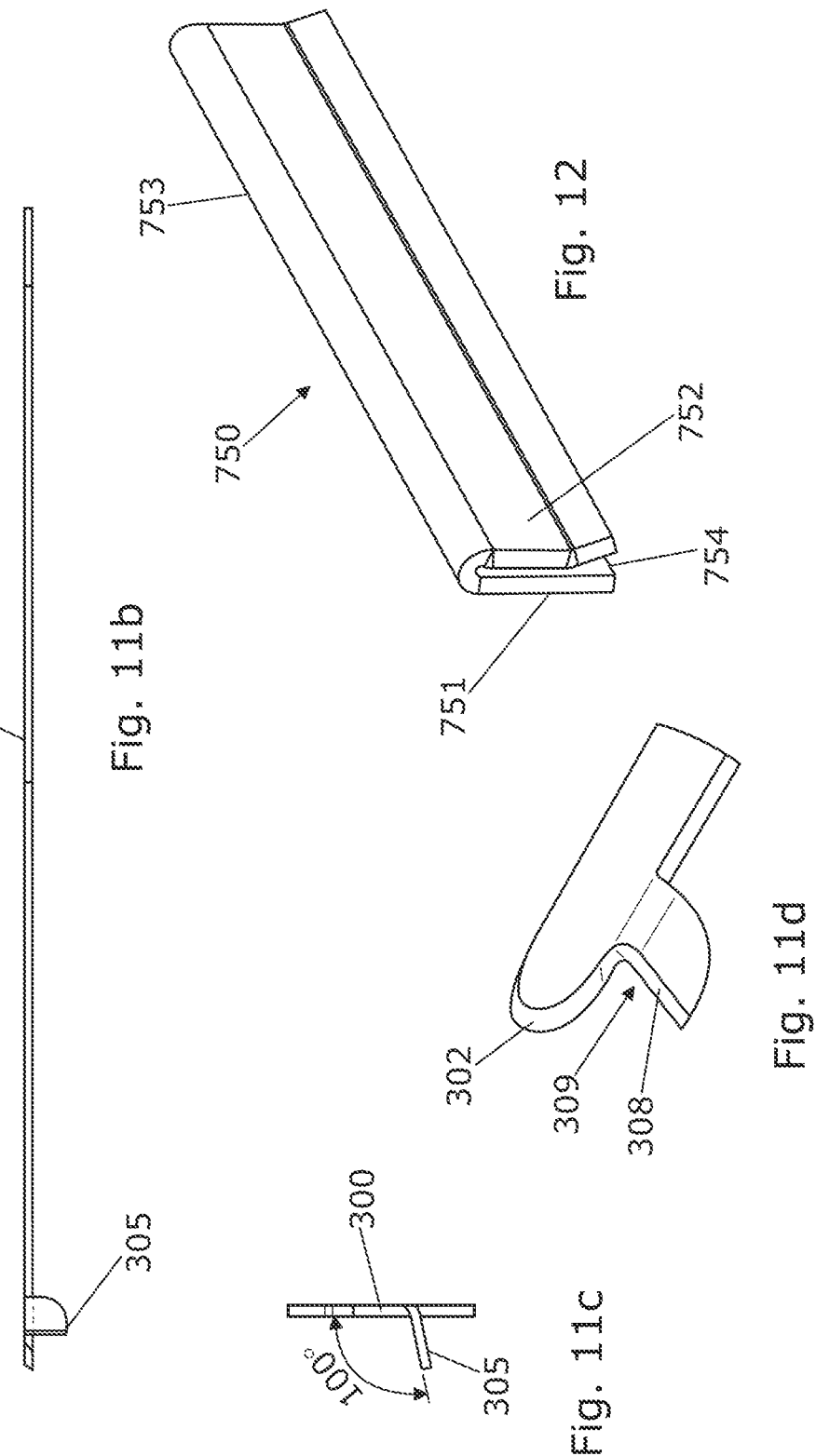

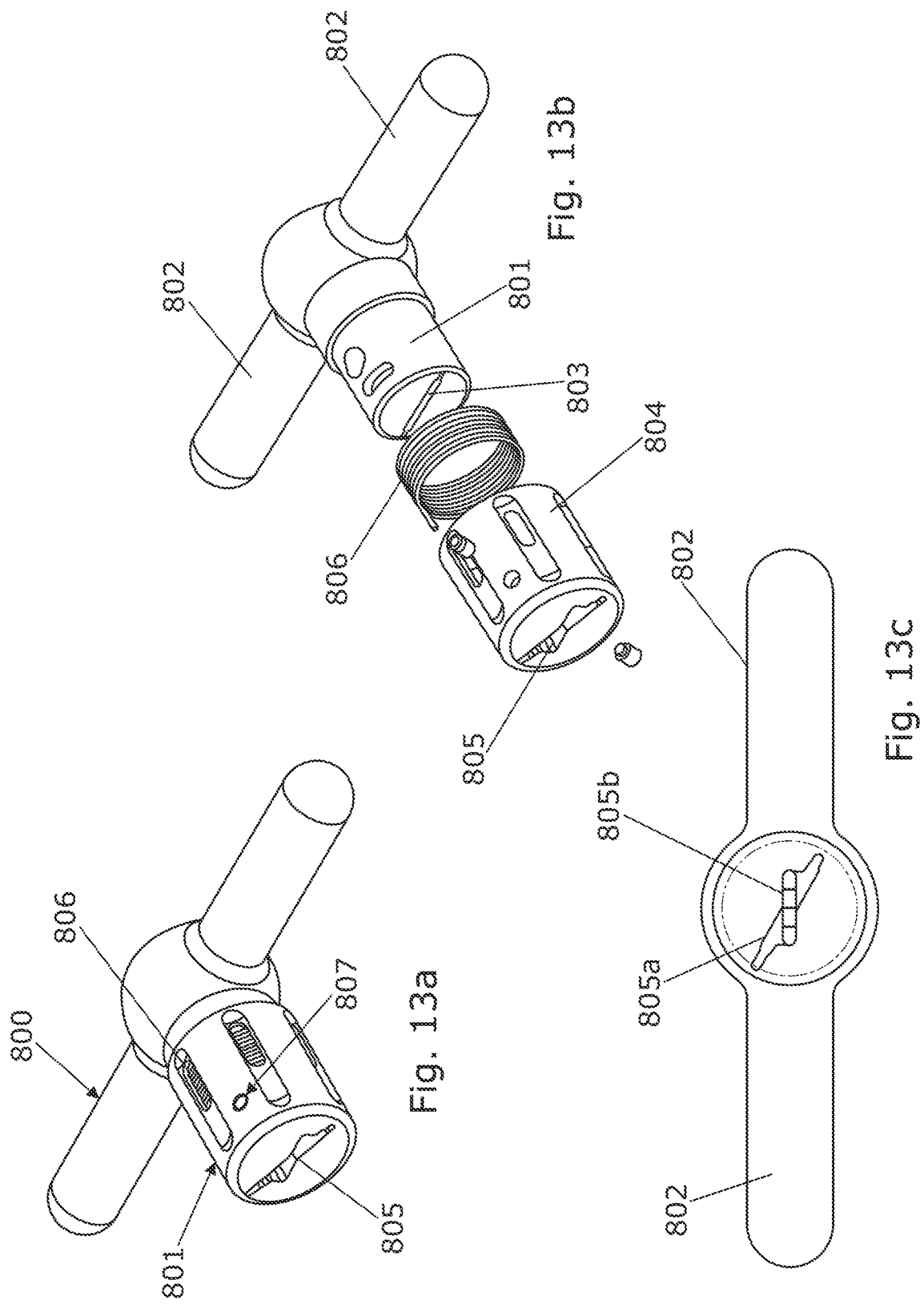

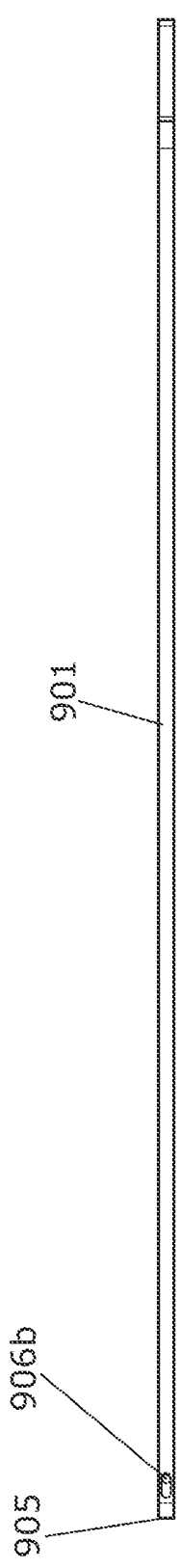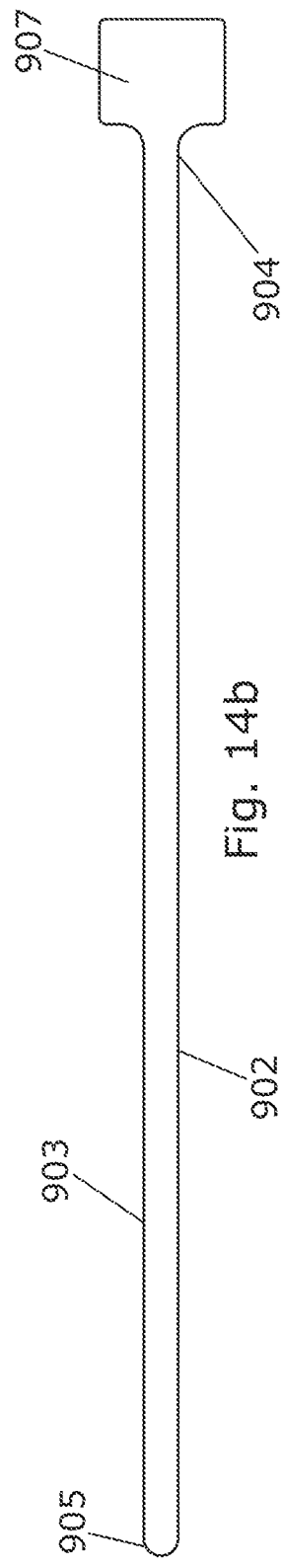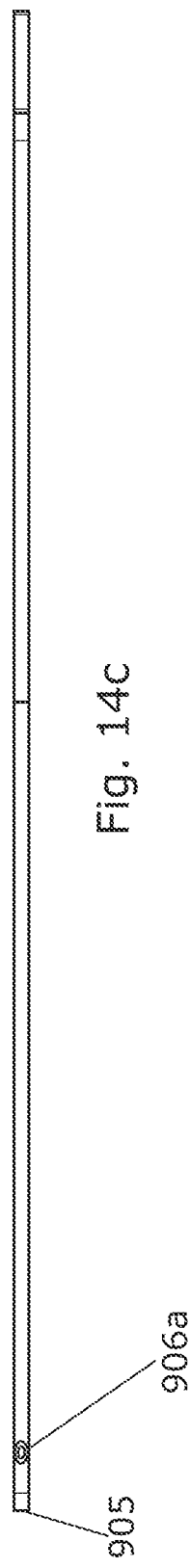
Fig. 14a
Fig. 14b
Fig. 14c

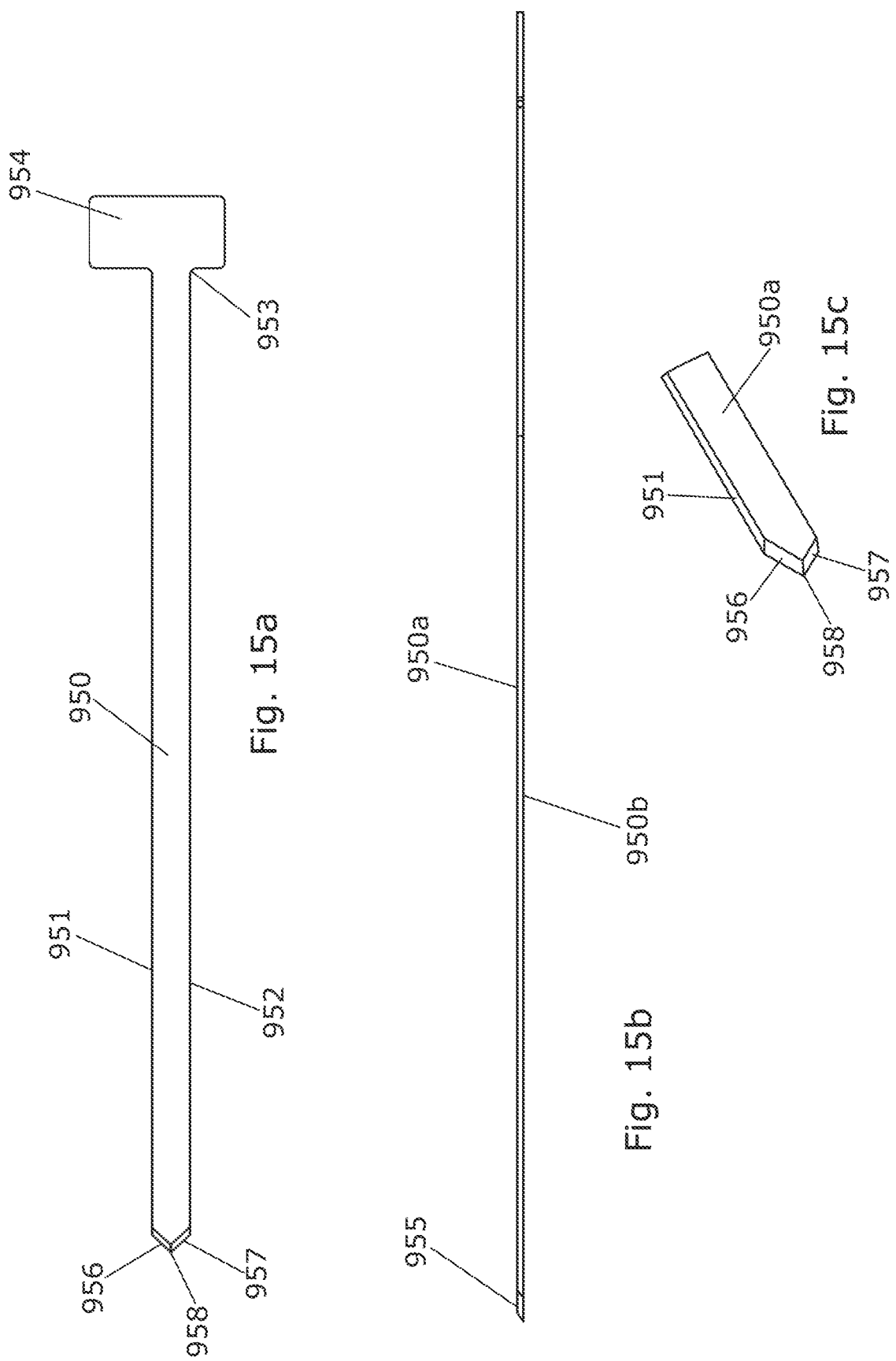

APPARATUS FOR USE IN SURGERY

RELATED APPLICATIONS

The present application is a 35 U.S.C. § 371 national phase application of PCT International Application No. PCT/GB2019/051450, filed May 28, 2019, which claims priority from U.S. Provisional Patent Application No. 62/676,469, filed May 25, 2018, the disclosures of which are hereby incorporated herein by reference in their entirety.

This invention relates to methods of removing implants embedded in surrounding tissue material and to associated apparatus for use in removing implants. More particularly, this invention relates to methods and apparatus for removing implants, such as femoral implants, from surrounding tissue material, e.g. in a human or animal body.

DESCRIPTION OF THE PRIOR ART

It is often necessary to remove implants that have previously been inserted, for example, where the implant has become loose, or the tissue surrounding the implant is infected. The failure rate of femoral implants, necessitating removal and insertion of a new implant, is believed to be about 10%.

Implants may generally be cemented or uncemented into position. For uncemented implants bony ingrowth is encouraged, which serves to secure the implant. Fibrous tissue may grow and encapsulate the implant.

A disadvantage of many known approaches is that to remove the implant any cement and bony ingrowth around the implant needs to be removed. In practice this results in large amounts of surrounding tissue (e.g. bone) being taken out, with a significantly larger cavity being left behind. The surgery is therefore relatively invasive and more expensive. In addition, the recovery from the surgery takes longer, and the patient cannot load bear through the new implant for some time after the surgery.

Common approaches to removing implants involve the use of standard osteotome devices.

The present invention provides an approach, and associated apparatus, to remove uncemented implants that have previously been inserted in a human or animal body.

SUMMARY OF THE INVENTION

The present invention permits an implant, especially a femoral implant, to be more readily removed from the surrounding tissue and with significantly less loss of tissue around the implant. The procedure is less invasive and generally will involve loss of tissue around the implant of the order of about 0.6 mm-1 mm, or even only about 0.6 mm, or even less, in each direction.

As the skilled reader will appreciate, a femoral implant has a tapered body. This extends from a broader proximal end, which provides a shoulder portion, to a narrower distal end. A neck extends from the proximal end, and a head extends from the neck.

The procedure generally involves firstly creating two access tunnels in the surrounding tissue, one at the anterior of the implant and one at the posterior of the implant, with each access tunnel extending from an access point at the proximal surface of the surrounding tissue, which can be accessed by a person carrying out the procedure, to a point in the surrounding tissue that is located beyond the distal end of the implant (e.g. at a distance of about 0.3 to 1.2 cm beyond the distal end, and preferably 0.5 to 1 cm beyond the distal end). The anterior access tunnel is spaced from and substantially parallel to the anterior surface of the implant and the posterior access tunnel is spaced from and substantially parallel to the posterior surface of the implant.

The anterior access tunnel is preferably spaced from the anterior surface of the implant by a distance of from 0.1 to 10 mm, such as from 0.1 to 8 mm or from 0.1 to 6 mm; in one preferred embodiment the distance is less than 5 mm, preferably less than 4 mm, or less than 3 mm, or less than 2 mm, such as from 0.1 to 2 mm. Most preferably the distance is less than 1 mm, such as from 0.3 mm to 1 mm and especially such as from 0.5 to 1 mm (preferably 0.5 mm).

The posterior access tunnel is preferably spaced from the posterior surface of the implant by a distance of from 0.1 to 10 mm, such as from 0.1 to 8 mm or from 0.1 to 6 mm; in one preferred embodiment the distance is less than 5 mm, preferably less than 4 mm, or less than 3 mm, or less than 2 mm, such as from 0.1 to 2 mm. Most preferably the distance is less than 1 mm, such as from 0.3 mm to 1 mm and especially such as from 0.5 to 1 mm (preferably 0.5 mm).

The access tunnels may be any shape in cross section, provided they are elongate. It will be appreciated that their dimension that extends substantially perpendicular to the anterior surface or the posterior surface should be relatively small, so as to minimise unnecessary removal of surrounding tissue, e.g. from 0.5 mm to 5 mm. However, their dimension that extends substantially parallel to the anterior surface or the posterior surface can be larger, if desired, because the method is seeking to create a space that extends over the width of the anterior surface and the posterior surface of the implant. Therefore this dimension can be larger than 5 mm without leading to unnecessary removal of surrounding tissue.

The access tunnels may be elongate bores with round cross sections, e.g. substantially circular cross sections. The diameter of the access tunnels may suitably be from 0.5 mm to 5 mm, preferably from 1 mm to 4 mm, e.g. from 2 mm to 4 mm or from 2.5 mm to 3.5 mm.

However, other cross sectional shapes can be envisaged for the access tunnels. The cross section may be a regular shape, i.e. where the sides are all equal in length, and therefore, for example, the access tunnels may be elongate with square or hexagonal or octagonal cross sections. The cross section may alternatively be an irregular shape, i.e. where the sides are not all equal in length, and therefore, for example, the access tunnels may be elongate with rectangular cross sections. The dimension that extends substantially perpendicular to the anterior surface or the posterior surface may suitably be from 0.5 mm to 5 mm, preferably from 1 mm to 4 mm, e.g. from 2 mm to 4 mm or from 2.5 mm to 3.5 mm. Thus the minimum diameter of the access tunnels (i.e. the smallest distance, when considered as a straight line, from one point on the perimeter to another point on the perimeter via the centrepoint) should fall within this range.

It is in particular envisaged that the access tunnels may be circular, square or rectangular in cross section.

There may be just one anterior access tunnel and just one posterior access tunnel. However, it is also envisaged that there could be more than one anterior access tunnel and/or more than one posterior access tunnel. In one embodiment, there may be two or more anterior access tunnels and/or two or more posterior access tunnels. In one embodiment, for example, there may be one, two or three anterior access tunnels and one, two or three posterior access tunnels.

The skilled reader will appreciate that in order to make the procedure as minimally invasive as possible, the tunnel as formed should have a dimension that extends substantially perpendicular to the anterior surface or the posterior surface that is as small as possible. However, there is also a desire to remove as much material as possible in a direction substantially parallel to the anterior surface or the posterior surface, to make subsequent steps easier. Therefore the use of two or more tunnels parallel to one another on the anterior surface and/or the posterior surface can be beneficial, because these can each have smaller diameters, and therefore minimise the intrusion into surrounding tissue, but overall these combine to remove more material in a direction substantially parallel to the anterior surface or the posterior surface.

For essentially the same reasons, the use of an access tunnel that has an elongate rather than a circular cross section can be beneficial. In this regard, the cross section should be such that the smallest dimension is in the direction that extends substantially perpendicular to the anterior surface or the posterior surface, whilst the largest direction is in the direction that extends substantially parallel to the anterior surface or the posterior surface. The access tunnel can, for example, have a rectangular shaped cross section.

This first step of the procedure is suitably effected using a targeting device, which ensures the access tunnels are created at the required locations on the anterior and posterior of the implant. It will be appreciated that the angle of the tunnels is important, because it is desired that the tunnels run all the way along the implant and converge at a location beyond the distal end of the implant.

The access tunnels may be created using conventional tools, such as a drill and drill bits, or a chisel, or a reciprocating saw, or a K-wire. Of course, the tool used could be bespoke instead. The key feature is that the tool is elongate and has at least one edge that is sufficiently sharp that when the tool is operated it can be used to create access tunnels on the anterior and posterior of the implant.

The targeting device may, in one embodiment, be a drill guide of the type described in WO2011/045568. Such a drill guide is suitably secured on a projection of a femoral implant.

The targeting device may, in another embodiment, be a targeting kit of the type described in WO2017/032993, the content of which is incorporated in its entirety by reference. Such a targeting kit is suitably secured on the head or neck of a femoral implant. If such as targeting kit is used, the first and second guide members may have bores that have any shape cross section, but in particular may have a circular cross section, a square cross section or a rectangular cross section.

However, in a preferred embodiment, the targeting device is a novel targeting device according to the invention as claimed, which is suitable for being secured on the shoulder of a femoral implant. As the skilled person will appreciate, it is standard for the shoulder of a femoral implant to have a recess portion, which may optionally have female screw threads provided inside. This recess is provided in implants as standard so that the distal end of an impactor can engage (e.g. by threaded engagement) into the recess to push and impact the femoral implant into the pre-prepared proximal part of the patient's femur, to the correct depth.

The targeting device of the present claimed invention makes use of this recess portion to engage with the femoral implant.

The recess portion will be located centrally, such that a vertical axis running from the midpoint of the recess to the distal tip of the implant is the central axis of the implant.

The recess portion is therefore on the medial lateral axis of the shoulder of the implant.

The inventor has determined that the convergence angle between the anterior surface and the posterior surface of an implant does not vary significantly from implant to implant. The angle found in most commercial implants is in the range of from 2 to 4 degrees. Therefore the inventor has determined that it would be possible to have a single universal targeting device with a fixed angle that can be utilised for a large number of implants that have a convergence angle the same as or smaller than the fixed angle.

Equally, it would be possible to have a kit of two or more universal targeting devices, each with a different fixed angle. The kit can be utilised for a large number of implants that have a convergence angle the same as or smaller than any one of the fixed angles provided by the devices.

The targeting device of the invention comprises:
- an anterior guide member, which comprises a first elongate body provided with a first angled channel therein, running from an entrance at the proximal end of the guide member to an exit at the distal end of the guide member, and where the first elongate body has a first contact element at its distal end for contacting the anterior surface of the shoulder of the femoral implant and for distancing the exit from the anterior surface of the shoulder of the implant,
- a posterior guide member, which comprises a second elongate body provided with a second angled channel therein, running from an entrance at the proximal end of the guide member to an exit at the distal end of the guide member, and where the second elongate body has a second contact element at its distal end for contacting the posterior surface of the shoulder of the implant and for distancing the exit from the posterior surface of the shoulder of the implant,
- an engagement member for locating and engaging the targeting device on the shoulder of the implant, which comprises a third elongate body with an engagement protrusion at its distal end, whereby the engagement protrusion can be received in a recess portion on the shoulder of the implant, and whereby the third elongate body can be located between and aligned with the first elongate body and the second elongate body, such that the elongate axes of the first, second and third elongate bodies are substantially aligned, and with the first and second angled channels converging in the direction of the distal end,
- a first pair of parallel connector rails, wherein each connector rail can slideably connect the anterior guide member and the posterior guide member via the engagement member, with the connector rails being received in connection bores in the anterior guide member and the posterior guide member,
- an adjustment system which can adjust the distance between the first elongate body and the third elongate body, so as to move the anterior guide member between a release position and a holding position, and which can adjust the distance between the second elongate body and the third elongate body, so to move the posterior guide member between a release position and a holding position;
- wherein when the anterior guide member and the posterior guide member are connected by the first pair of connector rails, via the engagement member, the elongate axes of the elongate bodies are substantially aligned and the angled channels converge in the direction of the distal end, with the convergence angle of the angled channels being in the range of from 2 to 6 degrees, such as from 2 to 5 degrees, such that the engagement protrusion can be located in a recess portion on the shoulder of the implant, with the anterior guide member and the posterior guide member in their release positions, and then the adjustment system can be used to move the anterior guide member towards its holding position until the first contact element contacts the shoulder of the implant, with the exit of the first angled channel lying spaced from the anterior surface of the implant, and to move the posterior guide member towards its holding position until the second contact element contacts the shoulder of the implant, with the exit of the second angled channel lying spaced from the posterior surface of the implant.

It may be that the first pair of parallel connector rails comprises one proximal rail and one distal rail. In one embodiment, there is a pair of parallel connector rails which comprises one proximal rail and one distal rail, where these rails are located at or near the midpoint between the medial face of the guide members and the lateral face of the guide members.

Alternatively, it may be that the first pair of parallel connector rails comprises one medial rail and one lateral rail. In one embodiment, there is a pair of parallel connector rails which comprises one medial rail and one lateral rail, where these rails are located at or near the midpoint between the proximal end of the guide members and the distal end of the guide members.

In one embodiment, the targeting device of the invention comprises:

an anterior guide member, which comprises a first elongate body provided with a first angled channel therein, running from an entrance at the proximal end of the guide member to an exit at the distal end of the guide member, and where the first elongate body has a first contact element at its distal end for contacting the anterior surface of the shoulder of the femoral implant and for distancing the exit from the anterior surface of the shoulder of the implant, a posterior guide member, which comprises a second elongate body provided with a second angled channel therein, running from an entrance at the proximal end of the guide member to an exit at the distal end of the guide member, and where the second elongate body has a second contact element at its distal end for contacting the posterior surface of the shoulder of the implant and for distancing the exit from the posterior surface of the shoulder of the implant, an engagement member for locating and engaging the targeting device on the shoulder of the implant, which comprises a third elongate body with an engagement protrusion at its distal end, whereby the engagement protrusion can be received in a recess portion on the shoulder of the implant, and whereby the third elongate body can be located between and aligned with the first elongate body and the second elongate body, such that the elongate axes of the first, second and third elongate bodies are substantially aligned, and with the first and second angled channels converging in the direction of the distal end, a first pair of parallel connector rails, wherein each connector rail can slideably connect the anterior guide member and the posterior guide member via the engagement member, with the connector rails being received in connection bores in the anterior guide member and the posterior guide member, a second pair of parallel connector rails, wherein each connector rail can slideably connect the anterior guide member and the posterior guide member via the engagement member, with the connector rails being received in connection bores in the anterior guide member and the posterior guide member, an adjustment system which can adjust the distance between the first elongate body and the third elongate body, so as to move the anterior guide member between a release position and a holding position, and which can adjust the distance between the second elongate body and the third elongate body, so to move the posterior guide member between a release position and a holding position;

wherein when the anterior guide member and the posterior guide member are connected by the first pair of connector rails and the second pair of connector rails, via the engagement member, the elongate axes of the elongate bodies are substantially aligned and the angled channels converge in the direction of the distal end, with the convergence angle of the angled channels being in the range of from 2 to 6 degrees, such as from 2 to 5 degrees, such that the engagement protrusion can be located in a recess portion on the shoulder of the implant, with the anterior guide member and the posterior guide member in their release positions, and then the adjustment system can be used to move the anterior guide member towards its holding position until the first contact element contacts the shoulder of the implant, with the exit of the first angled channel lying spaced from the anterior surface of the implant, and to move the posterior guide member towards its holding position until the second contact element contacts the shoulder of the implant, with the exit of the second angled channel lying spaced from the posterior surface of the implant.

In some embodiments the use of two pairs of parallel connector rails can be beneficial in terms of ensuring good alignment and stability.

In one embodiment, the first pair of parallel connector rails comprises one proximal rail and one distal rail and the second pair of parallel connector rails comprises one medial rail and one lateral rail.

It may be that the first pair of parallel connector rails comprises one proximal rail and one distal rail, where these rails are located at or near the midpoint between the medial face of the guide members and the lateral face of the guide members, and the second pair of parallel connector rails comprises one medial rail and one lateral rail, where these rails are located at or near the midpoint between the proximal end of the guide members and the distal end of the guide members.

In another embodiment, the first pair of parallel connector rails is a pair of parallel proximal connector rails, and the second pair of parallel connector rails is pair of distal connector rails.

It may be that the first pair of parallel connector rails comprises one medial rail and one lateral rail, where these rails are located at or near the proximal end of the guide members, and the second pair of parallel connector rails comprises one medial rail and one lateral rail, where these rails are located at or near the distal end of the guide members.

In one embodiment, the targeting device of the invention comprises:
- an anterior guide member, which comprises a first elongate body provided with a first angled channel therein, running from an entrance at the proximal end of the guide member to an exit at the distal end of the guide member, and where the first elongate body has a first contact element at its distal end for contacting the anterior surface of the shoulder of the femoral implant and for distancing the exit from the anterior surface of the shoulder of the implant,
- a posterior guide member, which comprises a second elongate body provided with a second angled channel therein, running from an entrance at the proximal end of the guide member to an exit at the distal end of the guide member, and where the second elongate body has a second contact element at its distal end for contacting the posterior surface of the shoulder of the implant and for distancing the exit from the posterior surface of the shoulder of the implant,
- an engagement member for locating and engaging the targeting device on the shoulder of the implant, which comprises a third elongate body with an engagement protrusion at its distal end, whereby the engagement protrusion can be received in a recess portion on the shoulder of the implant, and whereby the third elongate body can be located between and aligned with the first elongate body and the second elongate body, such that the elongate axes of the first, second and third elongate bodies are substantially aligned, and with the first and second angled channels converging in the direction of the distal end,
- a pair of parallel proximal connector rails, wherein each proximal connector rail can slideably connect the anterior guide member and the posterior guide member via the engagement member, with the connector rails being received in proximal connection bores in the anterior guide member and the posterior guide member,
- a pair of parallel distal connector rails, wherein each distal connector rail can slideably connect the anterior guide member and the posterior guide member via the engagement member, with the connector rails being received in distal connection bores in the anterior guide member and the posterior guide member,
- an adjustment system which can adjust the distance between the first elongate body and the third elongate body, so as to move the anterior guide member between a release position and a holding position, and which can adjust the distance between the second elongate body and the third elongate body, so to move the posterior guide member between a release position and a holding position;
- wherein when the anterior guide member and the posterior guide member are connected by the pair of proximal connector rails and the pair of distal connector rails, via the engagement member, the elongate axes of the elongate bodies are substantially aligned and the angled channels converge in the direction of the distal end, with the convergence angle of the angled channels being in the range of from 2 to 6 degrees, such as from 2 to 5 degrees,
- such that the engagement protrusion can be located in a recess portion on the shoulder of the implant, with the anterior guide member and the posterior guide member in their release positions, and then the adjustment system can be used to move the anterior guide member towards its holding position until the first contact element contacts the shoulder of the implant, with the exit of the first angled channel lying spaced from the anterior surface of the implant, and to move the posterior guide member towards its holding position until the second contact element contacts the shoulder of the implant, with the exit of the second angled channel lying spaced from the posterior surface of the implant.

When the targeting device is secured on the shoulder of the implant by the engagement of the engagement protrusion, the first contact element and the second contact element with the shoulder of the implant, access tunnels can be created anteriorly and posteriorly by use of a cutting tool being guided down the angled channels.

The method may suitably involve steps as follows.

A section of the body of the implant is exposed on the anterior surface of the implant and a section of the body of the implant is exposed on the posterior surface of the implant (e.g. a section having a length of from 0.5 to 5 cm, such as from 1 to 3 cm, or from 0.5 to 2 cm, on each surface may be exposed).

The location of the distal end of the implant is determined via x-ray. This can be carried out at this stage of the procedure, or may have been determined in advance.

The engagement protrusion is located in the recess portion on the shoulder of the implant. In one embodiment the engagement protrusion has male screw threads and can therefore be screwed into the recess portion if the recess portion has female screw threads. In another embodiment the engagement protrusion is received within and engages with the recess portion due to being substantially the same size in at least one dimension. In another embodiment the engagement protrusion is press-fitted into the recess portion.

The anterior guide member and the posterior guide member are initially in their release positions. This means that the first contact element is spaced from the anterior surface of the shoulder of the implant, and the second contact element is spaced from the posterior surface of the shoulder of the implant.

The adjustment system can be used to move the anterior guide member towards its holding position until the first contact element contacts the anterior surface of the shoulder of the implant. In this position the exit of the first angled channel lies spaced from the anterior surface of the implant.

The adjustment system can also be used to move the posterior guide member towards its holding position until the second contact element contacts the posterior surface of the shoulder of the implant. In this position the exit of the second angled channel lies spaced from the posterior surface of the implant.

It will be appreciated that the movement of the anterior guide member and the movement of the posterior guide member can occur in either order, or can be carried out simultaneously. In a preferred embodiment, the adjustment system is used to carry out the movement of the anterior guide member and the movement of the posterior guide member at the same time.

Thus in the present invention the anterior and posterior guide members can move simultaneously towards and away from the central engagement member.

The adjustment system may be any system that permits controlled linear movement of the anterior guide member and of the posterior guide member between two positions. Systems based on a threaded mechanism are in particular envisaged.

In particular, it is preferred that the adjustment system comprises a double ended screw, also known as a left- and right-screw. As the skilled reader will appreciate, such a screw has a first end portion with a right-hand screw thread and a second end portion with a left-hand screw thread, and a non-threaded section in the middle, between the two threaded end portions.

The double ended screw can be received in a first engaging bore in the anterior guide member, a second engaging bore in the posterior guide member and a non-engaging bore in the engagement member. It will be appreciated that this series of bores will, in use, be aligned, so that the double ended screw can be received in, and extend through, each of these bores. This series of bores is parallel to the connection bores. Therefore in use the anterior guide member, the engagement member and posterior guide member are connected and aligned using the connector rails and the double ended screw.

The double ended screw does not engage with the non-engaging bore in the engagement member. The non-threaded section in the middle of the double ended screw will be located in the non-engaging bore. Therefore the double ended screw extends through the engagement member but is not attached to the engagement member.

Suitably, the non-threaded section of the double ended screw is secured to the engagement member such that it cannot move the engagement member anteriorly or posteriorly but it can rotate within the engagement member.

The double ended screw does engage with the engaging bore in the posterior guide member and does engage with the engaging bore in the anterior guide member. The threaded portions at the two ends of the double ended screw are received in and engage with the engaging bore in the anterior guide member and the engaging bore in the posterior guide member. Therefore in use the double ended screw is attached to the anterior guide member and to the posterior guide member.

It may be that the right hand screw thread is provided in the anterior guide member and the left hand screw thread in the posterior guide member, and the invention will be further described in terms of this arrangement. However, it will be appreciated that the reverse configuration, with the right hand screw thread being provided in the posterior guide member and the left hand screw thread being provided in the anterior guide member, could also be used.

In use, when the screw is turned clockwise, from the anterior approach, the anterior and posterior members will each simultaneously move towards the engagement member, i.e. towards the holding positions. It will be appreciated that their movements will approximate one another and they will remain equidistant from the engagement member. Once the screw is fully tightened, the first and second contact elements will contact the shoulder of the implant, anteriorly and posteriorly. The device will therefore be secured to the shoulder. Anticlockwise rotation of the screw anteriorly will result in movement of the anterior and posterior member away from the engagement member, i.e. towards the release positions, and so will release the device from the shoulder of the implant.

The converse is true in relation to the turning of the screw from the posterior approach. Anticlockwise rotation of the screw will simultaneously move the anterior and posterior members towards the engagement member, i.e. towards the holding positions. When fully tightened anticlockwise, the holding position is reached and the device is secured on the implant shoulder. Meanwhile, when the screw is turned clockwise from the posterior approach it will result in the anterior and posterior members moving away from the engagement member, i.e. towards the release positions, and so will release the device from the shoulder of the implant.

When using the device of the invention, it will be appreciated that the engagement protrusion ensures central alignment, and the contact elements ensure that the device is securely positioned and that the exits of the channels are spaced away from the anterior and posterior surfaces of the implant, and the fixed angles of the angled channels ensure that the angled channels converge towards the distal tip of the implant.

The targeting device will then have its components arranged in the required orientation. The angled channels are pointing towards the central axis of the implant.

The fixed angles of the angled channels are such that they converge at a convergence angle of from 2 to 6 degrees, preferably from 2 to 5 degrees, e.g. from 3 to 5 degrees or from 4 to 5 degrees, and most preferably 4 degrees, because this then provides good alignment for most implants.

Where reference is made to the convergence angle of the angled channels, this is the angle between the channels when the anterior guide member and the posterior guide member are both in their holding positions.

Preferably the arrangement of the angled channels is symmetrical. Therefore in one embodiment each angled channel has a fixed angle with reference to the elongate axis of the elongate body in which it is provided that is in the range of from 1 to 3 degrees, such as from 1 to 2.5 degrees, e.g. 2 degrees.

In practice, it may be found that the angle between the angled channels when the targeting kit has been secured to the implant (i.e. when the anterior guide member is in its holding position and the posterior guide member is in its holding position) is less than the sum of the fixed angles of the two angled channels. For example, about 0.5 to 1 degree of angle may be lost from each angled channel due to the tightening action of moving the guide members into their holding positions.

Therefore it may be that each of the angled channels has a fixed angle with reference to the elongate axis of the elongate body in which it is provided that is in the range of from 2 to 3 degrees, such as from 2.5 to 3 degrees. It may, for example, be that using angled channels each with a 3 degree angle results in a convergence angle of the angled channels when the targeting kit has been secured to the implant of from 4 to 5 degrees.

In one embodiment, the targeting device may be provided together with a key that can be used to operate the adjustment system. For example, the key may engage with and rotate the adjustment system. In one embodiment, the key has a proximal end that is a male engaging portion which engages with a corresponding female receiving portion on the adjustment system.

The targeting device may be used in combination with a medial targeting device. This device can be used to double check the alignment of the targeting kit in the antero-posterior plane before the tunnels are drilled.

When a medial targeting device is used, the targeting device is provided with an alignment slot located at the proximal end of the engagement member. This alignment slot is in longitudinal alignment with the engagement protrusion of the engagement member.

The medial targeting device is in the form of a plate, which has an enlarged head at the proximal end and an elongate body that extends to the distal end. The enlarged head is sized and shaped to be received in the alignment slot of the engagement member. In one embodiment, the enlarged head is circular in shape. A curved shape assists with ease of use. The elongate body has a length greater than the distance from the alignment slot to the engagement protrusion of the engagement member. Therefore when the enlarged head is located in the alignment slot, the distal end of the medial targeting device can extend beyond the engagement protrusion of the engagement member.

In use, the enlarged head is received in the alignment slot of the engagement member and the elongate body of the medial targeting device is then pivoted until it contacts the proximal end of the neck of the femoral implant. An assessment can be made as to whether the elongate plate is bisecting the neck centrally in the antero-posterior plane. If it is not, the location of the targeting device can be adjusted until the elongate plate of the medial targeting device does bisect the neck centrally in the antero-posterior plane.

The targeting device may be used in combination with an external targeting device. This device can be used to double check the alignment of the targeting kit in the anterior-posterior plane before the tunnels are drilled.

In one embodiment, the external targeting device may comprise:
  a targeting device interlocking portion,
  an alignment portion, and
  a holding arrangement for holding and pivoting the alignment portion relative to the targeting device interlocking portion,
wherein the targeting device interlocking portion comprises a planar support body provided with:
  an anterior guide member interlocking component, which comprises a first locking pin that extends from the planar support body in the same plane and can be received in the first angled channel or a first receiving channel adjacent thereto and aligned therewith, and
  a posterior guide member interlocking component, which comprises a second locking pin that extends from the planar support body in the same plane and can be received in the second angled channel or a second receiving channel adjacent thereto and aligned therewith, wherein the alignment portion comprises a planar elongate body having an angled tip at the distal end,
and wherein the holding arrangement holds the planar elongate body and the planar support body in the same plane, but permits the pivotal movement of the planar elongate body relative to the planar support body within that plane,
  such that the first locking pin can be received in the first angled channel of the targeting device or a first receiving channel adjacent thereto and aligned therewith, and the second locking pin can be received in second angled channel of the targeting device or a second receiving channel adjacent thereto and aligned therewith,
  such that the planar support body is aligned with the anterior-posterior plane in which the first and second angled channels lie,
  and such that the planar elongate body is consequently also aligned with the anterior-posterior plane in which the first and second angled channels lie,
such that the planar elongate body can be pivoted relative to the planar support body until the angled tip is alongside the implant and the plane of the angled tip can be compared to the centreline in the anterior-posterior plane, as determined via x-ray.

In one embodiment, the targeting device includes a first receiving channel adjacent to the first angled channel and aligned therewith and includes a second receiving channel adjacent to the second angled channel and aligned therewith. The anterior guide member interlocking component and the posterior guide member interlocking component are then received in these channels respectively. In this embodiment the first and second receiving channels may, for example, be circular in cross section and may each have a diameter of from 2 to 4 mm, such as about 3 mm. However, other shapes could be envisaged, e.g. they could have a square cross section, and likewise other sizes could be envisaged. The first and second receiving channels may, for example, extend for a depth of 15 mm or more, such as 20 mm or more, or 25 mm or more. The first and second receiving channels may, for example, extend for a depth that is less than the depth of the targeting device, such as from 15 to 70 mm or from 20 to 60 mm, e.g. from 25 to 40 mm.

In an alternative embodiment, the anterior guide member interlocking component is received in the first angled channel and the posterior guide member interlocking component is received in the second angled channel.

If the plane of the angled tip is not aligned with the centreline in the anterior-posterior plane, the location of the targeting device can be adjusted until the angled tip does align with the centreline in the anterior-posterior plane.

A tool is then used to create the access tunnels anteriorly and posteriorly. The choice of tool will depend on the shape of the angled channels. The tool is moved down the angled channels and therefore creates angled tunnels spaced from but close to the anterior and posterior surfaces of the implant. Tools that may be used include, but are not limited to, a drill and drill bit, a chisel, a K-wire, and a saw (e.g. a reciprocating saw).

A benefit of using a chisel is that it has an angled face, and therefore it is possible to keep the cutting closer to the implant surface.

It may be that a chevron chisel according to the invention is used. A chevron chisel according to the invention comprises:
  an elongate body in the form of a flat plate having an upper face and a lower face, wherein the elongate body extends from a first elongate edge to a second elongate edge and having a proximal end that can be provided with a handle and having a distal end; and
  a cutting portion located at the distal end which comprises a first cutting face and a second cutting face which meet at an angled cutting point, wherein the first cutting face extends at an angle of from 30 to 60 degrees, e.g. from 40 to 50 degrees, from the first elongate edge when measured with respect to the elongate axis of the elongate body, and the second cutting face extends at an angle of from 30 to 60 degrees, e.g. from 40 to 50 degrees, from the second elongate edge when measured with respect to the elongate axis of the elongate body, and wherein the first cutting face extends at an angle of from 30 to 60 degrees, e.g. from 40 to 50 degrees, from the lower face to the upper face, and wherein the second cutting face extends at an angle of from 30 to 60 degrees, e.g. from 40 to 50 degrees, from the lower face to the upper face.

Preferably the angled cutting point is located substantially centrally between the first elongate edge and the second elongate edge.

The chevron chisel may optionally have a depth (the lower face to the upper face) of from 0.5 to 3 mm, e.g. 1 to 2 mm; it may be about 1 mm deep. The chevron chisel may optionally have a width (first elongate edge to a second elongate edge) of from 4 to 10 mm, e.g. 5 to 9 mm; it may be about 7 to 8 mm wide.

Optionally, more than one tool can be used. Therefore, for example, a drill and drill bit can firstly be used to drill a hole, and then a chisel (e.g. a chevron chisel) can be used. The use of a second tool permits the tunnels to be made larger in size.

If a second tool is used, this can be used while the targeting device is still in position, therefore meaning that the second tool can be guided by the angled channels. Alternatively, the targeting device can be removed before the second tool is used, with the tunnel as already formed by the first tool (e.g. a K wire) being used to guide the second tool (e.g. a chevron chisel).

In one embodiment, a tunnel (e.g. one or two tunnels anteriorly and one or two tunnels posteriorly) is created using a K-wire as the first tool and then a chisel is used as the second tool. In another embodiment, a tunnel (e.g. one tunnel anteriorly and one tunnel posteriorly) is created using a chisel or a saw as the only tool.

As a second step, the procedure involves removing bony ingrowth located adjacent to the anterior access tunnel, and removing bony ingrowth located adjacent to the posterior access tunnel and the posterior surface of the implant. The intention of this step is to extend the width of the access tunnels, preferably so that their widths substantially correspond with the width of the implant. Therefore the anterior access tunnel is broadened in a plane that is substantially parallel to the anterior surface of the implant, and the posterior access tunnel is broadened in a plane that is substantially parallel to the posterior surface of the implant.

This step is optional if the access tunnels are already sufficiently wide. So, for example, if the access tunnels are created using a device where the angled channels are slots with rectangular cross sections, the access tunnels may already extend over a desired width. For example, a saw or flat chisel may have been used to create the access tunnels in such an embodiment where the angled channels are slots with rectangular cross sections.

In one embodiment, the widths of the tunnels are already 50% or more of the respective widths of the implant surfaces, e.g. 60% or more or 70% or more or 80% or more. It may even be that the widths of the tunnels already substantially correspond with the respective widths of the implant surfaces. In such embodiments, the second step is optional.

Preferably the second step is carried out unless the widths of the tunnels are already 80% or more of the respective widths of the implant surfaces, e.g. 90% or more or 95% or more.

When the second step is carried out, this second step of the procedure is suitably effected using an osteotome device.

The osteotome device may be of the type described in WO2017/032993.

The osteotome device may, however, be a novel chevron osteotome device according to the invention. This device may also be described as a spear chisel.

The chevron osteotome device of the invention comprises:
an elongate body having a proximal end that can be provided with a handle and a distal end, wherein the elongate body includes a distal section extending from the distal end to a shoulder point, wherein the shoulder point is located closer to the distal end than the proximal end;
a cutting portion extending outwardly from both sides of the elongate body at the shoulder point, the cutting portion having a first angled cutting side that extends outwardly from one side of the elongate body at the shoulder point, and a second angled cutting side that extends outwardly from the opposite side of the elongate body at the shoulder point, wherein the cutting portion has a front face and a back face which are connected by the first angled cutting side and the second angled cutting side, the front face being aligned with and a continuation of the elongate body, and the back face being aligned with and a continuation of the elongate body, such that the cutting portion has the same depth as the elongate body, and wherein the front face and the back face are blunt;

such that the distal end of the chevron osteotome device can be located in an access tunnel and chevron osteotome device can be pushed in the direction of the distal end of the implant so as to cut away bony ingrowth on both sides of the access tunnel with the first angled cutting side and the second angled cutting side.

The chevron osteotome device of the invention is suitably of one-piece construction, for example it may be formed by laser cutting.

In one embodiment the chevron osteotome device of the invention is provided with a handle. In one embodiment the handle is an integral part of the device, for example the device plus handle may be a one-piece construction product. In another embodiment, the handle is removable. In one embodiment, the chevron osteotome is, in use, not attached to a handle but instead is attached to a reciprocating saw or another reciprocating mechanism that automatically moves the device forwards and backwards in a linear fashion.

The elongate body follows the access tunnel, whilst the cutting portion breaks the bone-implant interface on both sides of the access tunnel due to the cutting action of the first angled cutting side and the second angled cutting side.

It is preferred that more than one osteotome device is used in this stage. In particular, a plurality of osteotome devices may be provided, with each having a different width of cutting portion (maximum distance between the first cutting side and a second cutting side). Therefore a first osteotome device may be provided that is slightly wider than the width of the access tunnel (e.g. 0.5 mm wider or more, or 1 mm wider or more, such as from 1 mm to 5 mm wider) and this is pushed in the direction of the distal end of the implant so as to cut away bony ingrowth with the first cutting side and the second cutting side. Then a further osteotome device may be provided that is slightly wider than the width of the now-widened access tunnel (e.g. 0.5 mm wider or more, or 1 mm wider or more, such as from 1 mm to 5 mm wider) and this is pushed in the direction of the distal end of the implant so as to cut away bony ingrowth with the first cutting side and the second cutting side.

This step can be repeated as required for both tunnels until the anterior access tunnel has been widened as required in a direction parallel to the anterior surface of the implant and the posterior access tunnel has been widened as required in a direction parallel to the posterior surface of the implant, preferably so that the widths of the tunnels substantially correspond with the respective widths of the implant surfaces. The skilled reader will understand that the access tunnels may therefore end up not being of a consistent width following this stage, but rather may be wider at the access point than at the point in the surrounding tissue located beyond the distal end of the implant.

Thirdly, the procedure involves removing bony ingrowth located between the implant and the femur in the anterior aspect, and removing bony ingrowth located between the implant and the femur in the posterior aspect.

It will be appreciated that the use of the osteotomes clears a channel that has the shape corresponding to the osteotome cutting blade. The osteotome cutting blade will not extend so as to clear all bony ingrowth from between the implant and the femoral cortex medially and laterally. Instead, it will normally be the case that on both the anterior aspect and the posterior aspect there is bony ingrowth between the implant and the inner cortex of the femur medially and laterally.

Therefore the intention of this third step is to further extend the width of the access tunnels. In this regard, the amount of bony ingrowth between the implant and the femur in the anterior aspect is reduced. In addition, the amount of bony ingrowth between the implant and the femur in the posterior aspect is reduced.

Preferably the width of the access tunnels is increased so that their widths extend to the surface of the femoral cortex medially and laterally.

Therefore the anterior access tunnel is broadened in a plane that is substantially parallel to the anterior surface of the implant, but in the region between the implant and the inner cortex of the femur. This is in both medial and lateral directions. The posterior access tunnel is broadened in a plane that is substantially parallel to the posterior surface of the implant, but in the region between the implant and the inner cortex of the femur. This is in both medial and lateral directions.

Therefore this step clears a space at the bone-implant interface that extends, at least substantially, to both the medial and lateral edges of the implant.

This third step of the procedure is suitably effected using a curette device.

The curette device may be of the type described in WO2017/032993.

Preferably, the curette device is a novel curette device according to the invention.

The curette device of the invention comprises:
an elongate body in the form of a flat plate that extends from a first elongate edge to a second elongate edge and having a proximal end that can be provided with a handle and having a distal end;
a first cutting portion located at or near the distal end which extends outwardly from a first elongate edge of the elongate body, the cutting portion having a blunt edge and a cutting edge which meet at an angled cutting point, wherein the blunt edge extends from a first location on the elongate body to the cutting point and the cutting edge extends from a second location on the elongate body to the cutting point, wherein the first location is closer to the distal end than the second location and wherein the cutting edge is at an angle to the elongate axis of the curette device of from 50 to 85 degrees;
such that the curette device can be located in an access tunnel, with its elongate axis substantially aligned with the central axis running along the length of the tunnel, and with the distal end located at or near the distal (closed) end of the access tunnel, and then can be moved such that its elongate axis is angled with respect to the central axis running along the length of the tunnel, until at least the cutting point of the cutting edge contacts bony ingrowth located between the implant and the femoral cortex, and such that the curette device can then be withdrawn from the access tunnel whilst being retained in an angled position, such that as the device is withdrawn the cutting edge cuts away bony ingrowth located between the implant and the femoral cortex.

The curette device of the invention is suitably of one-piece construction, for example it may be formed by laser cutting.

In a preferred embodiment the curette device comprises a second cutting portion, located between the second elongate edge and the distal end of the elongate body. For example, a second cutting portion may be provided on a curved or angled edge that extends between the second elongate edge and the distal end of the elongate body. The second cutting portion suitably comprises teeth. Alternatively or additionally, the second cutting portion may comprise a sharp edge.

In one embodiment the curette device of the invention is provided with a handle. In one embodiment the handle is an integral part of the device, for example the device plus handle may be a one-piece construction product. In another embodiment, the handle is removable. Due to the nature of the third stage, it is preferred that the curette device is operated manually rather than using any automation, so that the surgeon can feel the required extent of bony ingrowth to be removed and not remove more bone than necessary.

The curette device is used in the anterior access tunnel, so that the tunnel is broadened in a plane that is substantially parallel to the anterior surface of the implant, but in the region between the implant and the inner cortex of the femur.

It will be appreciated that this process can be effected in both medial and lateral directions.

The curette device is also used in the posterior access tunnel, so that the tunnel is broadened in a plane that is substantially parallel to the posterior surface of the implant, but in the region between the implant and the inner cortex of the femur.

It will be appreciated that this process can be effected in both medial and lateral directions.

In each case, the device is sent down the access tunnel when substantially axially aligned with the tunnel, so that the cutting edge does not cut any surface as it is sent down the tunnel; then when the distal end of the device is located at or near the distal (closed) end of the access tunnel the device is angled, such that at least the cutting point of the cutting edge contacts the bony ingrowth, and then the device is withdrawn from the access tunnel whilst being retained in an angled position, such that as the device is withdrawn the cutting edge cuts away bony ingrowth.

In one embodiment the curette device is used more than once in each access tunnel in this stage. In this regard, it may be repeatedly sent down the access tunnel, then angled, and then withdrawn from the access tunnel whilst being retained in an angled position, such that as the device is withdrawn the cutting edge cuts away bony ingrowth. Each time the device is withdrawn the cutting edge is effectively scraping a layer of bony ingrowth, and so reduces the depth of bony ingrowth between the surface of the implant and the inner cortex of the femur. In one embodiment this is repeated until there is no bony ingrowth between the surface of the femoral implant and the femoral cortex.

It will be appreciated that this step can be repeated as required for both tunnels until the anterior access tunnel has been widened as required and the posterior access tunnel has been widened as required, preferably so that there is no bony ingrowth between the surface of the femoral implant and the femoral cortex in the posterior aspect and/or the anterior aspect.

In an optional next step, the procedure involves removing bony ingrowth located at the distal end of the implant, to create a cavity at the distal end of the implant that extends in the medial and lateral directions. Preferably the cavity also extends the available space at the distal end in the anterior and posterior directions. In one embodiment, the cavity extends beyond the medial surface of the implant, e.g. by 1 mm or more, such as from 2 mm to 1.5 cm, preferably from 3 mm to 1 cm. In one embodiment, the cavity extends beyond the lateral surface of the implant, e.g. by 1 mm or more, such as from 2 mm to 1.5 cm, preferably from 3 mm to 1 cm. In one embodiment, the cavity extends beyond the anterior surface of the implant, e.g. by 1 mm or more, such as from 2 mm to 1.5 cm, preferably from 3 mm to 1 cm. In one embodiment, the cavity extends beyond the posterior surface of the implant, e.g. by 1 mm or more, such as from 2 mm to 1.5 cm, preferably from 3 mm to 1 cm.

This optional step of the procedure is suitably effected using a distal space maker.

The distal space maker may be a medial-lateral cavity maker device of the type described in WO2017/032993.

However, this step is not essential and may be omitted.

In a fourth stage, the procedure involves removing bony ingrowth located at the antro-lateral edge of the implant, at the antro-medial edge of the implant, at the postro-lateral edge of the implant and at the postro-medial edge of the implant. The intention of this step is to remove bony ingrowth from sections of both the medial and lateral aspects of the implant.

As noted above, in the third stage the anterior access tunnel is broadened in a plane that is substantially parallel to the anterior surface of the implant, in both medial and lateral directions, and the posterior access tunnel is broadened in a plane that is substantially parallel to the posterior surface of the implant, in both medial and lateral directions. Therefore at both the anterior surface and the posterior surface there is a space at the bone-implant interface that extends, at least substantially, to the medial and lateral edges of the implant.

In the fourth stage the medial surface of the implant is cleared of bony ingrowth at or near to where it adjoins the anterior surface of the implant and at or near to where it adjoins the posterior surface of the implant. The lateral surface of the implant is cleared of bony ingrowth at or near to where it adjoins the anterior surface of the implant and at or near to where it adjoins the posterior surface of the implant.

This fourth stage of the procedure is suitably effected using a medial-lateral clearance device.

The medial-lateral clearance device may be a medial-lateral clearance device of the type described in WO2017/032993.

Preferably, the medial-lateral clearance device is a novel medial-lateral clearance device according to the invention.

The medial-lateral clearance device of the invention comprises:
- an elongate body having a proximal end that can be provided with a handle and having a distal end, the elongate body being in the shape of a flat plate that extends from a first elongate edge to a second elongate edge;
- a cutting portion extending outwardly from the elongate body and located at or near the distal end, the cutting portion having an inner surface that is flat and which connects with the first elongate edge of the elongate body at a substantially 90 degree angle, and having an outer surface that comprises an angled cutting face that is located towards the distal end of the elongate body, wherein the inner surface meets the angled cutting face at a cutting edge, at an angle of from 20 to 70 degrees;

such that the distal end of the flat plate elongate body can be located in a space at the bone-implant interface, at or near to the shoulder portion of the implant, with the flat plate being parallel to either the anterior surface or the posterior surface, and with the flat inner surface of the cutting portion aligned with either the medial or lateral surface of the implant, such that the medial-lateral clearance device can then be pushed in the direction of the distal end of the implant, with the flat plate elongate body remaining alongside the respective anterior or posterior surface, in the space at the bone-implant interface, whilst the angled cutting face cuts away bony ingrowth located at said medial or lateral surface of the implant as the device is pushed towards the distal end of the implant.

In one embodiment all of the outer surface is angled. In another embodiment, the outer surface comprises a flat portion as well as the angled cutting face. However, the angled cutting face must be located towards the distal end of the elongate body and must meet the inner surface towards the distal end of the elongate body, i.e. such that cutting occurs as the device is pushed towards the distal end of the implant. Therefore any flat portion of the outer surface is located towards the proximal end.

The skilled reader will appreciate that there is a "left handed" version of this device and a "right handed" version of this device. The difference is whether the inner surface of the cutting portion is ninety degrees clockwise from the flat plate elongate body or ninety degrees anticlockwise from the flat plate elongate body. To clear the medial surface of bony ingrowth at or near to where it adjoins the anterior surface of the implant and at or near to where it adjoins the posterior surface of the implant both versions of the device will be required. Equally, to clear the lateral surface of the implant of bony ingrowth at or near to where it adjoins the anterior surface of the implant and at or near to where it adjoins the posterior surface of the implant will require both versions of the device.

Therefore it is preferred that a medial-lateral clearance kit is provided that comprises a medial-lateral clearance device where the inner surface of the cutting portion is ninety degrees clockwise from the flat plate elongate body and a medial-lateral clearance device where the inner surface of the cutting portion is ninety degrees anticlockwise from the flat plate elongate body.

A first medial-lateral clearance device is used in the anterior access tunnel, so as to clear the medial surface of the implant of bony ingrowth at or near to where it adjoins the anterior surface of the implant. That medial-lateral clearance device is also used in the posterior access tunnel, so as to clear the lateral surface of the implant of bony ingrowth at or near to where it adjoins the posterior surface of the implant.

A second medial-lateral clearance device is used in the anterior access tunnel so as to clear the lateral surface of the implant of bony ingrowth at or near to where it adjoins the anterior surface of the implant. That medial-lateral clearance device is also used in the posterior access tunnel, so as to clear the medial surface of the implant of bony ingrowth at or near to where it adjoins the posterior surface of the implant.

It may be that more than one size of medial-lateral clearance device is used in this stage. In particular, for both the "left handed" and "right handed" versions, a plurality of medial-lateral clearance devices may be provided, with each having a different width of cutting edge. Therefore the smallest size of cutting edge can be used first, e.g. that may be 1 mm to 4 mm wide, such as 3 mm. Then a larger size of cutting edge may be used, e.g. that may be 4 mm to 10 mm wide, such as 5 mm or 6 mm or 7 mm.

There may be two different sizes, or three different sizes, or more.

Alternatively, just a single size of device may be provided. For example, a single device with cutting edge that is from 1 mm to 12 mm wide, such as from 4 to 9 mm or from 5 to 8 mm, may be provided.

The skilled reader will understand that the medial surface of the implant is cleared from both the anterior and posterior directions, and thus a cutting edge of 5 mm on both the left and right handed versions of the device would lead to a clearance of 10 mm in total on the medial surface. Likewise, the lateral surface of the implant is cleared from both the anterior and posterior directions, and thus a cutting edge of 5 mm on both the left and right handed versions of the device would lead to a clearance of 10 mm in total on the lateral surface.

When a single size of device is used, it may be preferred to have a size of cutting edge that is equal to half the width of the medial surface/lateral surface, or that is greater than half the width of the medial surface/lateral surface. If it is exactly half, this will mean that there is clearance of bony ingrowth across the full width of that surface. If it is greater than half, then the middle part of that surface will have bony ingrowth cleared from both the anterior and posterior directions.

However, in other embodiments, the cutting edge may be sized to be less than half the width of the medial surface/lateral surface. This may, for example, be the case for large femoral implants. In that case, there will be a strip of bony ingrowth that remains, towards the centre of the medial surface and towards the centre of the lateral surface. However, this may, for example, be de-bonded with a firm tap using a metal hammer on the taper of the implant in both a posterior and anterior direction.

When more than one single size of device is used, it may be preferred to have a largest size of cutting edge that is equal to half the width of the medial surface/lateral surface, or that is greater than half the width of the medial surface/lateral surface. If it is exactly half, this will mean that there is clearance of bony ingrowth across the full width of that surface. If it is greater than half, then the middle part of that surface will have bony ingrowth cleared from both the anterior and posterior directions.

However, in other embodiments, the largest size of cutting edge may be less than half the width of the medial surface/lateral surface. This may, for example, be the case for large femoral implants. In that case, there will be a strip of bony ingrowth that remains, towards the centre of the medial surface and towards the centre of the lateral surface. However, this may, for example, be de-bonded with a firm tap using a metal hammer on the taper of the implant in both a posterior and anterior direction.

In one embodiment the medial-lateral clearance device of the invention is provided with a handle. In one embodiment the handle is an integral part of the device, for example the device plus handle may be a one-piece construction product. In another embodiment, the handle is removable.

In the situation where the implant is collared, the collar will restrict the access that can be achieved by the medial-lateral clearance device. Specifically, the presence of a collar on the medial side at the shoulder, which usually extends from the medial border of the shoulder to halfway laterally, will prevent the clearance of the medial surface of the implant using the medial-lateral clearance device of the invention.

Therefore in one embodiment, the invention further comprises a fifth step of clearing the medial aspect of a collared implant.

This may be carried out using a wire delivery device.

The wire delivery device may be a novel wire delivery device according to the invention.

The wire delivery device of the invention comprises:
a first elongate body that extends from a first elongate edge to a second elongate edge and having a proximal end that can be provided with a handle and a distal end that is blunt, where there is a first wire guidance slot provided in a spaced relationship with the distal end and located within the first elongate body, wherein the wire guidance slot runs from an entrance at the first elongate edge to an exit at the second elongate edge, wherein the distance between the entrance and the distal end is greater than the distance between the exit and the distal end, such that the first wire guidance slot is at an angle to the elongate axis of the body;
a second elongate body that extends from a first elongate edge to a second elongate edge and having a proximal end that can be provided with a handle and a distal end that is blunt, where there is a second wire guidance slot provided in a spaced relationship with the distal end and located within the second elongate body, wherein the wire guidance slot runs from an entrance at the first elongate edge to an exit at the second elongate edge, wherein the distance between the entrance and the distal end is greater than the distance between the exit and the distal end, such that the second wire guidance slot is at an angle to the elongate axis of the body;
such that a wire can be fed through and extend between the first wire guidance slot and the second wire guidance slot, and the elongate bodies can be positioned in a spaced apart but aligned configuration with their second elongate edges closest to one another, so that the wire extends into the space between the elongate bodies at an angle,
whereby the wire can be pulled taught between the two elongate bodies and can then be used to cut by pulling the first and second elongate bodies in an alternating motion or by pushing the first and second elongate bodies in an alternating motion.

In one embodiment, the first wire guidance slot is at an angle of 120 to 140 degrees to the elongate axis of the body and the second wire guidance slot is at an angle of 120 to 140 degrees to the elongate axis of the body.

In one embodiment, the first elongate body is in the form of a flat plate and the second elongate body is in the form of a flat plate.

In one embodiment, the wire delivery device of the invention comprises:
a first elongate body in the form of a flat plate that extends from a first elongate edge to a second elongate edge and having a proximal end that can be provided with a handle and a distal end that is blunt, wherein the distal end is sloped from the first elongate edge to the second elongate edge at an angle to the elongate axis of the body of from 120 to 140 degrees, and where there is a first wire guidance slot provided in a spaced relationship with the distal end, the wire guidance slot running substantially parallel to the sloped distal end;
a second elongate body in the form of a flat plate that extends from a first elongate edge to a second elongate edge and having a proximal end that can be provided with a handle and a distal end that is blunt, wherein the distal end is sloped from the first elongate edge to the second elongate edge at an angle to the elongate axis of the body of from 120 to 140 degrees, and where there is a second wire guidance slot provided in a spaced relationship with the distal end, the wire guidance slot running substantially parallel to the sloped distal end;
such that a wire can be fed through and extend between the first wire guidance slot and the second wire guidance slot, and the elongate bodies can be positioned in a spaced apart but aligned configuration with their second elongate edges closest to one another, so that the wire extends into the space between the elongate bodies at an angle of from 120 to 140 degrees,
whereby the wire can be pulled taught between the two elongate bodies and can then be used to cut by pulling the first and second elongate bodies in an alternating motion or by pushing the first and second elongate bodies in an alternating motion.

When the wire is fed through and extends between the first wire guidance slot and the second wire guidance slot, it will be secured in these guidance slots. This may suitably be by welding. It will be appreciated that when the elongate bodies are positioned in a spaced apart but aligned configuration, with their second elongate edges adjacent to one another, they can be moved closer together to make the wire slack and can be moved apart to make the wire taut.

The wire is preferably a Gigli wire.

It is preferred that when the elongate bodies are flat plates, they are each provided with handles that extend out of the plane of the flat plate, to assist ease of control.

When using the wire delivery device of the invention, the wire is pulled taut between the two elongate bodies. It is then wrapped around the shoulder of the implant at a medial location beneath the collar, and the first and second elongate bodies can be pulled in an alternating motion to cause the wire to cut through the medial part of the femur beneath the shoulder. This can be continued until the wire comes to rest on the medial aspect of the implant proximally.

The two elongate bodies can then be threaded anteriorly and posteriorly in relation to the implant into the space that has already been created by the previous steps.

The sloped distal ends of the two elongate bodies will sit on the lateral aspect of the inner cortex of the femur, both anteriorly and posteriorly. The wire will not be directly exposed to the bone because it is secured in the wire guidance slots and these are spaced from the distal end. The blunt distal end therefore protects the wire from the bone.

The first and second elongate bodies can then be pushed in an alternating motion to cause the wire to cut, directing the force distally. As the wire traverses distally it will clear the bone-implant interface medially. The distal movement of the first and second elongate bodies may be carried out manually, or a reciprocating mechanism could be used to drive each of the first and second elongate bodies.

The invention therefore provides a method of removing an implant, especially a femoral implant, from the surrounding tissue, the method comprising:
creating two access tunnels in the surrounding tissue, one at the anterior of the implant and one at the posterior of the implant, with each access tunnel extending from an access point at the proximal surface of the surrounding tissue, which can be accessed by a person carrying out the procedure, to a point in the surrounding tissue that is located beyond the distal end of the implant, wherein the anterior access tunnel is spaced from and substantially parallel to the anterior surface of the implant and the posterior access tunnel is spaced from and substantially parallel to the posterior surface of the implant;
removing bony ingrowth located adjacent to the anterior access tunnel, and removing bony ingrowth located adjacent to the posterior access tunnel and the posterior surface of the implant, to extend the width of the access tunnels;
optionally removing bony ingrowth located at the distal end of the implant, to create a cavity at the distal end of the implant that extends in the medial and lateral directions;
removing bony ingrowth located at the antro-lateral edge of the implant, at the antro-medial edge of the implant, at the postro-lateral edge of the implant and at the postro-medial edge of the implant.

In one embodiment, the method comprises:
1) placing the targeting device according to the invention on the implant and locking it on the shoulder of the implant;
2) checking the alignment of the targeting device using the medial targeting device according to the invention;
3) checking the alignment of the targeting device using the external targeting device according to the invention;
4) drilling one or two access tunnels anteriorly and drilling one or two access tunnels posteriorly, wherein these access tunnels may optionally but preferably be circular in cross section and may optionally but preferably have a diameter of about 2 mm;
5) removing the targeting device from the implant;
6) using a chisel, which may optionally but preferably be a chevron chisel according to the invention, to widen the access tunnels;
7) using a chevron osteotome device according to the invention to extend the width of the access tunnels;
8) using a curette according to the invention to create a cavity at the distal end of the implant that extends in the medial and lateral directions; and
9) using a medial-lateral clearance device according to the invention to remove bony ingrowth located at the antro-lateral edge of the implant, at the antro-medial edge of the implant, at the postro-lateral edge of the implant and at the postro-medial edge of the implant.

If the implant is a collared implant, the method may suitably be modified to take this into account. In this regard, the above method may be used to clear the front and back and the lateral surface of the implant, but the medial collared clearance is carried out using a wire delivery device of the invention.

In one embodiment, only cutting devices with a thickness of 2 mm or less are used. In one embodiment, only cutting devices with a thickness of 1.5 mm or less are used. In one embodiment, only cutting devices with a thickness of 1 mm or less are used. This can be beneficial in terms of minimising loss of tissue around the implant.

In one embodiment, the method comprises:
a) placing the targeting device according to the invention on the implant and locking it on the shoulder of the implant;
b) checking the alignment of the targeting device using the medial targeting device according to the invention;
c) checking the alignment of the targeting device using the external targeting device according to the invention;
d) using a chevron chisel to create an access tunnel anteriorly and using a chevron chisel to create an access tunnel posteriorly, wherein these access tunnels may optionally but preferably have a depth of about 1 mm and may optionally but preferably have a width of about 5 to 8 mm;
e) removing the targeting device from the implant;
f) if desired, using a chisel, which may optionally but preferably be a chevron chisel according to the invention, to widen the access tunnels;
g) using a curette according to the invention to create a cavity at the distal end of the implant that extends in the medial and lateral directions; and h) using a medial-lateral clearance device according to the invention to remove bony ingrowth located at the antro-lateral edge of the implant, at the antro-medial edge of the implant, at the postro-lateral edge of the implant and at the postro-medial edge of the implant.

This method can be implemented using only cutting devices with a thickness of 1 mm or less.

The present invention provides each of the above mentioned items as apparatus/devices individually.

The present invention also provides a kit comprising any two or more such devices, such as any three or more, any four or more such devices. In one embodiment there is a kit comprising all of the above mentioned apparatus/devices.

In particular, in one embodiment the targeting device of the present invention is provided, optionally in combination with one or more of the other devices described above.

In another embodiment, the curette of the present invention is provided, optionally in combination with one or more of the other devices described above, e.g. in combination with the medial-lateral clearance device of the present invention and/or the chevron osteotome of the present invention and/or the wire delivery device of the present invention. It may be that this is provided as a kit for use with a targeting device as described in WO2017/032993, or as a kit for use with a targeting device of the present invention.

In one embodiment, a universal handle is provided which can be used as a handle for two or more of the devices described above, except for the targeting device which it will be appreciated does not require a handle. The universal handle may comprise a body having one or more grip portions at its proximal end and an engagement recess, such as a slot, at its distal end. The engagement recess is sized and shaped to receive the proximal end of the devices described above, except for the targeting device. In this regard, it will be appreciated that said devices may each be provided with a proximal end having the same size and shape, e.g. a flat plate, and the engagement recess of the universal handle is sized and shaped to receive this proximal end. In one embodiment, all of the devices included in the kit apart from the targeting device have the same size and shape of distal end, and thus the universal handle can be used as the handle for all of these devices.

In one embodiment, a brace sleeve is provided which can be used to provide structural support for the elongate body of any of the devices described above, except for the targeting device which it will be appreciated does not have an elongate body. The brace sleeve may comprise two elongate faces which are joined at one elongate edge and are open at the opposite elongate edge and at the two ends, so as to create an elongate cavity between the two faces within which an elongate body can be received. The brace sleeve can slide onto and over an elongate body to provide additional strength and resistance to bending during use. The brace sleeve can cover some, most or all of the length of an elongate body of any of the devices described above.

The present invention also provides a method in which all of the above steps are carried out. Preferably one or more of the above mentioned items are used in the method as apparatus/devices, e.g. the method may use any two or more such devices, such as any three or more, or any four or more such devices. In one embodiment the method comprises use of all of the above mentioned types of apparatus/devices.

DETAILED DESCRIPTION OF THE INVENTION

First Stage

The first stage of the surgical procedure is suitably effected using a targeting device, which ensures the access tunnels are created at the required locations on the anterior and posterior of the implant. The access tunnels may be created using conventional tools, such as a drill and drill bits, or a chisel, or a reciprocating saw, or a K-wire.

The targeting device of the invention comprises:

an anterior guide member, which comprises a first elongate body provided with a first angled channel therein, running from an entrance at the proximal end of the guide member to an exit at the distal end of the guide member, and where the first elongate body has a first contact element at its distal end for contacting the anterior surface of the shoulder of the femoral implant and for distancing the exit from the anterior surface of the shoulder of the implant, a posterior guide member, which comprises a second elongate body provided with a second angled channel therein, running from an entrance at the proximal end of the guide member to an exit at the distal end of the guide member, and where the second elongate body has a second contact element at its distal end for contacting the posterior surface of the shoulder of the implant and for distancing the exit from the posterior surface of the shoulder of the implant, an engagement member for locating and engaging the targeting device on the shoulder of the implant, which comprises a third elongate body with an engagement protrusion at its distal end, whereby the engagement protrusion can be received in a recess portion on the shoulder of the implant, and whereby the third elongate body can be located between and aligned with the first elongate body and the second elongate body, such that the elongate axes of the first, second and third elongate bodies are substantially aligned, and with the first and second angled channels converging in the direction of the distal end, a first pair of parallel connector rails, wherein each connector rail can slideably connect the anterior guide member and the posterior guide member via the engagement member, with the connector rails being received in connection bores in the anterior guide member and the posterior guide member, an adjustment system which can adjust the distance between the first elongate body and the third elongate body, so as to move the anterior guide member between a release position and a holding position, and which can adjust the distance between the second elongate body and the third elongate body, so to move the posterior guide member between a release position and a holding position;

wherein when the anterior guide member and the posterior guide member are connected by the first pair of connector rails, via the engagement member, the elongate axes of the elongate bodies are substantially aligned and the angled channels converge in the direction of the distal end, with the convergence angle of the angled channels being in the range of from 2 to 6 degrees, such as from 2 to 5 degrees, such that the engagement protrusion can be located in a recess portion on the shoulder of the implant, with the anterior guide member and the posterior guide member in their release positions, and then the adjustment system can be used to move the anterior guide member towards its holding position until the first contact element contacts the shoulder of the implant, with the exit of the first angled channel lying spaced from the anterior surface of the implant, and to move the posterior guide member towards its holding position until the second contact element contacts the shoulder of the implant, with the exit of the second angled channel lying spaced from the posterior surface of the implant.

It may be that the first pair of parallel connector rails comprises one medial rail and one lateral rail. Alternatively, it may be that the first pair of parallel connector rails comprises one proximal rail and one distal rail.

In one embodiment, there is a pair of parallel connector rails which comprises one medial rail and one lateral rail, where these rails are located at or near the midpoint between the proximal end of the guide members and the distal end of the guide members.

In one embodiment, there is a pair of parallel connector rails which comprises one proximal rail and one distal rail, where these rails are located at or near the midpoint between the medial face of the guide members and the lateral face of the guide members.

In one embodiment, the targeting device of the invention comprises:
  an anterior guide member, which comprises an elongate body provided with an angled channel therein, running from an entrance at the proximal end of the guide member to an exit at the distal end of the guide member, and where the elongate body has a first contact element at its distal end for contacting the anterior surface of the shoulder of the femoral implant and for distancing the exit from the anterior surface of the shoulder of the implant,
  a posterior guide member, which comprises an elongate body provided with an angled channel therein, running from an entrance at the proximal end of the guide member to an exit at the distal end of the guide member, and where the elongate body has a second contact element at its distal end for contacting the posterior surface of the shoulder of the implant and for distancing the exit from the posterior surface of the shoulder of the implant,
  an engagement member for locating and engaging the targeting device on the shoulder of the implant, which comprises an elongate body with an engagement protrusion at its distal end, whereby the engagement protrusion can be received in a recess portion on the shoulder of the implant, and whereby the elongate body of the engagement member can be located between and aligned with the elongate body of the anterior guide member and the elongate body of the posterior guide member, such that the elongate axes of the elongate bodies are substantially aligned, and with the angled channels converging in the direction of the distal end,
  a pair of parallel proximal connector rails, wherein each proximal connector rail can slideably connect the anterior guide member and the posterior guide member via the engagement member, with the connector rails being received in proximal connection bores in the anterior guide member and the posterior guide member,
  a pair of parallel distal connector rails, wherein each distal connector rail can slideably connect the anterior guide member and the posterior guide member via the engagement member, with the connector rails being received in distal connection bores in the anterior guide member and the posterior guide member,
  an adjustment system which can adjust the distance between the elongate body of the anterior guide member and the elongate body of the posterior guide member, so as to move the anterior guide member between a release position and a holding position, and to move the posterior guide member between a release position and a holding position;
  wherein when the anterior guide member and the posterior guide member are connected by the pair of proximal connector rails and the pair of distal connector rails, via the engagement member, the elongate axes of the elongate bodies are substantially aligned and the angled channels converge in the direction of the distal end,
  wherein the convergence angle of the angled channels is in the range of from 2 to 5 degrees,
  such that the engagement protrusion can be located in a recess portion on the shoulder of the implant, with the anterior guide member and the posterior guide member in their release positions, and then the adjustment system can be used to move the anterior guide member towards its holding position until the first contact element contacts the anterior surface of the shoulder of the implant, with the exit of the anterior angled channel lying spaced from the anterior surface of the implant, and to move the posterior guide member towards its holding position until the second contact element contacts the posterior surface of the shoulder of the implant, with the exit of the posterior angled channel lying spaced from the posterior surface of the implant.

In the present invention the convergence between the anterior angled channel and the posterior angled channel is in the range of 2 to 6 degrees, e.g. from 2 to 5 degrees, preferably 4 degrees. This is the actual angle of convergence between the anterior angled channel and the posterior angled channel when the targeting device is secured onto the implant.

The targeting device of the invention makes use of the fact that the vast majority of taper angles found on femoral implants are in the range of 2 to 5 degrees, and therefore the device can be provided with a pre-set angle of convergence within this range. It is therefore simpler to use than prior devices, yet can be readily used on a range of implants. A convergence angle of 4 degrees is preferred because this will provide good alignment with the majority of current commercial femoral implants.

Preferably the arrangement of the angled channels is symmetrical. In one embodiment, each has a fixed angle, with reference to the elongate axis of the elongate body in which the channel is provided, which is in the range of from 1 to 3 degrees, e.g. from 1 to 2.5 degrees, such as 2 degrees.

The targeting device of the invention is also beneficial due to the fact that it is secured on the shoulder of the implant and therefore can be directly secured using the recess that is provided as standard on a femoral implant for the purpose of receiving the impactor when the implant is being implanted.

The targeting device may be single use or may be multiple use. A single use device can suitably be made from sterilisable plastic. A multiple use device may suitably be made from medical grade stainless steel.

In one embodiment, the angled channel in the anterior guide member is an integral part of the guide member. In other words, the angled channel is fixed within the anterior guide member.

However, in another embodiment, the anterior guide member is provided with a recess that extends from its proximal end to its distal end and that can receive a channel providing unit. The channel providing unit is sized and shaped to slide into and be secured within the recess, extending substantially from the proximal end to the distal end. Preferably the recess includes a ledge or lip at the distal end, and the channel providing unit is sized and shaped to substantially correspond to the size and shape of the recess, such that the channel providing unit can be slid into the recess and it is then secured in place by resting on the ledge or lip. The channel providing unit includes one or more angled channel. The channel providing unit can be located and secured in the recess and when in this position it provides the anterior guide member with an angled channel therein, running from an entrance at the proximal end of the guide member to an exit at the distal end of the guide member, wherein the channel is at an angle in the range of from 1 to 3 degrees, e.g. from 1 to 2.5 degrees (preferably 2 degrees or 2.5 degrees or 3 degrees) to the elongate axis of the elongate body.

Likewise, in one embodiment, the angled channel in the posterior guide member is an integral part of the guide member. In other words, the angled channel is fixed within the posterior guide member.

However, in another embodiment, the posterior guide member is provided with a recess that extends from its proximal end to its distal end and that can receive a channel providing unit. The channel providing unit is sized and shaped to slide into and be secured within the recess, extending substantially from the proximal end to the distal end. Preferably the recess includes a ledge or lip at the distal end, and the channel providing unit is sized and shaped to substantially correspond to the size and shape of the recess, such that the channel providing unit can be slid into the recess and it is then secured in place by resting on the ledge or lip. The channel providing unit includes one or more angled channel. The channel providing unit can be located and secured in the recess and when in this position it provides the posterior guide member with an angled channel therein, running from an entrance at the proximal end of the guide member to an exit at the distal end of the guide member, wherein the channel is at an angle in the range of from 1 to 3 degrees, e.g. from 1 to 2.5 degrees (preferably 2 degrees or 2.5 degrees or 3 degrees) to the elongate axis of the elongate body.

The benefit of using the combination of a recessed guide member and an associated channel providing unit is that it is straightforward to change the angle of the channel to match the implant in question without needing a whole new device. Equally, it allows different shapes and/or sizes of channel to be provided to suit different tools, e.g. a circular cross sectional channel for a drill and drill bit, a square cross sectional channel for a chisel, and a rectangular cross sectional channel for a saw.

A kit including a number of different anterior and posterior channel providing units, with different angles and/or different cross sectional shapes and/or sizes, can therefore be provided as part of the present invention.

Whether the angled channels are integral or are provided by a channel providing unit, the following applies.

In one embodiment, the angle of the (or each) anterior angled channel and the angle of the (or each) posterior angled channel are the same. This reflects the fact that implants are usually symmetrical in design and therefore the angle of taper is the same anteriorly and posteriorly.

In one embodiment, the angle of the (or each) anterior angled channel and the angle of the (or each) posterior angled channel are selected from: 1 degree, 1.5 degrees, 2 degrees, 2.5 degrees, and 3 degrees. In one embodiment, the angle of the (or each) anterior angled channel and the angle of the (or each) posterior angled channel are selected from: 1 degree, 1.5 degrees, 2 degrees, and 2.5 degrees. It may be that the angle of the (or each) anterior angled channel and the angle of the (or each) posterior angled channel are both 1.5 degrees, and therefore the convergence angle is 3 degrees, or the angle of the (or each) anterior angled channel and the angle of the (or each) posterior angled channel are both 2 degrees, and therefore the convergence angle is 4 degrees.

In practice, it may be found that the convergence angle of the angled channels when the targeting kit has been secured to the implant (i.e. when the anterior guide member is in its holding position and the posterior guide member is in its holding position) is less than the sum of the fixed angles of the two angled channels. For example, about 0.5 to 1 degree of angle may be lost from each angled channel due to the tightening action of moving the guide members into their holding positions.

Therefore it may be that each of the angled channels has a fixed angle with reference to the elongate axis of the elongate body in which it is provided that is in the range of from 2 to 3 degrees, such as from 2.5 to 3 degrees. It may, for example, be that using angled channels each with a 3 degree angle in practice results in a convergence angle of the angled channels when the targeting kit has been secured to the implant of from 4 to 5 degrees.

In one embodiment, the anterior angled channel(s) and the posterior angled channel(s) have circular cross sections, or square cross sections, or rectangular cross sections. It is desirable that the anterior angled channel and the posterior angled channel have the same shape of cross section, because this shape impacts the tool that can be used to then create the access tunnels, and it is clearly more convenient to be able to use the same tool to make the both the anterior and posterior tunnels.

It may be that the angled channels have circular cross sections with a diameter of about 3 mm, or have square cross sections with a cross section of about 3 mm×3 mm, or have rectangular cross sections with a cross section of about 1-2 mm×8-10 mm. A rectangular cross section can be useful for allowing the use of a saw, e.g. a reciprocating saw, or a chisel. A square cross section can be useful in that it can receive a chisel. A circular cross section can of course receive a drill bit or K-Wire.

It can be envisaged that there may be two or more anterior angled channels and two or more posterior angled channels. In such a multiple channel embodiment, the channels may be smaller in size, e.g. they may be circular cross section with diameters of about 1 mm to about 2 mm or they may have square cross sections with a cross section of from about 1×1 mm to about 2×2 mm. For example, there may be two or three channels which are circular cross section with diameters of about 2 mm, and/or there may be two or three channels which are circular cross section with diameters of about 1 mm. This embodiment with two or more channels anteriorly and/or two or more channels posteriorly can in particular be useful if there is insufficient room anteriorly or posteriorly for a 3 mm drill. By using multiple smaller holes, multiple tunnels can be created anteriorly and/or posteriorly, and each can then be widened in accordance with the second and third steps until a space is cleared at the bone-implant interface that extends, at least substantially, to both the medial and lateral edges of the implant.

In embodiments where there are two or more channels, these may be provided separately or they may be co-joined. In embodiments where they are co-joined there is therefore a single entrance to the channels but this can be understood as being made up of the cross sectional shapes of the two or more channels. For example, two co-joined channels each having a circular cross section will together form a figure "8" shaped entrance. FIGS. 9a and 9b show two co-joined channels each having a circular cross section (2a). FIGS. 7a, 7d and 8b show three co-joined channels, one having a rectangular cross section and two having a circular cross section (2a).

In one embodiment, in both the anterior and the posterior guide members there are three channels: these are two channels which are circular in cross section (e.g. with diameters of about 1 mm to about 2 mm), plus one channel which is rectangular in cross section (e.g. with a cross section of about 1-2 mm×8-10 mm). These channels may be co-joined.

In another embodiment, in both the anterior and the posterior guide members there are two channels: these are both circular in cross section. For example, there may be two channels which are circular in cross section with diameters of about 1 mm to about 2 mm. These channels may be co-joined.

In another embodiment, in both the anterior and the posterior guide members there are two channels: these are one channel which is circular in cross section (e.g. with a diameter of about 1 mm to about 3 mm), plus one channel which is rectangular in cross section (e.g. with a cross section of about 1-2 mm×8-10 mm). These channels may be co-joined.

In embodiments where an external targeting device is used to check the alignment of the targeting device, the external targeting device may be connected to the targeting device by the anterior guide member interlocking component being received in the first angled channel and the posterior guide member interlocking component being received in the second angled channel.

However, in a preferred embodiment, the targeting device can include a first receiving channel adjacent to the first angled channel and aligned therewith and can include a second receiving channel adjacent to the second angled channel and aligned therewith. The anterior guide member interlocking component and the posterior guide member interlocking component are then received in these channels respectively. In this embodiment the first and second receiving channels may, for example, be circular in cross section and may each have a diameter of from 2 to 4 mm, such as about 3 mm. However, other shapes could be envisaged, e.g. they could have a square cross section, and likewise other sizes could be envisaged. The first and second receiving channels may, for example, extend for a depth of 15 mm or more, such as 20 mm or more, or 25 mm or more. The first and second receiving channels may, for example, extend for a depth that is less than the depth of the targeting device, such as from 15 to 70 mm or from 20 to 60 mm, e.g. from 25 to 40 mm.

The first contact element at the distal end of the anterior guide member may be a lip or a leg that extends from the distal end of the elongate body. This lip or leg is suitably located at or near the inner surface of the elongate body which is the surface that, in use, is closest to the engagement member, i.e. it is provided at or near the posterior surface of the anterior guide member.

The lip or leg may be provided with a contact face for contacting the surface of the shoulder of the femoral implant or cancellous bone just beyond the shoulder of the implant. Therefore, in use, the contact face of the contact element can contact the surface of the shoulder of the femoral implant, or cancellous bone just beyond the shoulder of the implant, and serves to distance the exit from the surface of the shoulder of the implant, because the exit is located between the lip or leg and the exterior surface of the elongate body which is the surface that, in use, is furthest from the engagement member.

Alternatively, the lip or leg may be provided with one or more engaging protrusions. These suitably have a sharp or pointed end. These may, for example, be sharpened prongs or nails or the like.

These engaging protrusions can engage into cancellous bone at the anterior aspect of the implant, just beyond the shoulder of the implant.

In particular, it may be that when the anterior guide member is in the release position these engaging protrusions are driven into the cancellous bone. The engaging protrusions will easily cut through the cancellous bone. The engaging protrusion of the engagement member will also be secured in the recess. Then the adjustment system (e.g. double ended screw) is used to move the anterior member to its holding position. This will provide a secure locked arrangement.

It may be that the lip or leg has two or more engaging protrusions. It will be appreciated that the engaging protrusions should be spaced apart, to provide a secure engagement at two separate locations.

Likewise, the second contact element at the distal end of the posterior guide member may be a lip or a leg that extends from the distal end of the elongate body. This lip or leg is suitably located at or near the inner surface of the elongate body which is the surface that, in use, is closest to the engagement member, i.e. it is provided at or near the anterior surface of the posterior guide member.

The lip or leg may be provided with a contact face for contacting the surface of the shoulder of the femoral implant or cancellous bone just beyond the shoulder of the implant. Therefore, in use, the contact face of the contact element can contact the surface of the shoulder of the femoral implant, or cancellous bone just beyond the shoulder of the implant, and serves to distance the exit from the surface of the shoulder of the implant, because the exit is located between the lip or leg and the exterior surface of the elongate body which is the surface that, in use, is furthest from the engagement member.

Alternatively, the lip or leg may be provided with one or more engaging protrusions. These suitably have a sharp or pointed end. These may, for example, be sharpened prongs or nails or the like.

These engaging protrusions can engage into cancellous bone at the posterior aspect of the implant, just beyond the shoulder of the implant.

In particular, it may be that when the posterior guide member is in the release position these engaging protrusions are driven into the cancellous bone. The engaging protrusions will easily cut through the cancellous bone. The engaging protrusion of the engagement member will also be secured in the recess. Then the adjustment system (e.g. double ended screw) is used to move the posterior member to its holding position. This will provide a secure locked arrangement.

It may be that the lip or leg has two or more engaging protrusions. It will be appreciated that the engaging protrusions should be spaced apart, to provide a secure engagement at two separate locations on the surface of the implant.

It may be preferred that both the anterior and posterior guide members have a lip or leg that is provided with one or more engaging protrusions. These engaging protrusions can engage into cancellous bone at the anterior and posterior aspects of the implant, just beyond the shoulder of the implant.

In particular, it may be that when the anterior and posterior guide members are in the release position these engaging protrusions are driven into the cancellous bone. The engaging protrusions will cut through and engage into cancellous bone at the anterior and posterior aspect of the implant, just beyond the shoulder of the implant. The engaging protrusion of the engagement member will also be secured in the recess. Then the adjustment system (e.g. double ended screw) is used to move the anterior and posterior guide members towards each other and to their holding positions. This will provide a secure locked arrangement.

The elongate bodies of the anterior and posterior guide members may each independently have a height of from 40 to 120 mm, such as from 50 to 110 mm, e.g. from 80 to 100 mm. The elongate bodies of anterior and posterior guide members may each independently have a width (antro-posterior direction) of from 5 to 10 mm, such as from 5 to 8 mm, e.g. from 6 to 8 mm. The elongate bodies of the anterior and posterior guide members may each independently have a depth (medio-lateral direction) of from 10 to 20 mm, such as from 12 to 20 mm, e.g. from 12 to 18 mm.

The engagement member comprises an elongate body with an engagement protrusion at its distal end. This engagement protrusion is sized and shaped to be received in a recess portion on the shoulder of the implant. The skilled person will appreciate that a femoral implant will, as standard, include a recess portion on the shoulder which receives an impactor when the implant is being implanted. This recess is located on the shoulder at the proximal end of the central axis. Therefore the engagement protrusion ensures central alignment for the targeting device on the femoral implant.

In one embodiment the engagement protrusion has male screw threads and can therefore be screwed into the recess portion if the recess portion has female screw threads. In another embodiment the engagement protrusion is received within and engages with the recess portion due to being substantially the same size in at least one dimension, therefore creating an engagement fit in said at least one dimension. In another embodiment the engagement protrusion is sized and shaped such that it can be press-fitted into the recess portion of a femoral implant.

Recess portions on femoral implants may, for example, have: a circular cross section with a female screw thread, being 5-8 mm diameter and having a depth of 5-8 mm; or a square cross section with a width of 2-4 mm and having a depth of 3-5 mm; or a rectangular cross section with width 2-4 mm and length 3-5 mm and having a depth of 3-5 mm.

Therefore the engagement protrusion may suitably be sized and shaped to fit into and engage with such a recess portion.

So the engagement protrusion may, for example, for example, have: a circular cross section with a male screw thread, being 5-8 mm diameter and having a depth of 5-8 mm; or a square cross section with a width of 2-4 mm and having a depth of 3-5 mm; or a rectangular cross section with width 2-4 mm and length 3-5 mm and having a depth of 3-5 mm.

The elongate body of the engagement member can be located between and aligned with the elongate body of the anterior guide member and the elongate body of the posterior guide member, such that the elongate axes of the elongate bodies are substantially aligned, and with the anterior and posterior angled channels converging in the direction of the distal end.

The elongate body of the engagement member may have a height of from 40 to 120 mm, such as from 50 to 110 mm, e.g. from 80 to 100 mm. The elongate body of the engagement member may have a width (antro-posterior direction) of from 5 to 10 mm, such as from 5 to 8 mm, e.g. from 6 to 8 mm. The elongate body of the engagement member may have a depth (medio-lateral direction) of from 10 to 20 mm, such as from 12 to 20 mm, e.g. from 12 to 18 mm.

Each connector rail slideably connects the anterior guide member and the posterior guide member via the engagement member. Each connector rail is received in a connection bore in the anterior guide member and a connection bore in the posterior guide member.

Each connector rail may optionally be provided with a spring or other biasing means that serves to bias the anterior guide member and the posterior guide member into their release positions. The biasing force of the spring or other biasing means can be overcome by use of the adjustment system to move the anterior guide member and the posterior guide member into their holding positions. The spring may be located around the outer circumference of the connector rail.

In one preferred embodiment, the first pair of parallel connector rails comprises one proximal rail and one distal rail.

It will be appreciated that the proximal connector rail is located closer to the proximal end of the targeting device than the distal connector rail. However, this does not mean that the proximal connector rail must necessarily be located at or near the proximal end of the targeting device, nor that the distal connector rail must necessarily be located at or near the distal end of the targeting device.

In one embodiment, the proximal connector rail is located within the half of the length of the targeting device that is closest to the proximal end (the top half), whilst the distal connector rail is located within the half of the length of the targeting device that is closest to the distal end (the bottom half).

In one embodiment, there is a pair of parallel connector rails which comprises one proximal rail and one distal rail, where these rails are located at or near the midpoint between the medial face of the guide members and the lateral face of the guide members. In one embodiment, the parallel connector rails are also parallel with the adjustment system. It may be that the proximal rail and the distal rail are located either side of the adjustment system and substantially equidistant therefrom.

In one embodiment, the connector rails are slidably secured to the engagement member. Therefore the proximal connector rail is received in proximal connection bores in the anterior guide member, in the engagement member, and in the posterior guide member. Likewise, the distal connector rail is received in distal connection bores in the anterior guide member, in the engagement member, and in the posterior guide member.

Alternatively, it may be that the first pair of parallel connector rails comprises one medial rail and one lateral rail.

It will be appreciated that the medial connector rail is located closer to the medial face of the targeting device than the lateral connector rail. In one embodiment, the medial connector rail is located at the medial face of the targeting device, and the lateral connector rail is located at the lateral face of the targeting device.

In one embodiment, there is a pair of parallel connector rails which comprises one medial rail and one lateral rail, where these rails are located at or near the midpoint between the proximal end of the guide members and the distal end of the guide members. In one embodiment, the parallel connector rails are also parallel with the adjustment system. It may be that the medial rail and the lateral rail are located either side of the adjustment system and substantially equidistant therefrom.

In one embodiment, the connector rails are slidably secured to the engagement member. Therefore the medial connector rail is received in medial connection bores provided on the anterior guide member, on the engagement member, and on the posterior guide member. Likewise, the lateral connector rail is received in lateral connection bores provided on the anterior guide member, on the engagement member, and on the posterior guide member.

In one embodiment, there is a first pair of parallel connector rails which comprises one proximal rail and one distal rail and there is a second pair of parallel connector rails which comprises one medial rail and one lateral rail. Each of these pairs of connector rails may be as described above.

In embodiments where there is a first pair of parallel connector rails and a second pair of parallel connector rails all of the connector rails should be parallel to one another.

The elongate body of the engagement member may comprise a central locking rod, a medial elongate wing and a lateral elongate wing. In such an embodiment, the engagement protrusion extends from the central locking rod.

In this embodiment, one of the pair of parallel proximal connector rails can slideably connect the anterior guide member and the posterior guide member, via the medial elongate wing, with proximal connection bores in each of the anterior guide member and the posterior guide member, whilst the other of the pair of parallel proximal connector rails can slideably connect the anterior guide member and the posterior guide member, via the lateral elongate wing, with proximal connection bores in each of the anterior guide member and the posterior guide member. Meanwhile, one of the pair of parallel distal connector rails can slideably connect the anterior guide member and the posterior guide member, via the medial elongate wing, with distal connection bores in each of the anterior guide member and the posterior guide member, whilst the other of the pair of parallel distal connector rails can slideably connect the anterior guide member and the posterior guide member, via the lateral elongate wing, with distal connection bores in each of the anterior guide member and the posterior guide member.

It will be appreciated that the pair of parallel proximal connector rails is located closer to the proximal end of the targeting device than the pair of parallel distal connector rails. However, this does not mean that the pair of parallel proximal connector rails must necessarily be located at or near the proximal end of the targeting device.

In one embodiment, the pair of parallel proximal connector rails is located within the half of the length of the targeting device that is closest to the proximal end (the top half), whilst the pair of parallel distal connector rails is located within the half of the length of the targeting device that is closest to the distal end (the bottom half).

In one such embodiment, the pair of parallel proximal connector rails is located within the third of the length of the targeting device that is closest to the proximal end (the top third), whilst the pair of parallel distal connector rails is located within the third of the length of the targeting device that is closest to the distal end (the bottom third).

However, in a preferred embodiment the pair of parallel proximal connector rails is located within the middle half of the targeting device, namely at a point between 25% and 75% along the length of the targeting device, whilst the pair of parallel distal connector rails is located within the third of the length of the targeting device that is closest to the distal end (the bottom third).

So, for example, the pair of parallel proximal connector rails may be located at or near the mid-point along the length of the targeting device, whilst the pair of parallel distal connector rails may be located at or near the closest to the distal end (the bottom third), e.g. at a point about 25% along the length of the targeting device from the distal end.

In some embodiments, the adjustment system may apply a compression force when it moves the anterior guide member and the posterior guide member towards their holding positions. This can apply a compression force on the anterior and second contact elements, which can in turn transfer to the shoulder both anteriorly and posteriorly. Therefore it may be preferable that both the parallel proximal connector rails and the parallel distal connector rails are located in the bottom two-thirds of the targeting device, such as in the bottom half of the targeting device, i.e. each set of rails is substantially equidistant between the proximal and distal ends or closer to the distal end.

In one embodiment, the adjustment system is located between the parallel proximal connector rails and the parallel distal connector rails, e.g. at or near the midpoint between the parallel proximal connector rails and the parallel distal connector rails.

In one embodiment, the pair of parallel proximal connector rails and the pair of parallel distal connector rails are fixedly secured to the engagement member. They may be attached to, or integral with, the engagement member. Therefore the pair of parallel proximal connector rails is part of the engagement member, extending from the engagement member in both anterior and posterior directions. Likewise, the pair of parallel distal connector rails is part of the engagement member, extending from the engagement member in both anterior and posterior directions.

In an alternative embodiment, the pair of parallel proximal connector rails and the pair of parallel distal connector rails are slidably secured to the engagement member. Therefore the proximal connector rails are received in proximal connection bores in engagement member, extending from the engagement member in both anterior and posterior directions. Likewise, the distal connector rails are received in distal connection bores in engagement member, extending from the engagement member in both anterior and posterior directions It could also be envisaged that one or more of the connector rails is fixedly secured to the engagement member whilst the remainder of the connector rails are slidably secured to the engagement member.

In one embodiment, the elongate body of the engagement member comprises a central locking rod, a medial elongate wing and a lateral elongate wing, and that one of the pair of parallel proximal connector rails is attached to, or integral with medial elongate wing and the other one of the pair of parallel proximal connector rails is attached to, or integral with lateral elongate wing, whilst one of the pair of parallel distal connector rails is attached to, or integral with medial elongate wing and the other one of the pair of parallel distal connector rails is attached to, or integral with lateral elongate wing.

In another embodiment, the elongate body of the engagement member is an elongate block, e.g. a rectangular prism shape. It may be that the block includes a rod extending therethrough, with the distal end of the rod providing the engagement protrusion. The rod may be removable and replaceable; this would permit rods with different sized or shaped engagement protrusions to be provided and selected based on the size and shape of the recess on the femoral implant. Thus it is envisaged that there could be a kit comprising multiple rods with different sized or shaped engagement protrusions.

In all embodiments involving a pair of parallel proximal connector rails and a pair of parallel distal connector rails, all of these connector rails should be parallel to one another.

The adjustment system may comprise a threaded adjustment member, such as a screw. The threaded adjustment member may suitably have a diameter of from 4 to 6 mm. It may, in one embodiment, have a 1 mm thread.

In particular, it is preferred that the adjustment system comprises a double ended screw, also known as a left- and right-screw or a right- and left-screw. As the skilled reader will appreciate, such a screw has a first end portion with a right-hand screw thread and a second end portion with a left-hand screw thread, and a non-threaded section in the middle, between the two threaded end portions.

The double ended screw can be received in a first engaging bore in the anterior guide member, a second engaging bore in the posterior guide member and a non-engaging bore in the engagement member. It will be appreciated that this series of bores will, in use, be aligned, so that the double ended screw can be received in, and extend through, each of these bores. This series of bores is parallel to the connection bores. Therefore in use the anterior guide member, the engagement member and posterior guide member are connected and aligned using the pair of proximal connector rails and the pair of distal connector rails and the double ended screw.

The double ended screw does not engage with the non-engaging bore in the engagement member. The non-threaded section in the middle of the double ended screw will be located in the non-engaging bore. Therefore the double ended screw extends through the engagement member but is not attached to the engagement member.

The double ended screw does engage with the engaging bore in the posterior guide member and does engage with the engaging bore in the anterior guide member. The threaded portions at the two ends of the double ended screw are received in and engage with the engaging bore in the anterior guide member and the engaging bore in the posterior guide member. The engaging bores may optionally be threaded. Therefore, in use, the double ended screw is attached to the anterior guide member and to the posterior guide member.

It may be that the right hand screw thread of the double ended screw is provided in the anterior guide member and the left hand screw thread of the double ended screw in the posterior guide member, and the invention will be further described in terms of this arrangement. However, it will be appreciated that the reverse configuration, with the right hand screw thread being provided in the posterior guide member and the left hand screw thread being provided in the anterior guide member, could also be used.

In use, when the screw is turned clockwise, from the anterior approach, the anterior and posterior members will each simultaneously move towards the engagement member, i.e. towards the holding positions. It will be appreciated that their movements will approximate one another and they will remain equidistant from the engagement member. Once the screw is fully tightened, the first and second contact elements will contact the shoulder of the implant, anteriorly and posteriorly. The device will therefore be secured to the shoulder. Anticlockwise rotation of the screw anteriorly will result in movement of the anterior and posterior member away from the engagement member, i.e. towards the release positions, and so will release the device from the shoulder of the implant.

The converse is true in relation to the turning of the screw from the posterior approach. Anticlockwise rotation of the screw will simultaneously move the anterior and posterior members towards the engagement member, i.e. towards the holding positions. When fully tightened anticlockwise, the holding position is reached and the device is secured on the implant shoulder. Meanwhile, when the screw is turned clockwise from the posterior approach it will result in the anterior and posterior members moving away from the engagement member, i.e. towards the release positions, and so will release the device from the shoulder of the implant.

The double ended screw is, in use, suitably positioned parallel to the pair of parallel proximal connector rails and the pair of parallel distal connector rails. It may be located about half way between the two pairs of connector rails.

Therefore the adjustment system to move the anterior and posterior members is suitably a right- and left-handed screw with threads in the anterior and posterior guide members and with the central unthreaded part passing through the engagement member.

Therefore when the anterior guide member and the posterior guide member are slidably connected by the pair of proximal connector rails and the pair of distal connector rails, via the engagement member, the elongate axes of the elongate bodies are substantially aligned and the angled channels converge in the direction of the distal end. The engagement protrusion can be located in a recess portion on the shoulder of the implant, with the anterior guide member and the posterior guide member in their release positions, and then the anterior adjustment member can be used to move the anterior guide member towards its holding position until the first contact element contacts the anterior surface of the shoulder of the implant, with the exit of the anterior angled channel lying spaced from the anterior surface of the implant, and the posterior adjustment member can be used to move the posterior guide member towards its holding position until the second contact element contacts the posterior surface of the shoulder of the implant, with the exit of the posterior angled channel lying spaced from the posterior surface of the implant.

Additional Checking Devices to be Used with the Targeting Device

Optionally the above design of device is used in combination with a medial targeting device. This device can be used to double check the alignment of the targeting kit in the antero-posterior plane before the tunnels are drilled.

When a medial targeting device is used, the targeting device is provided with an alignment slot located at the proximal end of the engagement member. This alignment slot is in longitudinal alignment with the engagement protrusion of the engagement member.

The medial targeting device is in the form of a plate, which has an enlarged head at the proximal end and an elongate body that extends to the distal end. The enlarged head is sized and shaped to be received in the alignment slot of the engagement member. In one embodiment, the enlarged head is circular in shape. A curved shape assists with ease of use. The elongate body has a length greater than the distance from the alignment slot to the engagement protrusion of the engagement member. Therefore when the enlarged head is located in the alignment slot, the distal end of the medial targeting device can extend beyond the engagement protrusion of the engagement member.

In use, the enlarged head is received in the alignment slot of the engagement member and the elongate body of the medial targeting device is then pivoted until it contacts the proximal end of the neck of the femoral implant. An assessment can be made as to whether the elongate plate is bisecting the neck centrally in the antero-posterior plane. If it is not, the location of the targeting device can be adjusted until the elongate plate of the medial targeting device does bisect the neck centrally in the antero-posterior plane.

Optionally the above design of device is used in combination with an external targeting device. This device can be used to double check the alignment of the targeting kit in the anterior-posterior plane before the tunnels are drilled.

In one embodiment, the external targeting device may comprise:
- a targeting device interlocking portion,
- an alignment portion, and
- a holding arrangement for holding and pivoting the alignment portion relative to the targeting device interlocking portion, wherein the targeting device interlocking portion comprises a planar support body provided with:
- an anterior guide member interlocking component, which comprises a first locking pin that extends from the planar support body in the same plane and can be received in the first angled channel or a first receiving channel adjacent thereto and aligned therewith, and
- a posterior guide member interlocking component, which comprises a second locking pin that extends from the planar support body in the same plane and can be received in the second angled channel or a second receiving channel adjacent thereto and aligned therewith, wherein the alignment portion comprises a planar elongate body having an angled tip at the distal end, and wherein the holding arrangement holds the planar elongate body and the planar support body in the same plane, but permits the pivotal movement of the planar elongate body relative to the planar support body within that plane,
- such that the first locking pin can be received in the first angled channel of the targeting device or a first receiving channel adjacent thereto and aligned therewith, and the second locking pin can be received in second angled channel of the targeting device or a second receiving channel adjacent thereto and aligned therewith,
- such that the planar support body is aligned with the anterior-posterior plane in which the first and second angled channels lie, and such that the planar elongate body is consequently also aligned with the anterior-posterior plane in which the first and second angled channels lie, such that the planar elongate body can be pivoted relative to the planar support body until the angled tip is alongside the implant and the plane of the angled tip can be compared to the centreline in the anterior-posterior plane, as determined via x-ray.

In one embodiment, the targeting device includes a first receiving channel adjacent to the first angled channel and aligned therewith and includes a second receiving channel adjacent to the second angled channel and aligned therewith. The anterior guide member interlocking component and the posterior guide member interlocking component are then received in these channels respectively. In this embodiment the first and second receiving channels may, for example, be circular in cross section and may each have a diameter of from 2 to 4 mm, such as about 3 mm. However, other shapes could be envisaged, e.g. they could have a square cross section, and likewise other sizes could be envisaged. The first and second receiving channels may, for example, extend for a depth of 15 mm or more, such as 20 mm or more, or 25 mm or more. The first and second receiving channels may, for example, extend for a depth that is less than the depth of the targeting device, such as from 15 to 70 mm or from 20 to 60 mm, e.g. from 25 to 40 mm.

In an alternative embodiment, the anterior guide member interlocking component is received in the first angled channel and the posterior guide member interlocking component is received in the second angled channel.

If the plane of the angled tip is not aligned with the centreline in the anterior-posterior plane, the location of the targeting device can be adjusted until the angled tip does align with the centreline in the anterior-posterior plane.

In one embodiment the holding arrangement comprises a pivot nut, optionally together with an associated a pivot washer. It may be that the holding arrangement comprises a pivot nut, optionally together with an associated pivot washer, and a locking screw that can be rotated from an open position where pivoting can occur to a locked position where pivoting is prevented.

It may be that the anterior guide member interlocking component and the posterior guide member interlocking component are arranged such that the distance between them, can be altered. For example, the posterior guide member interlocking component may be provided in a fixed location on the planar support body whilst the anterior guide member interlocking component can slidably move along the planar support body so as to alter the distance between the anterior guide member interlocking component and the posterior guide member interlocking component. In one embodiment a groove is provided in the planar support body and the anterior guide member interlocking component is provided with an engaging pin that engages with and can slideably move along the groove and can be secured at any location therein.

The arrangement as to which guide member interlocking component is fixed and which guide member interlocking component is moved may also be reversed, i.e. the anterior component may be fixed and the posterior component may be moveable, or it may alternatively be that both components are moveable.

Having the ability to move the anterior guide member interlocking component and the posterior guide member interlocking component relative to one another can assist with readily locating these interlocking components in the relevant channels on the targeting device.

Cutting Tools to be Used with the Targeting Device

The access tunnels may be created using conventional tools, such as a drill and drill bits, or a chisel, or a reciprocating saw, or a K-wire. Of course, the tool used could be bespoke instead. The key feature is that the tool is elongate and has at least one edge that is sufficiently sharp that when the tool is operated it can be used to create access tunnels on the anterior and posterior of the implant.

It may be that a chevron chisel according to the invention is used. A chevron chisel according to the invention comprises:
- an elongate body in the form of a flat plate having an upper face and a lower face, wherein the elongate body extends from a first elongate edge to a second elongate edge and having a proximal end that can be provided with a handle and having a distal end; and a cutting portion located at the distal end which comprises a first cutting face and a second cutting face which meet at an angled cutting point, wherein the first cutting face extends at an angle of from 30 to 60 degrees, e.g. from 40 to 50 degrees, from the first elongate edge when measured with respect to the elongate axis of the elongate body, and the second cutting face extends at an angle of from 30 to 60 degrees, e.g. from 40 to 50 degrees, from the second elongate edge when measured with respect to the elongate axis of the elongate body, and wherein the first cutting face extends at an angle of from 30 to 60 degrees, e.g. from 40 to 50 degrees, from the lower face to the upper face, and wherein the second cutting face extends at an angle of from 30 to 60 degrees, e.g. from 40 to 50 degrees, from the lower face to the upper face.

Preferably the angled cutting point is located substantially centrally between the first elongate edge and the second elongate edge.

The chevron chisel may optionally have a depth (the lower face to the upper face) of from 0.5 to 3 mm, e.g. 1 to 2 mm; it may be about 1 mm deep. The chevron chisel may optionally have a width (first elongate edge to a second elongate edge) of from 4 to 10 mm, e.g. 5 to 9 mm; it may be about 7 to 8 mm wide.

In one embodiment, a K-wire is used and a chevron chisel is used.

Second Stage

The second stage of the procedure involves removing bony ingrowth located adjacent to the anterior access tunnel, and removing bony ingrowth located adjacent to the posterior access tunnel and the posterior surface of the implant. The intention of this step is to extend the width of the access tunnels, preferably so that their widths substantially correspond with the width of the implant. Therefore the anterior access tunnel is broadened in a plane that is substantially parallel to the anterior surface of the implant, and the posterior access tunnel is broadened in a plane that is substantially parallel to the posterior surface of the implant.

This may be carried out using the chevron osteotome device of the invention (or a set of two or more chevron osteotome devices according to the invention).

The chevron osteotome device of the invention comprises:

an elongate body having a proximal end that can be provided with a handle and a distal end, wherein the elongate body includes a distal section extending from the distal end to a shoulder point, wherein the shoulder point is located closer to the distal end than the proximal end;

a cutting portion extending outwardly from both sides of the elongate body at the shoulder point, the cutting portion having a first angled cutting side that extends outwardly from one side of the elongate body at the shoulder point, and a second angled cutting side that extends outwardly from the opposite side of the elongate body at the shoulder point, wherein the cutting portion has a front face and a back face which are connected by the first angled cutting side and the second angled cutting side, the front face being aligned with and a continuation of the elongate body, and the back face being aligned with and a continuation of the elongate body, such that the cutting portion has the same depth as the elongate body, and wherein the front face and the back face are blunt;

such that the distal end of the chevron osteotome device can be located in an access tunnel and chevron osteotome device can be pushed in the direction of the distal end of the implant so as to cut away bony ingrowth on both sides of the access tunnel with the first angled cutting side and the second angled cutting side.

The elongate body suitably has a diameter that is equal to or slightly less than the diameter of the access tunnel. For example its diameter may be less than the diameter of the access tunnel by an amount of 1 mm or less, e.g. by an amount of from 0.1 to 0.5 mm.

As noted above, the diameter of the access tunnels may suitably be from 0.5 mm to 5 mm, preferably from 1 mm to 4 mm, e.g. from 2 mm to 4 mm or from 2.5 mm to 3.5 mm.

In one embodiment the diameter of the elongate body is from 0.4 mm to 4.5 mm, preferably from 0.5 mm to 4 mm, e.g. from 1 mm to 4 mm or from 1.5 mm to 3.5 mm.

In one embodiment the shoulder point is located at a distance from the distal end of from 0.5 to 20 mm, such as from 0.5 to 15 mm or from 0.5 to 10 mm; preferably it is at a distance from the distal end of from 1 to 15 mm, such as from 1.5 to 12 mm or from 2 to 10 mm, e.g. from 2.5 to 10 mm.

The width of cutting portion (the maximum distance between the first cutting side and the second cutting side) may, for example, be from 2 mm to 20 mm, preferably from 4 mm to 15 mm, e.g. from 5 mm to 15 mm or from 6 mm to 12 mm.

The distal end of the chevron osteotome device may be blunt or may be sharp. The distal end of the elongate body may optionally be rounded.

Preferably the cutting portion has a front face that is substantially planar. Preferably the cutting portion has a back face that is substantially planar.

In one embodiment the elongate body has an upper face that is substantially planar and a lower face that is substantially planar. For example, the elongate body may be an elongate square prism or rectangular prism. In another embodiment, the elongate body may have a curved outer surface, e.g. it may be the shape of an elongate cylinder.

The first angled cutting side and the second angled cutting side are located towards and face towards the distal end of the cutting portion, i.e. such that cutting occurs as the chevron osteotome device is pushed into the tunnel.

In one embodiment the cutting portion is triangular in cross sectional shape, with two of the three sides of the triangle being the first cutting side and the second cutting side (with these sides facing towards the distal end of the cutting portion). Preferably the third side of the triangle (which faces away from the distal end of the cutting portion) is blunt, but this is not essential.

In another embodiment the cutting portion is a parallelogram shape, with two sides of the parallelogram being the first cutting side and the second cutting side (with these sides facing towards the distal end of the cutting portion). Preferably the third and fourth side of the parallelogram (which face away from the distal end of the cutting portion) are blunt, but this is not essential.

The use of a triangular or parallelogram shape means that at least part of the first cutting side and at least part of the second cutting side can angularly extend outwardly of the elongate body, providing cutting surfaces for cutting away bony ingrowth.

In one embodiment the cutting portion is an isosceles triangle, i.e. there are two sides the same length. It may be that the two sides of equal length are the first cutting side and the second cutting side (with these sides facing towards the distal end of the cutting portion). In one embodiment the cutting portion is an equilateral triangle i.e. all three sides are the same length. However, the cutting portion may also be a scalene triangle, i.e. the sides are all different lengths.

In another embodiment the cutting portion is a rhombus shape, with two sides of the rhombus being the first cutting side and the second cutting side (with these sides facing towards the distal end of the cutting portion). Preferably the third and fourth side of the rhombus (which face away from the distal end of the cutting portion) are blunt, but this is not essential.

It can be that the first cutting side and the second cutting side are the same length (or at least substantially the same length, within manufacturing tolerances). This has the benefit of providing cutting at the same angle regardless of whether the first cutting side or the second cutting side is used to cut. It also has the benefit of widening the tunnel by the same amount on both sides.

In one embodiment first cutting side and the second cutting side are at an angle to one another of from 50 to 70 degrees, such as from 55 to 70 degrees, e.g. from 60 to 65 degrees, for example about 60 degrees.

As noted above, the first cutting side and the second cutting side extend outwardly from the elongate body, allowing them to cut away bony ingrowth.

The chevron osteotome device may be a single use device.

The chevron osteotome device is suitably of one-piece construction, for example it may be formed by laser cutting.

In one embodiment the chevron osteotome device is provided with a handle. The handle suitably permits manual operation of the device, such that a surgeon can manually push the chevron osteotome device in the direction of the distal end of the implant so as to cut away bony ingrowth on both sides of the access tunnel with the first angled cutting side and the second angled cutting side.

In one embodiment the handle is an integral part of the device, for example the device plus handle may be a one-piece construction product. In another embodiment, the handle is removable.

In one embodiment, the chevron osteotome device is operated automatically rather than manually. In this embodiment the chevron osteotome device may, for example, be attached to a reciprocating saw or another reciprocating mechanism that automatically moves the device forwards and backwards in a linear fashion. Such an automated setup can therefore push the chevron osteotome device in the direction of the distal end of the implant so as to cut away bony ingrowth on both sides of the access tunnel with the first angled cutting side and the second angled cutting side, and then retract the chevron osteotome device back out from the access tunnel, and can repeat this motion as required.

Where a set of two or more osteotome devices according to the invention is used, these may differ in terms of the width of cutting portion (the maximum distance between the first cutting side and the second cutting side). Therefore within the set each osteotome device may be provided with a width of cutting portion that is slightly wider than the one that is the size below, e.g. the width may be 0.5 mm wider or more, or 1 mm wider or more, such as from 1 mm to 5 mm wider or from 1 mm to 3 mm wider.

Third Stage

The third stage of the procedure involves removing bony ingrowth located between the implant and the femur in the anterior aspect, and removing bony ingrowth located between the implant and the femur in the posterior aspect. The intention of this step is to reduce the amount of bony ingrowth between the implant and the femur in the anterior aspect and to reduce the amount of bony ingrowth between the implant and the femur in the posterior aspect.

In one embodiment, this step may clear a space at the bone-implant interface to both the medial and lateral edges of the implant.

This third stage may be carried using the curette device of the invention (or a set of two or more curette devices according to the invention).

The curette device of the invention comprises:
- an elongate body in the form of a flat plate that extends from a first elongate edge to a second elongate edge and having a distal end and a proximal end that can be provided with a handle;
- a first cutting portion located at or near the distal end which extends outwardly from a first elongate edge of the elongate body, the cutting portion having a blunt edge and a cutting edge which meet at an angled cutting point, wherein the blunt edge extends from a first location on the elongate body to the cutting point and the cutting edge extends from a second location on the elongate body to the cutting point, wherein the first location is closer to the distal end than the second location and wherein the cutting edge is at an angle to the elongate axis of the curette device of from 50 to 85 degrees;

such that the curette device can be located in an access tunnel, with its elongate axis substantially aligned with the central axis running along the length of the tunnel, and with the distal end located at or near the distal (closed) end of the access tunnel, and then can be moved such that its elongate axis is angled with respect to the central axis running along the length of the tunnel, until the cutting edge contacts bony ingrowth located between the implant and the femoral cortex, and such that the curette device can then be withdrawn from the access tunnel whilst being retained in an angled position, such that as the device is withdrawn the cutting edge cuts away bony ingrowth located between the implant and the femoral cortex.

The elongate body of the curette device suitably has a diameter that is equal to or slightly less than the diameter of the now-widened access tunnel. For example its diameter may be less than the diameter of the access tunnel by 1 mm or less, e.g. from 0.1 to 0.5 mm.

As noted above, the elongate body of the curette device is in the form of a flat plate and thus it extends from a first elongate edge to a second elongate edge.

In one embodiment, its maximum width (excluding any handle) is from 5 to 25 mm, such as from 8 to 22 mm, e.g. from 10 to 20 mm.

The elongate body need not have a constant width. In one embodiment the elongate body is tapered, having a greater width at its proximal end than its distal end.

In one embodiment, the width of the curette device when measured at the cutting point, i.e. the straight line distance from the cutting point to the second elongate edge going via the central elongate axis of the curette device, is from 4 to 18 mm, such as from 5 to 15 mm, e.g. from 6 to 12 mm.

As the elongate body is in the form of a plate, its depth (thickness) will be less than its width. In one embodiment its depth is less than or equal to half of its width. In one embodiment the depth of the plate is from 0.2 to 3 mm, such as from 0.5 to 2.5 mm, preferably from 1 to 2 mm.

The length of the elongate body may be greater than the length of the implant. For example its length may be greater than the length of the implant by 1 mm or more, such as 3 mm or more, or 5 mm or more.

The cutting edge is located towards the proximal end of the cutting portion, i.e. such that cutting occurs as the curette device is withdrawn from the tunnel rather than as it is pushed into the tunnel.

The cutting edge may be sharp along its length, such that all of the cutting edge can serve to cut away bony ingrowth located between the access tunnel and the surface of the implant. However, it will be appreciated that the device will also be effective if only some of the length of the cutting edge is sharp. In the present invention, it is only necessary that the cutting edge is sharp at its distal end, i.e. the cutting point. Therefore the cutting edge is sharp at the cutting point and is optionally sharp along some, most or all of the remainder of the cutting edge.

In some embodiments the cutting edge is sharp at said distal end and also is sharp for 10% or more of the remainder of the cutting edge, e.g. 20% or more, 30% or more, 40% or more, or 50% or more. In some embodiments the cutting edge is sharp at said distal end and is also sharp for 10% or less of the remainder of the cutting edge, e.g. 5% or less. Where portions of the cutting edge apart from the distal end are sharp, preferably these are located near to the distal end.

For example, going from the distal end towards the proximal end of the cutting edge, the first 10% or more of the length may be sharp, e.g. the first 15% or more, the first 25% or more, or the first the first 35% or more, or the first 50% or more.

The cutting edge suitably adjoins the elongate body near to the distal end of the elongate body. In one embodiment the point at which the cutting edge adjoins the elongate body is located at a distance from the distal end of from 0.5 to 20 mm, such as from 0.5 to 15 mm or from 0.5 to 10 mm; preferably it is at a distance from the distal end of from 1 to 8 mm, such as from 1.5 to 7 mm or from 2 to 6 mm, e.g. from 2.5 to 5 mm.

The cutting edge may be angled upwardly, i.e. an angle of from 30 to 89 degrees to the elongate axis of the elongate body, or may be angled downwardly, i.e. an angle of from 91 to 150 degrees to the elongate axis of the elongate body. It may also be at an angle of about 90 degree. Either permits the user of the device to angle the device whilst it is in the access tunnel so as to result in the cutting edge contacting the bony ingrowth at the edge of the tunnel, and thus permitting the bony ingrowth between the face of the implant and the femoral cortex to be scraped away.

Preferably the cutting edge is at an angle of from 30 to 60 degrees to the elongate axis of the elongate body or is at an angle of from 120 to 150 degrees to the elongate axis of the elongate body.

In one embodiment the distance from the elongate body (e.g. from its second elongate edge) to the distal end of the cutting edge, when measured in a direction that is perpendicular to the elongate axis of the elongate body, is from 3 to 10 mm, such as from 4 to 9 mm, e.g. from 5 to 8 mm.

The cutting edge may be straight or may be curved. If it is curved, its angle to the elongate axis should be seen as the angle created when considering the notional straight line between the distal end and the proximal end of the cutting edge with respect to the elongate axis.

The blunt edge may be straight or may be curved. If it is curved, its angle to the elongate axis should be seen as the angle created when considering the notional straight line between the distal end and the proximal end of the blunt edge with respect to the elongate axis.

The distal end of the elongate body may be blunt or may be sharp.

In a preferred embodiment the curette device comprises a second cutting portion, located between the second elongate edge and the distal end of the elongate body. For example, a second cutting portion may be provided on a curved or angled edge that extends between the second elongate edge and the distal end of the elongate body. The second cutting portion suitably comprises teeth. Alternatively or additionally, the second cutting portion may comprise a sharp edge.

The curette device may be a single use device.

Where a set of two or more curette devices according to the invention is used, these may differ in terms of the length of the cutting edge (distance between the distal end and the proximal end of the cutting edge) and/or in terms of the distance from the elongate body (e.g. from its second elongate edge) to the distal end of the cutting edge, when measured in a direction that is perpendicular to the elongate axis of the elongate body. Therefore within the set each curette device may be provided with such a length/distance that is slightly greater than the one that is the size below, e.g. said length/distance may be 0.5 mm greater or more, or 1 mm greater or more, such as from 1 mm to 5 mm greater.

Optional Next Stage

The optional next stage of the procedure involves removing bony ingrowth located at the distal end of the implant, to create a cavity at the distal end of the implant that extends in the medial and lateral directions. This stage may be carried out using a distal space maker device (or a set of two or more distal space maker devices). The distal space maker may be a medial-lateral cavity maker device of the type described in WO2017/032993.

The distal space maker device that may be used comprises:

an elongate body having a proximal end that is provided with a handle and a distal end that is blunt;
a cutting portion extending outwardly from the elongate body, the cutting portion being located closer to the distal end of the elongate body than the proximal end of the elongate body, the cutting portion having a connecting end attached to the elongate body and a protruding end located away from the elongate body, the connecting end and the protruding end being connected by a first edge located towards the distal end of the elongate body and a second edge located towards the proximal end of the elongate body, wherein the first edge is blunt but the second edge is a cutting edge;

such that the distal space maker device can be located in an access tunnel and rotated so as to cut away bony ingrowth with the second edge at the distal end of the implant, to create a cavity at the distal end of the implant that extends in the medial and lateral directions.

The elongate body suitably has a diameter that is equal to or slightly less than the minimum diameter of the access tunnel. For example its diameter may be less than the minimum diameter of the access tunnel by 1 mm or less, e.g. from 0.1 to 0.5 mm.

The cutting portion suitably extends in a plane that lies on the edge of the elongate body. This allows the cutting portion to be positioned parallel to the surface of the implant when the cutting portion is in a part of the access tunnel that is alongside the implant, with the cutting portion only then being rotated once the cutting portion is located beyond the distal end of the implant. This reflects the fact that the access tunnel is only widened in the second step of the procedure in a direction parallel to the surface of the implant; the dimensions of the access tunnel in all other directions remain relatively small. Therefore the extending portion of the cavity maker device, namely the cutting portion, needs to be able to be positioned in that widened dimension of the access tunnel so that it can pass down to a location beyond the distal end of the implant.

In one embodiment the cutting portion is located at the distal end of the elongate body. In another embodiment the cutting portion is located at a distance from the distal end of from 0.5 to 20 mm, such as from 0.5 to 15 mm or from 0.5 to 10 mm; preferably it is at a distance from the distal end of from 1 to 8 mm, such as from 1.5 to 7 mm or from 2 to 6 mm, e.g. from 2.5 to 5 mm.

The cutting portion has an upper surface and a lower surface linking the first edge and the second edge. These surfaces may suitably be substantially flat. These surfaces are suitably blunt.

The cutting portion is such that in use the first edge is a curved edge that is convex and the second edge is a curved edge that is concave. The cutting portion may overall have a hook shape.

It may be that the cutting portion has a fixed shape that is curved. In particularly it may have a fixed hook shape that curves upwardly (that is, towards the proximal end rather than the distal end).

In another embodiment the cutting portion is only formed into a curved shape in situ. For example, the cutting portion may be formed from a plurality (e.g. three or more, such as from three to twenty, or from three to ten) of hinged sections that can flex in an upward direction (that is, towards the proximal end rather than the distal end) and which therefore can form a curved shape when they are located at the distal end of the implant. In one embodiment, the hinged sections may be linked by a tension wire which can be shortened in order to increase the tension and urge the hinged sections upwardly. The hinged sections may be universal joints.

In this embodiment preferably the cutting portion is formed from a plurality (e.g. three or more, such as from three to twenty, or from three to ten) of hinged sections that can only flex in an upward direction (that is, towards the proximal end rather than the distal end). Thus there is no movement in other directions.

In one embodiment the cutting portion is replaceably secured to the elongate body, therefore allowing the cutting portion to be removed and replaced when the cutting edge is not sharp enough for continued use.

In another embodiment the cutting portion is not replaceable and therefore the distal space maker device is simply disposed of once the cutting edge is not sharp enough for continued use.

When a set of two or more distal space maker devices according to the invention is used, these may differ in terms of the width of cutting portion (distance between the elongate body and the outermost point of the second edge of the cutting portion). Therefore within the set each distal space maker device may be provided with a width of cutting edge portion that is slightly wider than the one that is the size below, e.g. the width may be 0.5 mm wider or more, or 1 mm wider or more, such as from 1 mm to 5 mm wider.

Fourth Stage

The fourth stage of the procedure involves removing bony ingrowth located at the antro-lateral edge of the implant, at the antro-medial edge of the implant, at the postro-lateral edge of the implant and at the postro-medial edge of the implant. The intention of this step is to remove bony ingrowth from sections of both the medial and lateral aspects of the implant. Therefore the medial surface of the implant is cleared of bony ingrowth at or near to where it adjoins the anterior surface of the implant and at or near to where it adjoins the posterior surface of the implant. The lateral surface of the implant is cleared of bony ingrowth at or near to where it adjoins the anterior surface of the implant and at or near to where it adjoins the posterior surface of the implant. This stage may be carried out using the medial-lateral clearance device of the invention (or a set of two or more medial-lateral clearance devices according to the invention).

The medial-lateral clearance device of the invention comprises:

an elongate body having a proximal end that can be provided with a handle and having a distal end, the elongate body being in the shape of a flat plate that extends from a first elongate edge to a second elongate edge;

a cutting portion extending outwardly from the elongate body and located at or near the distal end, the cutting portion having an inner surface that is flat and which connects with the first elongate edge of the elongate body at a substantially 90 degree angle, and having an outer surface that comprises an angled cutting face that is located towards the distal end of the elongate body, wherein the inner surface meets the angled cutting face at a cutting edge, at an angle of from 20 to 70 degrees;

such that the distal end of the flat plate elongate body can be located in a space at the bone-implant interface, at or near to the shoulder portion of the implant, with the flat plate being parallel to either the anterior surface or the posterior surface, and with the flat inner surface of the cutting portion aligned with either the medial or lateral surface of the implant, such that the medial-lateral clearance device can then be pushed in the direction of the distal end of the implant, with the flat plate elongate body remaining alongside the respective anterior or posterior surface, in the space at the bone-implant interface, whilst the angled cutting face cuts away bony ingrowth located at said medial or lateral surface of the implant as the device is pushed towards the distal end of the implant.

The inner surface of the cutting portion connects with the first elongate edge of the elongate body at a substantially 90 degree angle. A substantially 90 degree angle may, for example, be from 85 to 105 degrees or from 85 to 100 degrees, such as from 88 to 100 degrees or from 89 to 100 degrees or from 90 to 100 degrees.

In one embodiment the inner surface is flat across its entire surface and this flat surface meets the angled cutting face at a cutting edge, at an angle of from 20 to 70 degrees. In another embodiment, the inner surface comprises an angled portion that is located towards the distal end of the elongate body, such that the angled portion of the inner surface meets the angled cutting face at a cutting edge, at an angle of from 20 to 70 degrees.

In one embodiment, all of the outer surface is angled. In one such embodiment, the outer surface is a single angled surface that forms the angled cutting face. Thus the outer surface can consist essentially of the angled cutting face.

However, in a preferred embodiment, the outer surface comprises a flat portion as well as the angled cutting face. It will be appreciated that the angled cutting face must be located towards the distal end of the elongate body and must meet the inner surface towards the distal end of the elongate body, i.e. such that cutting occurs as the device is pushed towards the distal end of the implant. Therefore any flat portion of the outer surface is located towards the proximal end.

In one embodiment, when considering the length of the cutting portion as being the distance along which it connects with the first elongate edge of the elongate body, 25% or more of the length of the cutting portion is made up of the angled cutting face, such as 30% or more or 40% or more, e.g. from 30 to 100% or from 30 to 80% or from 40 to 70% or from 40 to 60%. The remainder is suitably a flat portion. In one embodiment, about half of the length of the cutting portion is the angled cutting face and about half is a flat portion.

In the present invention the flat inner surface of the cutting portion meets the angled cutting face of the cutting portion at a cutting edge, at an angle of from 20 to 70 degrees. In one embodiment the angle of the cutting edge is from 25 to 65 degrees, or from 30 to 60 degrees, such as from 35 to 55 degrees. In a preferred embodiment the angle of the cutting edge is from 40 to 50 degrees, such as about 45 degrees. Essentially these ends are chisels; however the end also could be an osteotome where the sharp edge meets in the mid-line.

The elongate body of the medial-lateral clearance device is a flat plate that suitably has a maximum width (excluding any handle) from 5 to 50 mm, such as from 8 to 40 mm or from 10 to 30 mm, e.g. from 15 to 25 mm.

The elongate body of the medial-lateral clearance device may suitably taper from a wider proximal end to a narrower distal end. Therefore in one embodiment the maximum width is at the proximal end. The handle may optionally be wider than the distal end.

In one embodiment the width at the distal end is from 2 to 30 mm, such as from 3 to 20 mm or from 4 to 15 mm, e.g. from 5 to 10 mm.

As the elongate body is in the form of a plate, its depth (thickness) will be less than its width. In one embodiment its depth is less than or equal to half of its minimum width, e.g. the width at the distal end. In one embodiment the depth of the plate is from 0.2 to 3 mm, such as from 0.5 to 2.5 mm, preferably from 1 to 2 mm.

The distal end of the elongate body may be blunt or may be sharp. Thus in one embodiment the distal end of the elongate body may present a further cutting edge.

The elongate body may, in one embodiment, have a distal end that is curved. Alternatively, the distal end may be flat, or may be angled.

The cutting portion extends outwardly from the elongate body at or near the distal end of the elongate body. In this regard, the point at which the cutting edge adjoins the elongate body may, for example, be located at a distance from the distal end of from 1 to 20 mm, such as from 1.5 to 15 mm or from 1.5 to 10 mm; preferably it is at a distance from the distal end of from 2 to 10 mm, such as from 2 to 9 mm or from 2.5 to 8 mm, e.g. from 3 to 7 mm.

The cutting edge may have any suitable length. In one embodiment its width is from 1.5 to 6 mm, such as from 2 to 5 mm or from 2.5 to 4 mm, e.g. about 3 mm.

In one embodiment the distance from the first elongate edge of the elongate body to the outermost tip of the cutting edge, when measured in a direction that is perpendicular to the elongate axis of the elongate body, is the same or substantially the same (e.g. within ±5%, or within manufacturing tolerances) as the width of the flat plate elongate body.

The cutting edge may be angled upwardly, e.g. at an angle of from 20 to 70 degrees to the elongate axis of the elongate body; preferably from 30 to 60 degrees to the elongate axis of the elongate body, such as from 40 to 50 degrees.

The cutting edge may be straight or may be curved. If it is curved, its angle to the elongate axis should be seen as the angle created when considering the notional straight line between the distal end and the proximal end of the cutting edge with respect to the elongate axis.

As the cutting portion is in the form of a plate, its depth (thickness) will be less than its width. In one embodiment the depth of the plate is from 0.2 to 2 mm, such as from 0.5 to 1.5 mm, preferably from 1 to 1.5 mm.

In one embodiment the cutting portion is replaceably secured to the elongate body, therefore allowing the cutting portion to be removed and replaced when the cutting edge is not sharp enough for continued use.

In another embodiment the cutting portion is not replaceable and therefore the medial-lateral clearance device is simply disposed of once the cutting edge is not sharp enough for continued use.

As noted above, there would normally be provided a "left handed" and a "right handed" version of the device, i.e. a medial-lateral clearance device where the flat plate cutting portion is ninety degrees clockwise from the flat plate elongate body and a medial-lateral clearance device where the flat plate cutting portion is ninety degrees anticlockwise from the flat plate elongate body.

Preferably, therefore, a medial-lateral clearance kit is provided that comprises one or more medial-lateral clearance device where the flat inner surface is ninety degrees clockwise from the flat plate elongate body and one or more medial-lateral clearance device where the flat inner surface is ninety degrees anticlockwise from the flat plate elongate body.

In addition, a set of two or more different sized devices according to the invention may be used. Thus for both the "left handed" and the "right handed" version, two or more different sizes may be provided. These may suitably differ in terms of the length of the cutting edge (distance between the distal end and the proximal end of the cutting edge). Therefore within the set each "left handed" and each "right handed" version may be provided with a length of cutting edge that is greater than the one that is the size below, e.g. the length of cutting edge may be 1 mm more than the size below, or 2 mm more, such as from 1 mm to 5 mm longer.

Therefore the smallest size of cutting edge can be used first, e.g. that may be 1 mm to 4 mm long, such as 3 mm. Then a larger size of cutting edge may be used, e.g. that may be 4 mm to 7 mm long, such as 5 mm or 6 mm. There may be two different sizes, or three different sizes, or more.

Optional Fifth Stage—Clearance of Medial Aspect of a Collared Implant

In the situation where the implant is collared, the collar will restrict the access that can be achieved by the medial-lateral clearance device. Specifically, the presence of a collar on the medial side at the shoulder, which usually extends from the medial border of the shoulder to halfway laterally, will prevent the clearance of the medial surface of the implant using the medial-lateral clearance device of the invention.

Therefore in one embodiment, the invention further comprises a fifth step of clearing the medial aspect of a collared implant.

This may be carried out using a wire delivery device according to the invention.

The wire delivery device of the invention comprises:
  a first elongate body that extends from a first elongate edge to a second elongate edge and having a proximal end that can be provided with a handle and a distal end that is blunt, where there is a first wire guidance slot provided in a spaced relationship with the distal end and located within the first elongate body, wherein the wire guidance slot runs from an entrance at the first elongate edge to an exit at the second elongate edge, wherein the distance between the entrance and the distal end is greater than the distance between the exit and the distal end, such that the first wire guidance slot is at an angle to the elongate axis of the body;

a second elongate body that extends from a first elongate edge to a second elongate edge and having a proximal end that can be provided with a handle and a distal end that is blunt, where there is a second wire guidance slot provided in a spaced relationship with the distal end and located within the second elongate body, wherein the wire guidance slot runs from an entrance at the first elongate edge to an exit at the second elongate edge, wherein the distance between the entrance and the distal end is greater than the distance between the exit and the distal end, such that the second wire guidance slot is at an angle to the elongate axis of the body;

such that a wire can be fed through and extend between the first wire guidance slot and the second wire guidance slot, and the elongate bodies can be positioned in a spaced apart but aligned configuration with their second elongate edges closest to one another, so that the wire extends into the space between the elongate bodies at an angle, whereby the wire can be pulled taught between the two elongate bodies and can then be used to cut by pulling the first and second elongate bodies in an alternating motion or by pushing the first and second elongate bodies in an alternating motion.

In one embodiment, the first wire guidance slot is at an angle of 120 to 140 degrees (e.g. about 130 to 140 degrees) to the elongate axis of the body and the second wire guidance slot is at an angle of 120 to 140 degrees (e.g. about 130 to 140 degrees) to the elongate axis of the body.

In one embodiment, the first elongate body is in the form of a flat plate and the second elongate body is in the form of a flat plate.

The first and second elongate bodies are suitably the same size and shape. They can be considered as left and right hand versions of each other.

The wire delivery device can be operated manually or the first and second elongate bodies can be attached to a reciprocating saw or another reciprocating mechanism that automatically moves the device forwards and backwards in a linear fashion.

Each of the first and second elongate bodies is a flat plate that suitably has a maximum width (excluding any handle and handle receiving portion) from 4 to 10 mm, such as from 5 to 9 mm or from 6 to 8 mm, e.g. about 7 mm.

The elongate bodies may have a substantially constant width or they may taper from a wider proximal end to a narrower distal end. Therefore in one embodiment the maximum width is at the proximal end.

In one embodiment the width at the distal end is from 5 to 9 mm or from 6 to 8 mm, e.g. about 7 mm.

As the elongate body is in the form of a plate, its depth (thickness) will be less than its width. In one embodiment its depth is less than or equal to half of its minimum width, e.g. the width at the distal end. In one embodiment the depth of the plate is from 0.2 to 3 mm, such as from 0.5 to 2.5 mm, preferably from 1 to 2 mm, e.g. about 1 mm.

The elongate body may suitably have a length of from 100 to 200 mm, e.g. from 150 to 200 mm, such as about 180 mm.

The wire guidance slot has a width sufficient to receive the wire. Therefore it will usually correspond substantially to the diameter of the wire. In one embodiment it is from 0.3 to 1.5 mm, e.g. from 0.5 to 1.2 mm and especially from 0.6 to 1 mm.

The wire is secured in the wire guidance slot, e.g. by welding. It is secured such that it extends outwardly from the wire guidance slot towards the direction of the second elongate edge. It follows the alignment of the wire guidance slot and therefore it is angled towards the proximal end, at an angle of from 120 to 140 degrees.

When the wire is fed through and extends between the first wire guidance slot and the second wire guidance slot, it will be secured in these guidance slots. This may suitably be by welding. It will be appreciated that when the elongate bodies are positioned in a spaced apart but aligned configuration, with their second elongate edges adjacent to one another, they can be moved closer together to make the wire slack and can be moved apart to make the wire taught.

The wire is preferably a Gigli wire.

When using the wire delivery device of the invention, the wire is pulled taught between the two elongate bodies. It is then wrapped around the shoulder of the implant at a medial location beneath the collar, and the first and second elongate bodies can be pulled in an alternating motion to cause the wire to cut through the medial part of the femur beneath the shoulder. This can be continued until the wire comes to rest on the medial aspect of the implant proximally.

The two elongate bodies can then be threaded anteriorly and posteriorly in relation to the implant into the space that has already been created by the previous steps.

The sloped distal ends of the two elongate bodies will sit on the lateral aspect of the inner cortex of the femur, both anteriorly and posteriorly. The wire will not be directly exposed to the bone because it is secured in the wire guidance slots and these are spaced from the distal end. The blunt distal end therefore protects the wire from the bone.

The first and second elongate bodies can then be pushed in an alternating motion to cause the wire to cut, directing the force distally. As the wire traverses distally it will clear the bone-implant interface medially. The distal movement of the first and second elongate bodies may be carried out manually, or a reciprocating mechanism could be used to drive each of the first and second elongate bodies.

It may be that the wire delivery device of the invention comprises:

a first elongate body in the form of a flat plate that extends from a first elongate edge to a second elongate edge and having a proximal end that can be provided with a handle and a distal end that is blunt, wherein the distal end is sloped from the first elongate edge to the second elongate edge at an angle to the elongate axis of the body of from 120 to 140 degrees, and where there is a first wire guidance slot provided in a spaced relationship with the distal end, the wire guidance slot running substantially parallel to the sloped distal end;

a second elongate body in the form of a flat plate that extends from a first elongate edge to a second elongate edge and having a proximal end that can be provided with a handle and a distal end that is blunt, wherein the distal end is sloped from the first elongate edge to the second elongate edge at an angle to the elongate axis of the body of from 120 to 140 degrees, and where there is a second wire guidance slot provided in a spaced relationship with the distal end, the wire guidance slot running substantially parallel to the sloped distal end;

such that a wire can be fed through and extend between the first wire guidance slot and the second wire guidance slot, and the elongate bodies can be positioned in a spaced apart but aligned configuration with their second elongate edges closest to one another, so that the wire extends into the space between the elongate bodies at an angle of from 120 to 140 degrees,
whereby the wire can be pulled taught between the two elongate bodies and can then be used to cut the bone-implant interface by pulling the first and second elongate bodies in an alternating motion or by pushing the first and second elongate bodies in an alternating motion.

In this embodiment it may be preferred that the flat plate elongate bodies are each provided with handles that extend out of the plane of the flat plate, to assist ease of control. Each of the first and second elongate bodies may include a handle receiving portion that extends from the proximal end. This may, for example, be circular or oval in shape. The handle receiving portion has a handle extending outwardly therefrom, at 90 degrees to the flat plate. The handle may be permanently attached to the handle receiving portion or may be releasably secured thereto. There may, for example, be a recess provided in the handle receiving portion into which a handle can be securely received. The recess may in one embodiment be a square or rectangular shape.

In this embodiment the distal end of each body is sloped from its first elongate edge to its second elongate edge at an angle to the elongate axis of the body of from 120 to 140 degrees, such as from 130 to 140 degrees, ideally 135 degrees.

In this embodiment in each elongate body there is a wire guidance slot provided in a spaced relationship with the distal end, the wire guidance slot running substantially parallel to the sloped distal end. Therefore the wire guidance slot is likewise at an angle to the elongate axis of the body of from 120 to 140 degrees, such as from 130 to 140 degrees, ideally 135 degrees.

In this embodiment the distance between the distal end and the wire guidance slot is suitably from 0.5 to 4 mm, such as from 0.5 to 3 mm or from 1 to 2 mm, e.g. about 1 mm.

In this embodiment the wire guidance slot is rectangular in shape, with its length running substantially parallel to the distal end.

In this embodiment the wire guidance slot may suitably extend for a length of about 25 to 75% of the width of the distal end. In one embodiment the wire guidance slot has a length of from 1 to 4 mm wide, e.g. from 1 to 3 mm and especially from 2 to 3 mm.

Kit

It will be appreciated that a surgical kit may be provided that comprises any combination of two or more of the novel items discussed above.

Thus there may be provided a kit comprising two or more of (and in particular three or more of, or four or more of, or all of):
  a targeting device of the invention
  an osteotome device of the invention
  a curette device of the invention
  a medial-lateral clearance device of the invention
  a wire delivery device of the invention.

There may be provided a kit comprising two or more of (and in particular three or more of, or four or more of, or five or more of, or all of):
  a targeting device of the invention
  a chevron chisel of the invention
  an osteotome device of the invention
  a curette device of the invention
  a medial-lateral clearance device of the invention
  a wire delivery device of the invention.

There may be provided a kit comprising two or more of (and in particular three or more of, or all of):
  a targeting device of the invention
  a chevron chisel of the invention
  a curette device of the invention
  a medial-lateral clearance device of the invention.

In such a kit, all of the cutting devices may, in one embodiment, have a thickness of about 1 mm.

It may be that where the surgical kit includes the targeting device, this is provided in combination with an external targeting device, as described above.

It may be that where the surgical kit includes the targeting device, this is provided in combination with a medial targeting device and an external targeting device, as described above.

It may be that where the surgical kit includes the osteotome device, this is in the form of a set of osteotome devices having different sizes, as described above.

It may be that where the surgical kit includes the medial-lateral clearance device, this is in the form of a pair of "left handed" and "right handed" devices as described above. Further, it may be that this is in the form of a set of different sized devices, with there being two or more different sizes for the "left handed" device and two or more different sizes for the "right handed" device.

The kit may include one or more brace sleeve. The brace sleeve can be used to provide structural support for the elongate body of any of the devices included in the kit, except for the targeting device which it will be appreciated does not have an elongate body.

The brace sleeve may comprise two elongate faces which are joined at one elongate edge and are open at the opposite elongate edge and at both the two ends, so as to create an elongate cavity between the two faces within which an elongate body can be slidably received. The brace sleeve can slide onto and over an elongate body to provide additional strength and resistance to bending during use. The brace sleeve can cover some, most or all of the length of an elongate body of any of the devices described above.

The two elongate faces may be flat and parallel to one another. However, in one embodiment, one of the elongate faces flares outwardly towards the open elongate edge. This can assist with ease of placing the brace sleeve onto the elongate body, because it means that the open "mouth" of the brace sleeve is larger than the closed edge.

The kit may include multiple brace sleeves. These may all be the same or they may be different. For example, there may be brace sleeves of different lengths provided.

The kit may include a universal handle. A universal handle can be used as a handle for two or more of the devices described above, except for the targeting device which it will be appreciated does not require a handle. The universal handle may comprise a body having one or more grip portions at its proximal end and an engagement recess, such as a slot, at its distal end. The engagement recess is sized and shaped to receive the proximal end of the devices described above, except for the targeting device. In this regard, it will be appreciated that said devices may each be provided with a proximal end having the same size and shape, e.g. a flat plate, and the engagement recess of the universal handle is sized and shaped to receive this proximal end. In one embodiment, all of the devices included in the kit apart from the targeting device have the same size and shape of distal end, and thus the universal handle can be used as the handle for all of these devices.

In a preferred embodiment the proximal end of the device comprises a neck and an enlarged head, and the universal handle is provided with a locking cap which fits over the distal end of the body and permits the enlarged head to be locked in place in the engagement recess. In particular, the locking cap is provided with a dual slot, comprising a first elongate shaped slot that can receive the enlarged head and allow it to pass therethrough, and a second elongate shaped slot that can receive the neck and allow it to pass therethrough but that is too small to allow the enlarged head to pass therethrough. The first elongate shaped slot and the second elongate shaped slot overlap, with the elongate axis of the first elongate shaped slot being at an angle α to the elongate axis of the second elongate shaped slot. Therefore the locking cap can be placed over the distal end of the body with the first elongate shaped slot aligned with the engagement recess and the enlarged head can pass through the first elongate shaped slot and into the engagement recess, and the locking cap can then be rotated by angle α such that the second elongate shaped slot is aligned with the engagement recess, meaning that the enlarged head is locked into the engagement recess because it is too big to pass through the second elongate shaped slot. When it is desired to release the universal handle from the device, the locking cap can be rotated until the first elongate shaped slot is aligned with the engagement recess again.

It may be that the locking cap is spring loaded to assist with release. Therefore a torsion spring may be provided between the body and the locking cap, which biases the locking cap away from the body. The user can overcome that biasing force by pushing the locking cap onto the body. The locking cap can be held in place by the use of a securing means that connects the locking cap and the body, e.g. a locking pin received by an aperture.

DESCRIPTION OF THE DRAWINGS

The invention will now be further described with reference to the drawings, which are exemplary of the invention rather than limiting, and in which:

FIG. 2a is a front perspective view of the anterior guide member of a targeting device of the invention FIG. 2b is a front perspective view of the engagement member of a targeting device of the invention FIG. 2c is a front perspective view of the posterior guide member of a targeting device of the invention FIG. 2d is a side perspective view of the anterior guide member of a targeting device of the invention FIG. 2e is a cross section of the anterior guide member of a targeting device of the invention, showing the angled channel FIG. 2f is a cross section of the posterior guide member of a targeting device of the invention, showing the angled channel FIG. 2g is a side perspective view of the posterior guide member of a targeting device of the invention FIG. 3a is a perspective view of the osteotome device of the invention FIG. 3b is a side view of an osteotome device of the invention FIG. 3c is a plan view of an osteotome device of the invention FIG. 3d is a detailed view of the osteotome device shown in FIG. 3c FIG. 3e is a plan view of an alternative osteotome device of the invention FIG. 4a is a side view of a curette device of the invention FIG. 4b is a plan view of a curette device of the invention FIG. 4c is a detailed view of the curette device shown in FIG. 4b FIG. 4d is a plan view of an alternative curette device of the invention FIG. 7a is a perspective view of a targeting device of the invention, together with a medial targeting device FIG. 7b is a side view of a targeting device of the invention FIG. 7c is a cut through view of a targeting device of the invention FIG. 7d is a perspective view of a targeting device of the invention, together with a medial targeting device and a key FIG. 8a is a side view of a targeting device of the invention, located on a femoral implant, and together with a medial targeting device FIG. 8b is a perspective view of a targeting device of the invention, located on a femoral implant, and together with a medial targeting device FIG. 8c is a front view of a targeting device of the invention, located on a femoral implant, and together with a medial targeting device FIG. 9a is a perspective view of a targeting device of the invention, together with a medial targeting device and a key FIG. 9b is a top view of a targeting device of the invention, together with a medial targeting device FIG. 9c is a side view of a targeting device of the invention FIG. 9d is a perspective view of the engagement member of a targeting device of the invention FIG. 10a is a perspective view of an external targeting device of the invention FIG. 10b is a side view of an external targeting device of the invention FIG. 11a is a plan view of a medial-lateral clearance device of the invention FIG. 11b is a side view of the medial-lateral clearance device of the invention FIG. 11c is a cross sectional view of the distal end of the medial-lateral clearance device of FIG. 11b FIG. 11d is a perspective view of the distal end medial-lateral clearance device FIG. 12 is a perspective view of a brace sleeve of the invention FIG. 13a is a perspective view of a universal handle of the invention FIG. 13b is an exploded perspective view of a universal handle of the invention FIG. 13c is a top view of a universal handle of the invention FIG. 14a is a side view of a wire delivery device of the invention FIG. 14b a plan view of a wire delivery device of the invention FIG. 14c is a side view of a wire delivery device of the invention FIG. 15a is a plan view of a chevron chisel of the invention FIG. 15b is a side view of a chevron chisel of the invention FIG. 15c is a perspective view of the distal end of a chevron chisel of the invention.

Figure 1E:
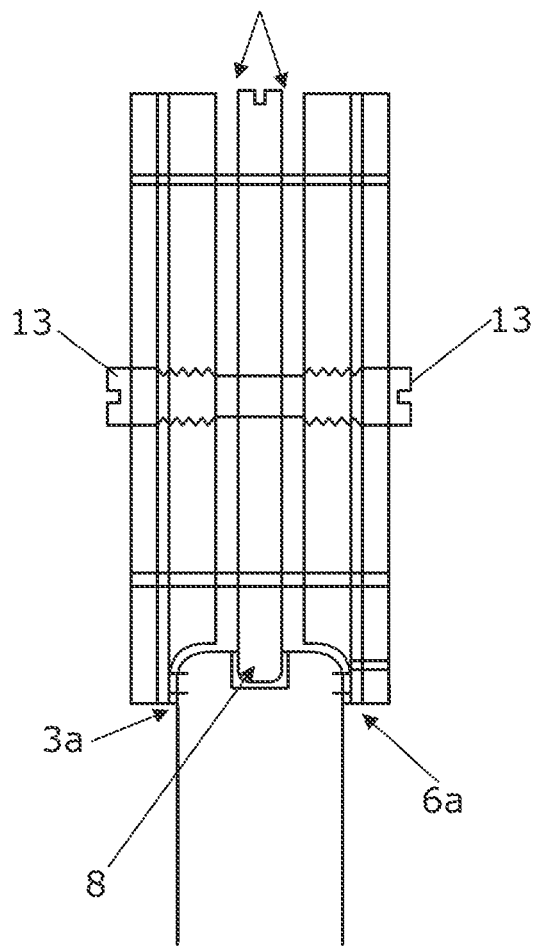
FIG. 1e is a side (lateral) view of a targeting device of the invention, located on a larger sized femoral implant than shown in FIG. 1a FIG. 1f is a front view of the engagement member of a targeting device of the invention

Embodiments of the targeting device of the invention are shown in FIGS. 1a-h, FIGS. 2a-g, FIGS. 7a-d, FIGS. 8a-c and FIGS. 9a-d.

The targeting device comprises an anterior guide member 1. This comprises a first elongate body provided with a first angled channel 2 therein, running from an entrance 2a at the proximal end of the guide member to an exit 2b at the distal end of the guide member. The first angled channel is at an angle in the range of from 1 to 3 degrees (e.g. 1 to 2.5 degrees) to the elongate axis of the elongate body, ideally 2 degrees or 2.5 degrees or 3 degrees.

The first elongate body also has a first contact element in the form of a leg 3 at its distal end for contacting the shoulder of the femoral implant and for distancing the exit from the shoulder of the implant. In some embodiments (see FIG. 1e) the leg can include perpendicularly extending prongs 3a which can contact and protrude into the surface of the shoulder of the femoral implant, to provide a secure engagement.

The targeting device also comprises a posterior guide member 4, which comprises a second elongate body provided with a second angled channel 5 therein, running from an entrance 5a at the proximal end of the guide member to an exit 5b at the distal end of the guide member. The second angled channel is at an angle in the range of from 1 to 3 degrees (e.g. 1 to 2.5 degrees) to the elongate axis of the elongate body, ideally 2 degrees or 2.5 degrees or 3 degrees.

The posterior elongate body also has a second contact element in the form of a leg 6 at its distal end for contacting the surface of the shoulder of the implant and for distancing the exit from the shoulder of the implant. In some embodiments (see FIG. 1e) the leg can include perpendicularly extending prongs 6a which can contact and protrude into the surface of the shoulder of the femoral implant, to provide a secure engagement.

Different designs of targeting device can be envisaged in terms of the number and location of the angled channels. FIGS. 1a, 2e and 2f show one design. FIG. 1d shows another design. FIGS. 7a-d and 8a-c show yet another design. FIGS. 9a-d shows a yet further design. The invention is also not limited to these illustrated designs.

In some embodiments, there is a single angled channel 2 with entrance 2a in the anterior guide member and a single angled channel 5 with entrance 5a in the posterior guide member. For example, the angled channels may each have a circular cross section. This is shown in FIGS. 1a, 2e and 2f.

In some embodiments, there are two angled channels 2 with entrance 2a in the anterior guide member and two angled channels 5 with entrance 5a in the posterior guide member. For example, the angled channels may each have a circular cross section. The angled channels in the anterior guide member may be co-joined and the angled channels in the posterior guide member may be co-joined. This is shown in FIGS. 9a and 9b.

In some embodiments, there are three angled channels 2 with entrance 2a in the anterior guide member and three angled channels 5 with entrance 5a in the posterior guide member. For example, there may be one channel having a rectangular cross section and two having a circular cross section in each of the anterior guide member and the posterior guide member. The angled channels in the anterior guide member may be co-joined and the angled channels in the posterior guide member may be co-joined. This is shown in FIGS. 7a, 7d and 8b.

The targeting device may optionally also include receiving channels 2c, 5c, for receiving the anterior guide member interlocking component 705 and the posterior guide member interlocking component 706 of the external targeting device as shown in FIGS. 10a-b and described below.

In this embodiment, the targeting device includes a first receiving channel 2c adjacent to the first angled channel 2 and aligned therewith and includes a second receiving channel 5c adjacent to the second angled channel 5 and aligned therewith. The anterior guide member interlocking component 705 and the posterior guide member interlocking component 706 are then received in these channels respectively. The first and second receiving channels 2c, 5c are shown as circular in cross section and these may each have a diameter of from 2 to 4 mm, such as about 3 mm. However, other shapes could be envisaged, e.g. they could have a square cross section, and likewise other sizes could be envisaged. The first and second receiving channels 2c, 5c may be blind channels and may, for example, extend for a depth of from 25 to 40 mm, such as about 30 mm.

The targeting device also comprises an engagement member 7 for locating and engaging the targeting device on the shoulder of the implant. This comprises an elongate body with an engagement protrusion 8 at its distal end. The engagement protrusion 8 can be received in a recess portion R on the shoulder of the implant. The elongate body of the engagement member can be located between and aligned with the elongate body of the anterior guide member 1 and the elongate body of the posterior guide member 4, such that the elongate axes of the elongate bodies are substantially aligned, and with the angled channels 2, 5 converging in the direction of the distal end, ideally at a convergence angle of 4 to 6 degrees, e.g. 4 degrees.

Figure 1F:
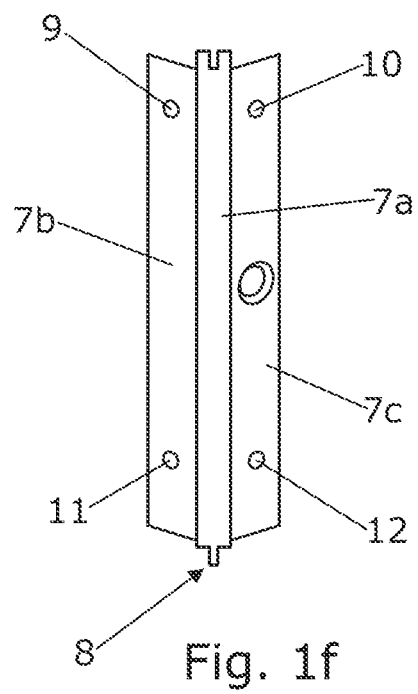
FIG. 1a is a side (lateral) view of a targeting device of the invention, located on a femoral implant
FIG. 1b is a front view of a targeting device of the invention, located on a femoral implant
FIG. 1c is a top view of a targeting device of the invention
FIG. 1d is a perspective view of a channel providing unit for use in the targeting device of the invention
FIG. 1g is a side view of the engagement member of a targeting device of the invention
FIG. 1h is a cross sectional view of the engagement member of a targeting device of the invention
Figure 1G:
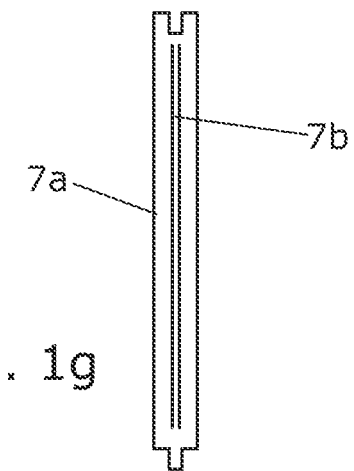
Figure 1H:
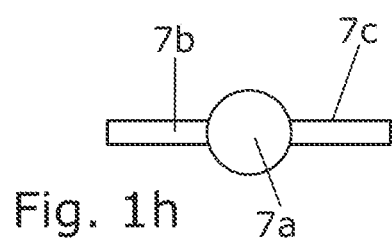
Figure 5D:
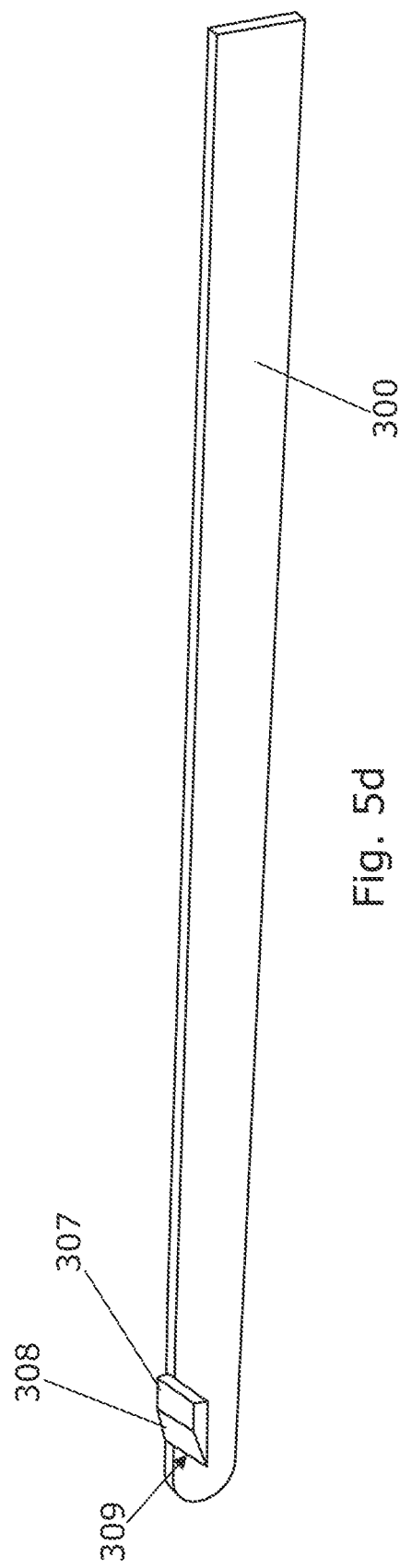
FIG. 5a is a side view of a medial-lateral clearance device of the invention
FIG. 5b is a plan view of the medial-lateral clearance device of the invention
FIG. 5c is a cross sectional view of the distal end of the medial-lateral clearance device of FIG. 5a FIG. 5d is a perspective side view of the medial-lateral clearance device, without the handle included
FIG. 5e is another perspective side view of the medial-lateral clearance device, without the handle included
Figure 5E:
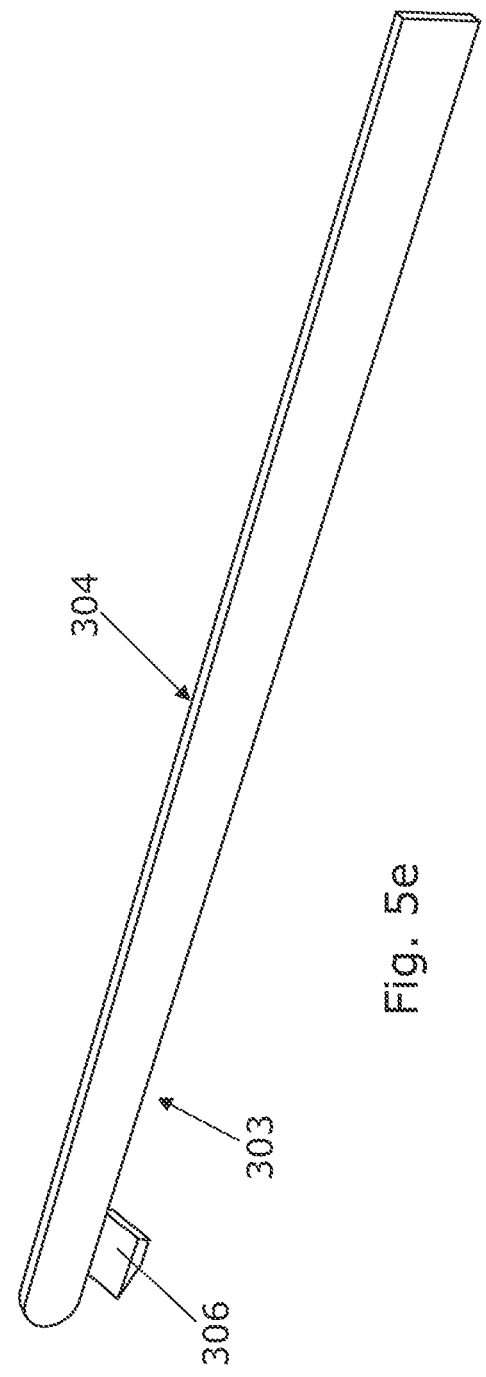

The elongate body of the engagement member may, in one embodiment, comprise a central locking rod 7a, a medial elongate wing 7b and a lateral elongate wing 7c (see FIGS. 1f, 1g, 1h).

In another embodiment the elongate body of the engagement member 7 may be substantially block-shaped. It may be that the block includes a rod 14 extending therethrough, with the distal end of the rod providing the engagement protrusion 8 (see FIG. 2b and FIGS. 7b, 7d and 9a, 9c).

Different designs of targeting device can be envisaged in terms of the number and location of the connector rails.

FIGS. 1*a-h* and 2*a-g* show one design. FIGS. 7*a-d* and 8*a-c* show another design. FIGS. 9*a-d* show a yet further design. The invention is also not limited to these illustrated designs.

In one embodiment (as shown in FIGS. 1*a-h* and 2*a-g*) the targeting device comprises a pair of parallel proximal connector rails 9, 10 and a pair of parallel distal connector rails 11, 12 (see FIGS. 1*a-h*). Each proximal connector rail can slideably connect the anterior guide member and the posterior guide member via the engagement member, with the connector rails being received in proximal connection bores 9*a*, 10*a* in the anterior guide member and the posterior guide member (see FIGS. 2*a-g*). Each distal connector rail can slideably connect the anterior guide member and the posterior guide member via the engagement member, with the connector rails being received in distal connection bores 11*a*, 12*a*, in the anterior guide member and the posterior guide member (see FIGS. 2*a-g*).

The pair of parallel proximal connector rails 9, 10 and the pair of parallel distal connector rails 11, 12 are fixedly secured to the engagement member 7.

In the embodiment shown in FIG. 1*e*, one of the pair of parallel proximal connector rails 9 is attached to, or integral with medial elongate wing 7*b* and the other one of the pair of parallel proximal connector rails 10 is attached to, or integral with lateral elongate wing 7*c*, whilst one of the pair of parallel distal connector rails 11 is attached to, or integral with medial elongate wing 7*b* and the other one of the pair of parallel distal connector rails 12 is attached to, or integral with lateral elongate wing 7*c*.

In another embodiment, the targeting device comprises a first pair of parallel connector rails 509, 510, which comprises one proximal rail 509 and one distal rail 510 (see FIGS. 7*a-d*).

The pair of parallel connector rails 509, 510 is located at or near the midpoint between the medial face of the guide members and the lateral face of the guide members.

The connector rails are slidably secured to the engagement member. Therefore the proximal connector rail 509 is received in proximal connection bores in the anterior guide member, in the engagement member, and in the posterior guide member, whilst the distal connector rail 510 is received in distal connection bores in the anterior guide member, in the engagement member, and in the posterior guide member (see FIGS. 7*b*, 7*c*).

In yet another embodiment, the targeting device comprises a first pair of parallel connector rails 609, 610, which comprises one proximal rail 609 and one distal rail 610, and a second pair of parallel connector rails 611, 612, which comprises one medial rail 611 and one lateral rail 612 (see FIGS. 9*a-d*).

The first pair of parallel connector rails 609, 610 is located at or near the midpoint between the medial face of the guide members and the lateral face of the guide members. The second pair of parallel connector rails 611, 612 is located at or near the midpoint between the proximal end of the guide members and the distal end of the guide members.

The connector rails are slidably secured to the engagement member. Therefore the proximal connector rail 609 is received in proximal connection bores in the anterior guide member, in the engagement member, and in the posterior guide member, whilst the distal connector rail 610 is received in distal connection bores in the anterior guide member, in the engagement member, and in the posterior guide member (see FIG. 9*c*). The medial connector rail 611 is received in medial connection bores provided on the anterior guide member, on the engagement member, and on the posterior guide member, whilst the lateral connector rail 612 is received in lateral connection bores provided on the anterior guide member, on the engagement member, and on the posterior guide member (see FIG. 9*a*, 9*b*).

As shown in FIGS. 8*a* and 9*b* each connector rail may be provided with a spring 550 around its outer circumference that serves to bias the anterior guide member 1 and the posterior guide member 4 into their release positions. The biasing force of the spring 550 can be overcome by use of the adjustment system 13 (as described further below) to move the anterior guide member and the posterior guide member into their holding positions.

The targeting device also comprises an adjustment system, which may be a double ended screw 13 that can adjust the distance between the elongate body of the anterior guide member 1 and the elongate body of the engagement member 7, so as to move the anterior guide member between a release position and a holding position and can simultaneously adjust the distance between the elongate body of the posterior guide member 4 and the elongate body of the engagement member 7, so as to move the posterior guide member between a release position and a holding position.

The double ended screw 13 can be received in a first engaging bore 13*a* in the anterior guide member, a second engaging bore 13*c* in the posterior guide member and a non-engaging bore 13*b* in the engagement member.

In the embodiment shown in FIGS. 1*a-h* and 2*a-g*, this series of bores 13*a*, 13*b*, 13*c* is parallel to the connection bores 9*a*, 10*a*, 11*a*, 12*a*. Therefore in use the anterior guide member, the engagement member and posterior guide member are connected and aligned using the pair of proximal connector rails 9, 10 and the pair of distal connector rails 11, 12 and the double ended screw 13.

In the embodiment shown in FIGS. 7*a-d*, this series of bores is parallel to the connection bores for the proximal rail 509 and the distal rail 510. Therefore in use the anterior guide member 1, the engagement member 7 and the posterior guide member 4 are connected and aligned using the proximal rail 509 and the distal rail 510 and the double ended screw 13, which are parallel to one another.

In the embodiment shown in FIGS. 9*a-d*, this series of bores is parallel to the connection bores for the proximal rail 609, the distal rail 610, the medial rail 611 and the lateral rail 612. Therefore in use the anterior guide member 1, the engagement member 7 and posterior guide member 4 are connected and aligned using the proximal rail 609, the distal rail 610, the medial rail 611 and the lateral rail 612, and the double ended screw 13.

The double ended screw 13 does not engage with the non-engaging bore 13*b* in the engagement member. The non-threaded section in the middle of the double ended screw will be located in the non-engaging bore. Therefore the double ended screw extends through the engagement member but is not attached to the engagement member.

The double ended screw 13 does engage with the engaging bore 13*a* in the posterior guide member and does engage with the engaging bore 13*c* in the anterior guide member. The threaded portions at the two ends of the double ended screw are received in and engage with these engaging bores 13*a*, 13*c*. Therefore in use the double ended screw is attached to the anterior guide member and to the posterior guide member.

A key 600 may be provided that has a distal end 600*a* which engages with and rotates the double ended screw 13 (see FIGS. 7*d* and 9*a*).

The use of a double ended screw means that the anterior guide member 1 and the posterior guide member 4 can be simultaneously moved closer to or away from the engagement member 7 by the same distance.

Therefore when the anterior guide member and the posterior guide member are connected by the connector rails, via the engagement member, the elongate axes of the elongate bodies are substantially aligned and the angled channels converge in the direction of the distal end, such that the engagement protrusion can be located in a recess portion on the shoulder of the implant, with the anterior guide member and the posterior guide member in their release positions, and then the adjustment member can be used to move the anterior guide member towards its holding position until the first contact element contacts the surface of the shoulder of the implant, with the exit of the first angled channel lying spaced from the implant, and to simultaneously move the posterior guide member towards its holding position until the second contact element contacts the surface of the shoulder of the implant, with the exit of the second angled channel lying spaced from the implant.

The angled channel in the anterior guide member may be an integral part of the guide member. In other words, the angled channel is fixed within the anterior guide member. Likewise, the angled channel in the posterior guide member may be an integral part of the guide member. In other words, the angled channel is fixed within the posterior guide member.

However, the anterior guide member and the posterior guide member can each be provided with a recess that extends from its proximal end to its distal end and that can receive a channel providing unit 15 (see FIG. 1d). The channel providing unit is sized and shaped to slide into and be secured within the recess, extending substantially from the proximal end to the distal end. The channel providing unit includes one or more angled channel. The channel providing unit can be located and secured in the recess and when in this position it provides the guide member with an angled channel therein, running from an entrance at the proximal end of the guide member to an exit at the distal end of the guide member, wherein the channel is at an angle in the range of from 1 to 2.5 degrees, ideally 2 degrees, to the elongate axis of the elongate body.

As shown in FIG. 1d, the channel providing unit 15 can include multiple channels. However, this is optional rather than essential.

The targeting device may be used in combination with a medial targeting device 700, as shown in FIGS. 7a, 7d and 8b. This device can be used to double check the alignment of the targeting kit in the antero-posterior plane before the tunnels are drilled.

When a medial targeting device 700 is used, the targeting device is provided with an alignment slot 517 located at the proximal end of the engagement member 7 (See FIG. 9d). This alignment slot is in longitudinal alignment with the engagement protrusion 8 of the engagement member 7 as shown in FIG. 9c.

The medial targeting device 700 is in the form of a plate, which has an enlarged head 700a at the proximal end and an elongate body 700b that extends to the distal end. The enlarged head 700a is circular and is sized and shaped to be received in the alignment slot 517 of the engagement member 7 (see FIG. 7d). The elongate body 700b has a length greater than the distance from the alignment slot 517 to the engagement protrusion of the engagement member.

In use (see FIGS. 8a, 8b, 8c), the enlarged head 700a is received in the alignment slot 517 of the engagement member and the elongate body 700b of the medial targeting device is then pivoted until it contacts the proximal end of the neck 120 of the femoral implant. An assessment can be made as to whether the elongate plate is bisecting the neck centrally in the antero-posterior plane. If it is not, the location of the targeting device can be adjusted until the elongate plate of the medial targeting device does bisect the neck centrally in the antero-posterior plane.

An external targeting device of the invention is shown in FIGS. 10a-b. This can be used with the targeting device of the invention.

The external targeting device comprises a targeting device interlocking portion 701, an alignment portion 702, and a holding arrangement 703 for holding and pivoting the alignment portion 702 relative to the targeting device interlocking portion 701.

The targeting device interlocking portion 701 comprises a planar support body 704 provided with an anterior guide member interlocking component 705 and a posterior guide member interlocking component 706.

The anterior guide member interlocking component 705 comprises a first locking pin that extends from the planar support body in the same plane and can be received in the first angled channel. The posterior guide member interlocking component 706 comprises a second locking pin that extends from the planar support body in the same plane and can be received in the second angled channel. The location of the posterior guide member interlocking component 706 is fixed. A channel 707 is provided in the planar support body and the anterior guide member interlocking component 705 is provided with an engaging pin 708 that engages with and can slideably move along the channel and can be secured at any location therein. Thus the distance between the anterior guide member interlocking component 705 and the posterior guide member interlocking component 706 can be varied.

The alignment portion 702 comprises a planar elongate body 702a having an angled tip 702b at the distal end.

The holding arrangement comprises a pivot nut, a pivot washer, and a locking screw that can be rotated from an open position where pivoting can occur to a locked position where pivoting is prevented. The holding arrangement therefore holds the planar elongate body and the planar support body in the same plane, but permits the pivotal movement of the planar elongate body relative to the planar support body within that plane.

In use, the first locking pin can be received in the first angled channel of the targeting device, and the second locking pin can be received in second angled channel of the targeting device, such that the planar support body is aligned with the anterior-posterior plane in which the first and second angled channels lie, and such that the planar elongate body is consequently also aligned with the anterior-posterior plane in which the first and second angled channels lie, such that the planar elongate body can be pivoted relative to the planar support body until the angled tip is alongside the implant and the plane of the angled tip can be compared to the centreline in the anterior-posterior plane, as determined via x-ray.

If the plane of the angled tip is not aligned with the centreline in the anterior-posterior plane, the location of the targeting device can be adjusted until the angled tip does align with the centreline in the anterior-posterior plane.

The osteotome device of the invention is shown in FIGS. 3a-e.

The chevron osteotome device of the invention comprises an elongate body 100 having a proximal end 101 that can be provided with a handle 101a and a distal end 102 that can be blunt or may be sharp. The handle 101a can be understood to have an enlarged head portion extending from a neck.

The elongate body includes a distal section extending from the distal end to a shoulder point 103, wherein the shoulder point is located closer to the distal end than the proximal end.

The osteotome device also includes a cutting portion 104 extending outwardly from both sides of the elongate body at the shoulder point 103. The cutting portion has a first angled cutting side 104a that extends outwardly from one side of the elongate body at the shoulder point, and a second angled cutting side 104b that extends outwardly from the opposite side of the elongate body at the shoulder point.

The cutting portion 104 has a front face and a back face which are connected by the first angled cutting side and the second angled cutting side, the front face being aligned with and a continuation of the elongate body, and the back face being aligned with and a continuation of the elongate body, such that the cutting portion has the same depth as the elongate body. The front face and the back face are blunt.

Therefore the distal end of the chevron osteotome device can be located in an access tunnel and chevron osteotome device can be pushed in the direction of the distal end of the implant so as to cut away bony ingrowth on both sides of the access tunnel with the first angled cutting side and the second angled cutting side.

The elongate body has an upper face that is substantially planar and a lower face that is substantially planar. The distal end of the elongate body may optionally be rounded, as shown in the Figures.

The first angled cutting side and the second angled cutting side are located towards and face towards the distal end of the cutting portion, i.e. such that cutting occurs as the chevron osteotome device is pushed into the tunnel.

The cutting portion is a rhombus shape, with two sides of the rhombus being the first cutting side and the second cutting side (with these sides facing towards the distal end of the cutting portion). The third and fourth side of the rhombus (which face away from the distal end of the cutting portion) are blunt.

FIG. 3e shows a different shape for the handle 101a. In this shape there are no indents in the side edges of the handle, as compared to the handle shape shown in FIG. 3c. The handle 101a is essentially a square or rectangular protrusion from the elongate body. It can be understood to have an enlarged head portion extending from a neck.

In the embodiment of FIG. 3e the distal end 102 is also shown as sharp. The end may be chisel like, e.g. with a 45 degree angled sharp end. This compares with the embodiment of FIG. 3c where the distal end 102 is shown as blunt.

The curette device of the invention is shown in FIGS. 4a-d.

The curette device of the invention comprises an elongate body 200 in the form of a flat plate that extends from a first elongate edge 201 to a second elongate edge 202 and having a proximal end 203 that can be provided with a handle 203a and having a distal end 204 that is blunt. The handle 203a can be understood to have an enlarged head portion extending from a neck.

The curette device of the invention also comprises a first cutting portion 205 located at or near the distal end 204. This extends outwardly from the first elongate edge 201 of the elongate body. The cutting portion has a blunt edge 206 and a cutting edge 207 which meet at an angled cutting point 208. The blunt edge extends from a first location on the elongate body to the cutting point and the cutting edge extends from a second location on the elongate body to the cutting point, wherein the first location is closer to the distal end than the second location. Furthermore, the cutting edge is at an angle to the elongate axis of the curette device of from 50 to 85 degrees.

The curette device further comprises a second cutting portion 209, located between the second elongate edge 202 and the distal end 204 of the elongate body. In the embodiment illustrated, the second cutting portion 209 is provided on a curved edge that extends between the second elongate edge 202 and the distal end 204 of the elongate body. The second cutting portion is shown as comprising teeth, but alternatively or additionally, the second cutting portion may comprise a sharp edge.

Thus the curette device can be located in an access tunnel, with its elongate axis substantially aligned with the central axis running along the length of the tunnel, and with the distal end located at or near the distal (closed) end of the access tunnel, and then can be moved such that its elongate axis is angled with respect to the central axis running along the length of the tunnel, until the cutting edge contacts bony ingrowth located between the implant and the femoral cortex, and such that the curette device can then be withdrawn from the access tunnel whilst being retained in an angled position, such that as the device is withdrawn the cutting edge cuts away bony ingrowth located between the implant and the femoral cortex.

FIG. 4d shows a different shape for the handle 203a. In this shape there are no indents in the side edges of the handle, as compared to the handle shape shown in FIG. 4b. The handle 203a is essentially a square or rectangular protrusion from the elongate body 200. It can be understood to have an enlarged head portion extending from a neck.

In the embodiment of FIG. 4d the second cutting portion 209 is shown as comprising a sharp edge. The end may be chisel like, e.g. with a 45 degree angled sharp end. This compares with the embodiment of FIG. 4c where the second cutting portion 209 is shown as comprising teeth.

The medial-lateral clearance device of the invention is shown in FIGS. 5a-e. An alternative design is shown in FIGS. 11a-d.

The medial-lateral clearance device of the invention comprises an elongate body 300 having a proximal end 301 that can be provided with a handle 301a and having a distal end 302 that is blunt or may be sharp. The elongate body is in the shape of a flat plate that extends from a first elongate edge 303 to a second elongate edge 304. The handle 301a can be understood to have an enlarged head portion extending from a neck.

In the embodiment of FIGS. 11a-d the distal end 302 is shown as sharp. The end may be chisel like, e.g. with a 45 degree angled sharp end. This compares with the embodiment of FIGS. 4a-d where the distal end 302 is shown as blunt.

The medial-lateral clearance device of the invention also comprises a cutting portion 305 extending outwardly from the elongate body and located at or near the distal end 302. The cutting portion has an inner surface 306 that is flat and which connects with the first elongate edge of the elongate body at a substantially 90 degree angle. In FIGS. 5a-e the angle is 90 degrees. In FIGS. 11a-d the angle is 100 degrees.

The cutting portion has an outer surface 307 that comprises an angled cutting face 308 that is located towards the distal end of the elongate body. The inner surface meets the angled cutting face at a cutting edge 309, at an angle of from 20 to 70 degrees. This provides a sharp and chisel shaped end.

Thus the distal end of the flat plate elongate body can be located in a space at the bone-implant interface, at or near to the shoulder portion of the implant, with the flat plate being parallel to either the anterior surface or the posterior surface, and with the flat inner surface of the cutting portion aligned with either the medial or lateral surface of the implant, such that the medial-lateral clearance device can then be pushed in the direction of the distal end of the implant, with the flat plate elongate body remaining alongside the respective anterior or posterior surface, in the space at the bone-implant interface, whilst the angled cutting face cuts away bony ingrowth located at said medial or lateral surface of the implant as the device is pushed towards the distal end of the implant.

In another embodiment the cutting portion is not replaceable and therefore the medial-lateral clearance device is simply disposed of once the cutting edge is not sharp enough for continued use.

It will be appreciated that a pair of such medial-lateral clearance devices should be provided: one where the flat plate cutting portion is 90 to 110 degrees clockwise from the flat plate elongate body and one where the flat plate cutting portion is 90 to 100 degrees anticlockwise from the flat plate elongate body.

In addition, for both the "left handed" version and the "right handed" version, two or more different sizes may be provided.

Figures 6A, 6B:
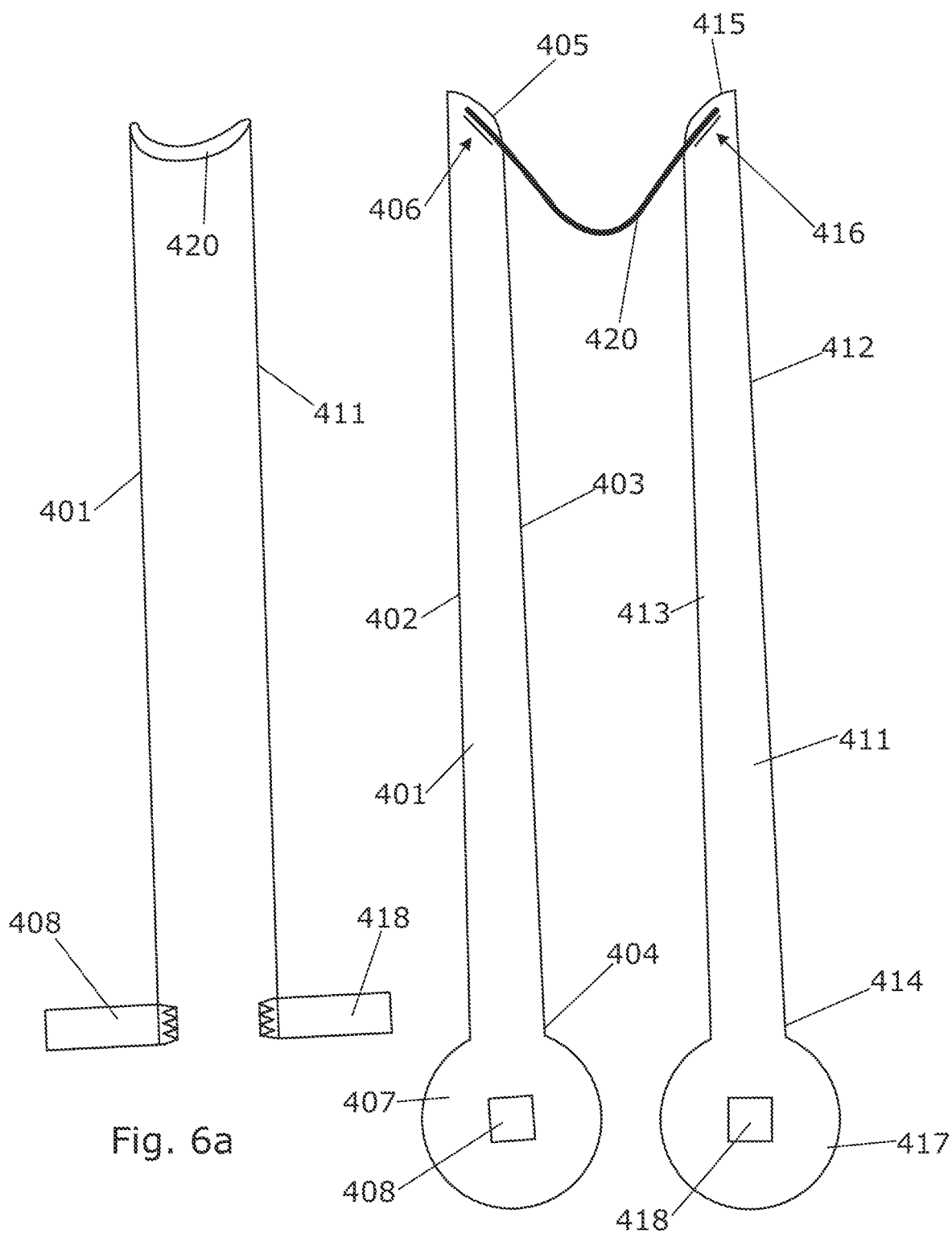
FIG. 6a is a side view of a wire delivery device of the invention
FIG. 6b is a front view of a wire delivery device of the invention

A wire delivery device of the invention is shown in FIGS. 6a-b.

The wire delivery device of the invention comprises a first elongate body 401 in the form of a flat plate that extends from a first elongate edge 402 to a second elongate edge 403.

The elongate body has a proximal end 404. A handle receiving portion 407 extends from the proximal end; this is shown as being circular in shape. The handle receiving portion 407 has a handle 408 extending outwardly therefrom, at 90 degrees to the flat plate elongate body 401.

The elongate body has a distal end 405 that is blunt. The distal end 405 slopes down from the first elongate edge 402 to the second elongate edge 403, at an angle to the elongate axis of the body of from 120 to 140 degrees, ideally about 135 degrees.

There is also a first wire guidance slot 406 provided in a spaced relationship with the distal end 405, the wire guidance slot running substantially parallel to this sloped distal end.

The wire delivery device of the invention further comprises a second elongate body 411 in the form of a flat plate that extends from a first elongate edge 412 to a second elongate edge 413.

The elongate body has a proximal end 414. A handle receiving portion 417 extends from the proximal end; this is shown as being circular in shape. The handle receiving portion 417 has a handle 418 extending outwardly therefrom, at 90 degrees to the flat plate elongate body 411.

The elongate body has a distal end 415 that is blunt. The distal end 415 slopes down from the first elongate edge 412 to the second elongate edge 413, at an angle to the elongate axis of the body of from 120 to 140 degrees, ideally about 135 degrees.

There is also a second wire guidance slot 416 provided in a spaced relationship with the distal end 415, the wire guidance slot running substantially parallel to this sloped distal end.

As shown in FIGS. 6a and 6b, a wire 420, such as a gigli wire, can be fed through and extend between the first wire guidance slot 406 and the second wire guidance slot 416. It can be secured in place by welding. The elongate bodies 401, 411 can be positioned in a spaced apart but aligned configuration with their second elongate edges 403, 413 closest to one another, so that the wire 420 extends into the space between the elongate bodies at an angle of from 120 to 140 degrees, especially 135 degrees.

When the device is ready to be used, the wire 420 can be pulled taught between the two elongate bodies 401, 411 and can then be used to cut the bone-implant interface by pulling the first and second elongate bodies in an alternating motion or by pushing the first and second elongate bodies in an alternating motion.

The wire delivery device can be operated manually or the first and second elongate bodies can be attached to a reciprocating saw or another reciprocating mechanism that automatically moves the device forwards and backwards in a linear fashion.

An alternative design for the wire delivery device of the invention is shown in FIGS. 14a-c.

The wire delivery device of the invention uses an elongate body 901 in the form of a flat plate that extends from a first elongate edge 902 to a second elongate edge 903.

The elongate body has a proximal end 904 with a handle 907. The handle 907 can be understood to have an enlarged head portion extending from a neck.

The elongate body has a distal end 905 that is blunt.

There is a wire guidance slot 906 provided in a spaced relationship with the distal end 905 and located within the first elongate body, wherein the wire guidance slot runs from an entrance 906a at the first elongate edge to an exit 906b at the second elongate edge, wherein the distance between the entrance 906a and the distal end 905 is greater than the distance between the exit 906b and the distal end 905, such that the wire guidance slot is at an angle to the elongate axis of the body of from 120 to 140 degrees, ideally about 135 degrees.

To use the wire delivery device of the invention, two of these elongate body devices 901 are used.

A wire, such as a Gigli wire, can be fed through and extend between the wire guidance slots of the two elongate body devices. It can be secured in place by welding. The elongate body devices can be positioned in a spaced apart but aligned configuration with their second elongate edges closest to one another, so that the wire extends into the space between the elongate bodies at an angle of from 120 to 140 degrees, especially 135 degrees.

When the device is ready to be used, the wire can be pulled taught between the two elongate body devices and can then be used to cut the bone-implant interface by pulling the first and second elongate bodies in an alternating motion or by pushing the first and second elongate bodies in an alternating motion.

The wire delivery device can be operated manually or the first and second elongate bodies can be attached to a reciprocating saw or another reciprocating mechanism that automatically moves the device forwards and backwards in a linear fashion.

The brace sleeve 750 of the invention is shown in FIG. 12. The brace sleeve 750 can be used to provide structural support for the elongate body of any of the devices described above and shown in the preceding drawings, except for the targeting device which it will be appreciated does not have an elongate body.

The brace sleeve 750 comprises two elongate faces 751, 752 which are joined at one elongate edge 753 and are open at the opposite elongate edge and at both the two ends, so as to create an elongate cavity between the two faces within which an elongate body can be slidably received. The brace sleeve can slide onto and over an elongate body to provide additional strength and resistance to bending during use. The brace sleeve can cover some, most or all of the length of an elongate body of any of the devices described above.

The two elongate faces may be flat and parallel to one another. However, in the illustrated embodiment, one of the elongate faces 752 flares outwardly towards the open elongate edge. This can assist with ease of placing the brace sleeve onto the elongate body, because it means that the open "mouth" of the brace sleeve is larger than the closed edge.

The universal handle 800 of the invention is shown in FIGS. 13*a-c*. The universal handle 800 can be used as a handle for two or more of the devices described above, except for the targeting device which it will be appreciated does not require a handle. The universal handle 800 comprises a body 801 having two grip portions 802 at its proximal end and an engagement recess 803 in the form of a slot, at its distal end. The engagement recess is sized and shaped to receive the proximal end (handle) of the devices described above, except for the targeting device. As shown in the drawings, the handle of the devices described above comprises a neck and an enlarged head.

The universal handle 800 is provided with a locking cap 804 which fits over the distal end of the body 801 and permits the enlarged head of the handle to be locked in place in the engagement recess 803. The locking cap 804 is provided with a dual slot 805, comprising a first elongate shaped slot 805*a* that can receive the enlarged head and allow it to pass therethrough, and a second elongate shaped slot 805*b* that can receive the neck and allow it to pass therethrough but that is too small to allow the enlarged head to pass therethrough. The first elongate shaped slot and the second elongate shaped slot overlap, with the elongate axis of the first elongate shaped slot being at an angle to the elongate axis of the second elongate shaped slot. Therefore the locking cap 804 can be placed over the distal end of the body with the first elongate shaped slot 805*a* aligned with the engagement recess and the enlarged head can pass through the first elongate shaped slot and into the engagement recess. Then the locking cap can be rotated such that the second elongate shaped slot 805*b* is aligned with the engagement recess, meaning that the enlarged head is locked into the engagement recess because it is too big to pass through the second elongate shaped slot. When it is desired to release the universal handle from the device, the locking cap can be rotated until the first elongate shaped slot is aligned with the engagement recess again.

The locking cap is spring loaded to assist with release. Therefore a torsion spring 806 is provided between the body 801 and the locking cap 804, which biases the locking cap away from the body. The user can overcome that biasing force by pushing the locking cap onto the body. The locking cap can be held in place by the use of a securing means 807 (e.g. a locking pin and corresponding aperture) that connects the locking cap and the body.

FIGS. 15*a-c* show a chevron chisel according to the invention. The chevron chisel comprises an elongate body 950 in the form of a flat plate having an upper face 950*a* and a lower face 950*b*. The elongate body 950 extends from a first elongate edge 951 to a second elongate edge 952.

The elongate body 950 has a proximal end 953 that can be provided with a handle 954. The handle 954 can be understood to have an enlarged head portion extending from a neck.

The elongate body 950 has a distal end 955. A cutting portion is located at the distal end 955. The cutting portion comprises a first cutting face 956 and a second cutting face 957 which meet at an angled cutting point 958. The angled cutting point is located substantially centrally between the first elongate edge and the second elongate edge.

The first cutting face 956 extends at an angle of about 45 degrees from the first elongate edge 951 when measured with respect to the elongate axis of the elongate body, and the second cutting face 957 extends at an angle of about 45 degrees from the second elongate edge 952 when measured with respect to the elongate axis of the elongate body. In addition, the first cutting face 956 extends at an angle of about 45 degrees from the lower face to the upper face, and the second cutting face 957 extends at an angle of about 45 degrees from the lower face to the upper face.

The chevron chisel may optionally have a depth (the lower face to the upper face) of from 0.5 to 3 mm, e.g. 1 to 2 mm; it may be about 1 mm deep. The chevron chisel may optionally have a width (first elongate edge to a second elongate edge) of from 4 to 10 mm, e.g. 5 to 9 mm; it may be about 7 to 8 mm wide.

The invention claimed is:

1. A targeting device suitable for use in removing a femoral implant from the surrounding tissue, wherein the device comprises:
    an anterior guide member, which comprises a first elongate body provided with a first angled channel therein, running from an entrance at the proximal end of the anterior guide member to an exit at the distal end of the anterior guide member, and where the first elongate body has a first contact element at its distal end for contacting the anterior surface of the shoulder of the femoral implant, and whereby, in use, the exit at the distal end of the anterior guide member is spaced apart from the anterior surface of the shoulder of the implant,
    a posterior guide member, which comprises a second elongate body provided with a second angled channel therein, running from an entrance at the proximal end of the posterior guide member to an exit at the distal end of the posterior guide member, and where the second elongate body has a second contact element at its distal end for contacting the posterior surface of the shoulder of the implant, and whereby, in use, the exit at the distal end of the posterior guide member is spaced apart from the posterior surface of the shoulder of the implant,
    an engagement member for locating and engaging the targeting device on the shoulder of the implant, which comprises a third elongate body with an engagement protrusion at its distal end, whereby the engagement protrusion can be received in a recess portion on the shoulder of the implant, and whereby the third elongate body can be located between and aligned with the first elongate body and the second elongate body, such that the elongate axes of the first, second and third elongate bodies are substantially aligned, and with the first and second angled channels converging in the direction of the distal end,
    a first pair of parallel connector rails, wherein each connector rail can slideably connect the anterior guide member and the posterior guide member via the engagement member, with the connector rails being received in connection bores in the anterior guide member and the posterior guide member,
    an adjustment system which can adjust the distance between the first elongate body and the third elongate body, so as to move the anterior guide member between a release position and a holding position, and which can adjust the distance between the second elongate body and the third elongate body, so to move the posterior guide member between a release position and a holding position;

wherein when the anterior guide member and the posterior guide member are connected by the first pair of connector rails, via the engagement member, the elongate axes of the elongate bodies are substantially aligned and the angled channels converge in the direction of the distal end, with the convergence angle of the angled channels being in the range of from 2 to 6 degrees, such that the engagement protrusion can be located in a recess portion on the shoulder of the implant, with the anterior guide member and the posterior guide member in their release positions, and then the adjustment system can be used to move the anterior guide member towards its holding position until the first contact element contacts the shoulder of the implant, with the exit of the first angled channel lying spaced from the anterior surface of the implant, and to move the posterior guide member towards its holding position until the second contact element contacts the shoulder of the implant, with the exit of the second angled channel lying spaced from the posterior surface of the implant.

2. The targeting device of claim 1, wherein the angled channel in the anterior guide member is an integral part of the anterior guide member and the angled channel in the posterior guide member is an integral part of the posterior guide member.

3. The targeting device of claim 1, wherein the anterior guide member is provided with a recess that extends from its proximal end to its distal end and that can receive an anterior channel providing unit that includes one or more angled channels, wherein the anterior channel providing unit is sized and shaped to slide into and be secured within the recess, extending substantially from the proximal end to the distal end, and wherein the posterior guide member is provided with a recess that extends from its proximal end to its distal end and that can receive a posterior channel providing unit that includes one or more angled channels, wherein the posterior channel providing unit is sized and shaped to slide into and be secured within the recess, extending substantially from the proximal end to the distal end.

4. The targeting device of claim 1, wherein the angle of the (or each) anterior angled channel and the angle of the (or each) posterior angled channel are selected from: 1 degree, 1.5 degrees, 2 degrees, 2.5 degrees and 3 degrees.

5. The targeting device of claim 1, wherein the anterior angled channel(s) and the posterior angled channel(s) have circular cross sections, or square cross sections, or rectangular cross sections, or combinations thereof.

6. The targeting device of claim 1, wherein the first contact element at the distal end of the guide member is a lip or a leg that extends from the distal end of the elongate body, and wherein the second contact element at the distal end of the guide member is a lip or a leg that extends from the distal end of the elongate body.

7. The targeting device of claim 6 wherein each lip or leg is provided with a contact face for contacting the shoulder of the femoral implant.

8. The targeting device of claim 6 wherein each lip or leg is provided with one or more engaging protrusions that can protrude into the cancellous bone anteriorly or posteriorly.

9. The targeting device of claim 1, wherein the first pair of parallel connector rails comprises one proximal rail and one distal rail.

10. The targeting device of claim 9, wherein the proximal rail and the distal rail are located at or near the midpoint between the medial face of the anterior guide member and the posterior guide member and the lateral face of the anterior guide member and the posterior guide member.

11. The targeting device of claim 1, wherein the first pair of parallel connector rails comprises one medial rail and one lateral rail.

12. The targeting device of claim 11, wherein the medial rail and the lateral rail are located at or near the midpoint between the proximal end of the guide members and the distal end of the guide members.

13. The targeting device of claim 1, wherein the adjustment system is a double ended screw.

14. The targeting device of claim 1, wherein the device is made of medical grade stainless steel and/or sterilized plastic.

15. A kit comprising the targeting device as defined in claim 1, together with one or more of:
(a) an osteotome device that can remove bony ingrowth located adjacent to the anterior access tunnel, and remove bony ingrowth located adjacent to the posterior access tunnel and the posterior surface of the implant;
(b) a curette device that can remove bony ingrowth located between the implant and the femur in the anterior aspect, and remove bony ingrowth located between the implant and the femur in the posterior aspect;
(c) a medial-lateral clearance device that can clear the medial surface of the implant of bony ingrowth at or near to where it adjoins the anterior surface of the implant and at or near to where it adjoins the posterior surface of the implant, and that can clear the lateral surface of the implant of bony ingrowth at or near to where it adjoins the anterior surface of the implant and at or near to where it adjoins the posterior surface of the implant;
(d) a wire delivery device that can be used for clearing the medial aspect of a collared implant of bony ingrowth.

16. The kit of claim 15, further comprising a chevron chisel which comprises:
an elongate body in the form of a flat plate having an upper face and a lower face, wherein the elongate body extends from a first elongate edge to a second elongate edge and having a proximal end that can be provided with a handle and having a distal end; and
a cutting portion located at the distal end which comprises a first cutting face and a second cutting face which meet at an angled cutting point, wherein the first cutting face extends at an angle of from 30 to 60 degrees from the first elongate edge when measured with respect to the elongate axis of the elongate body, and the second cutting face extends at an angle of from 30 to 60 degrees from the second elongate edge when measured with respect to the elongate axis of the elongate body, and wherein the first cutting face extends at an angle of from 30 to 60 degrees from the lower face to the upper face, and wherein the second cutting face extends at an angle of from 30 to 60 degrees from the lower face to the upper face.

17. The kit of claim 16, wherein the first cutting face extends at an angle of from 40 to 50 degrees from the first elongate edge when measured with respect to the elongate axis of the elongate body, and the second cutting face extends at an angle of from 40 to 50 degrees from the second elongate edge when measured with respect to the elongate axis of the elongate body, and wherein the first cutting face extends at an angle of from 40 to 50 degrees from the lower face to the upper face, and wherein the second cutting face extends at an angle of from 40 to 50 degrees from the lower face to the upper face.

18. The targeting device of claim 1, wherein the convergence angle of the angled channels is in the range of from 2 to 5 degrees.

* * * * *